US010231451B2

(12) United States Patent
Satchivi et al.

(10) Patent No.: US 10,231,451 B2
(45) Date of Patent: Mar. 19, 2019

(54) SYNERGISTIC WEED CONTROL FROM APPLICATIONS OF PYRIDINE CARBOXYLIC ACID HERBICIDES AND SYNTHETIC AUXIN HERBICIDES AND/OR AUXIN TRANSPORT INHIBITORS

(71) Applicant: Dow AgroSciences LLC, Indianapolis, IN (US)

(72) Inventors: Norbert M. Satchivi, Carmel, IN (US); Bryston L. Bangel, Camby, IN (US); Rory Frank Degenhardt, Edmonton (CA); Len Juras, Saskatoon (CA); Paul R. Schmitzer, Indianapolis, IN (US); Jared L. Bell, Brownsburg, IN (US); Jennifer Lynn Ransberger, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/346,817

(22) Filed: Nov. 9, 2016

(65) Prior Publication Data
US 2017/0064955 A1 Mar. 9, 2017

Related U.S. Application Data

(63) Continuation of application No. 14/854,912, filed on Sep. 15, 2015, now Pat. No. 9,521,847.

(60) Provisional application No. 62/050,719, filed on Sep. 15, 2014, provisional application No. 62/050,710, filed on Sep. 15, 2014.

(51) Int. Cl.
| | | |
|---|---|---|
| A01N 37/10 | (2006.01) |
| A01N 37/30 | (2006.01) |
| A01N 37/40 | (2006.01) |
| A01N 39/02 | (2006.01) |
| A01N 39/04 | (2006.01) |
| A01N 43/40 | (2006.01) |
| A01N 43/42 | (2006.01) |
| A01N 43/54 | (2006.01) |
| A01N 43/78 | (2006.01) |
| A01N 47/34 | (2006.01) |
| C07D 401/04 | (2006.01) |
| C07D 405/04 | (2006.01) |
| C07D 409/04 | (2006.01) |
| C07D 417/04 | (2006.01) |

(52) U.S. Cl.
CPC ............ *A01N 43/40* (2013.01); *A01N 37/10* (2013.01); *A01N 37/30* (2013.01); *A01N 37/40* (2013.01); *A01N 39/02* (2013.01); *A01N 39/04* (2013.01); *A01N 43/42* (2013.01); *A01N 43/54* (2013.01); *A01N 43/78* (2013.01); *A01N 47/34* (2013.01); *C07D 401/04* (2013.01); *C07D 405/04* (2013.01); *C07D 409/04* (2013.01); *C07D 417/04* (2013.01)

(58) Field of Classification Search
CPC combination set(s) only.
See application file for complete search history.

(56) References Cited

U.S. PATENT DOCUMENTS

| | | |
|---|---|---|
| 6,297,197 B1 | 10/2001 | Fields et al. |
| 6,784,137 B2 | 8/2004 | Balko et al. |
| 7,300,907 B2 | 11/2007 | Epp et al. |
| 7,314,849 B2 | 1/2008 | Balko et al. |
| 7,498,468 B2 | 3/2009 | Balko et al. |
| 7,538,214 B2 | 5/2009 | Epp et al. |
| 7,642,220 B2 | 1/2010 | Epp et al. |
| 7,863,220 B2 | 1/2011 | Clark et al. |
| 7,888,287 B2 | 2/2011 | Epp et al. |
| 8,288,318 B2 | 10/2012 | Epp et al. |
| 8,426,591 B2 | 4/2013 | Guenthenspberger et al. |
| 8,536,331 B2 | 9/2013 | Eckelbarger et al. |
| 8,609,592 B2 | 12/2013 | Guenthenspberger et al. |

(Continued)

FOREIGN PATENT DOCUMENTS

| | | |
|---|---|---|
| CA | 2842830 A1 | 1/2013 |
| WO | 2003011853 A1 | 2/2003 |

(Continued)

OTHER PUBLICATIONS

Tomlin, C.D.S., The Pesticide Manual, 15th ed., British Crop Protection Council, Hampshire, UK, pp. 33-35, 549-551, 1161-1163 (2009).*
Tordon 22K label, Dow AgroSciences, pp. 1-13 (2009).*
International Search Report and Written Opinion of the EP International Searching Authority from International Application No. PCT/EP2012/064519 dated Sep. 28, 2012.
International Search Report and Written Opinion issued in International Application No. PCT/US2014/024745 dated Jul. 7, 2014.

(Continued)

*Primary Examiner* — John Pak
(74) *Attorney, Agent, or Firm* — Meunier Carlin & Curfman, LLC

(57) ABSTRACT

Disclosed herein are herbicidal compositions comprising a herbicidally effective amount of (a) a pyridine carboxylic acid herbicide or an agriculturally acceptable N-oxide, salt or ester thereof, and (b) a synthetic auxin herbicide, an auxin transport inhibitor, agriculturally acceptable salts or esters thereof, or combinations thereof. Also disclosed herein are methods of controlling undesirable vegetation which comprise applying to vegetation or an area adjacent the vegetation or applying to soil or water to prevent the emergence or growth of vegetation (a) a pyridine carboxylic acid herbicide or an agriculturally acceptable N-oxide, salt or ester thereof, and (b) a synthetic auxin herbicide, an auxin transport inhibitor, agriculturally acceptable salts or esters thereof, or combinations thereof, wherein (a) and (b) are each added in an amount sufficient to provide a herbicidal effect.

31 Claims, No Drawings

(56) References Cited

U.S. PATENT DOCUMENTS

| | | |
|---|---|---|
| 8,754,229 B2 | 6/2014 | Epp et al. |
| 9,113,629 B2 | 8/2015 | Eckelbarger et al. |
| 9,179,676 B2 | 11/2015 | Hoffmann et al. |
| 9,521,847 B2 * | 12/2016 | Satchivi .............. C07D 405/04 |
| 2003/0114311 A1 | 6/2003 | Balko et al. |
| 2007/0179059 A1 | 8/2007 | Epp et al. |
| 2008/0045734 A1 | 2/2008 | Balko et al. |
| 2008/0051596 A1 | 2/2008 | Balko et al. |
| 2008/0234262 A1 | 9/2008 | Zask et al. |
| 2009/0048109 A1 | 2/2009 | Epp et al. |
| 2009/0062121 A1 | 3/2009 | Satchivi et al. |
| 2009/0088322 A1 | 4/2009 | Epp et al. |
| 2009/0264429 A1 | 10/2009 | Apodaca et al. |
| 2010/0137137 A1 | 6/2010 | Rosinger et al. |
| 2010/0137138 A1 | 6/2010 | Rosinger et al. |
| 2010/0179127 A1 | 7/2010 | Floersheim et al. |
| 2010/0285959 A1 | 11/2010 | Armel et al. |
| 2011/0105325 A1 | 5/2011 | Satchivi et al. |
| 2011/0136666 A1 | 6/2011 | Whittingham et al. |
| 2011/0281873 A1 | 11/2011 | Chiang et al. |
| 2012/0015811 A1 | 1/2012 | Dave et al. |
| 2012/0115724 A1 | 5/2012 | Whittingham et al. |
| 2012/0157314 A1 | 6/2012 | Ahrens et al. |
| 2012/0184435 A1 | 7/2012 | Bristow et al. |
| 2012/0190548 A1 | 7/2012 | Eckelbarger et al. |
| 2012/0190549 A1 | 7/2012 | Eckelbarger et al. |
| 2012/0288492 A1 | 11/2012 | Kuo et al. |
| 2012/0292905 A1 | 11/2012 | Slot |
| 2013/0143738 A1 | 6/2013 | Ovalle et al. |
| 2013/0143739 A1 | 6/2013 | Ovalle et al. |
| 2013/0310358 A1 | 11/2013 | Coats et al. |
| 2013/0345240 A1 | 12/2013 | Whitten et al. |
| 2014/0031214 A1 | 1/2014 | Yerkes et al. |
| 2014/0031217 A1 | 1/2014 | Yerkes et al. |
| 2014/0274695 A1 * | 9/2014 | Eckelbarger ............ A01N 43/40 504/103 |
| 2014/0274701 A1 | 9/2014 | Eckelbarger et al. |
| 2015/0005165 A1 | 1/2015 | Hoffmann et al. |

FOREIGN PATENT DOCUMENTS

| | | |
|---|---|---|
| WO | 2005063721 A1 | 7/2005 |
| WO | 2006121648 A2 | 11/2006 |
| WO | 2007080382 A1 | 7/2007 |
| WO | 2007082076 A1 | 7/2007 |
| WO | 2007082098 A2 | 7/2007 |
| WO | 2009007751 A2 | 1/2009 |
| WO | 2009023438 A1 | 2/2009 |
| WO | 2009029735 A1 | 3/2009 |
| WO | 2009081112 A2 | 7/2009 |
| WO | 2010060581 A2 | 6/2010 |
| WO | 2010092339 A1 | 8/2010 |
| WO | 2009138712 A3 | 9/2010 |
| WO | 2010125332 A1 | 11/2010 |
| WO | 2011080568 A2 | 7/2011 |
| WO | 2012080187 A1 | 6/2012 |
| WO | 2012149528 A1 | 11/2012 |
| WO | 2013003740 A1 | 1/2013 |
| WO | 2013014165 A1 | 1/2013 |

OTHER PUBLICATIONS

International Search Report and Written Opinion issued in International Application No. PCT/US2014/024749, dated Jul. 10, 2014.
International Search Report and Written Opinion issued in International Application No. PCT/US2014/024752 dated Jul. 7, 2014.
International Search Report and Written Opinion issued in International Application No. PCT/US2015/050190 dated Dec. 29, 2015.
International Search Report and Written Opinion issued in International Application No. PCT/US2015/50203 dated Jan. 14, 2016.
International Search Report and Written Opinion issued in International Application No. PCT/US2015/50205 dated Jan. 14, 2016.
International Search Report and Written Opinion issued in International Application No. PCT/US2015/50209 dated Jan. 14, 2016.
International Search Report and Written Opinion issued in related International Application No. PCT/US2015/050122 dated Jul. 5, 2016.
Abell, "Target-Site Directed Herbicide Design in, pest control with enhanced environmental safety 15-37", 1993.
Knight, et al., "Annual Review of Phytopathology", 1997.
Pubchem. Substance Record for SID 172846318. Deposit Date: Mar. 7, 2013. [retrieved on Dec. 1, 2015]. Retrieved from the Internet, <URL:https://pubchem.ncbl.nlm.nih.gov/substance/172846318/version/1#section=Top>. entire document.
Ruegg, et al., "Weed Research", 2006.
Extended European Search Report dated Apr. 3, 2018 in related European Application 15841269 (13 pages).
International Search Report and Written Opinion dated Jul. 14, 2014 in related PCT Application No. PCT/US2014/024388 (10 pages).

* cited by examiner

SYNERGISTIC WEED CONTROL FROM APPLICATIONS OF PYRIDINE CARBOXYLIC ACID HERBICIDES AND SYNTHETIC AUXIN HERBICIDES AND/OR AUXIN TRANSPORT INHIBITORS

CROSS REFERENCE TO RELATED APPLICATIONS

This application is a continuation of U.S. Ser. No. 14/854,912 filed Sep. 15, 2015, which claims benefit of U.S. Provisional Patent Application No. 62/050,719, filed Sep. 15, 2014, and U.S. Provisional Patent Application No. 62/050,710, filed Sep. 15, 2014, which are hereby incorporated herein by reference in their entireties.

FIELD OF THE DISCLOSURE

The present disclosure relates to herbicidal compositions comprising a herbicidally effective amount of (a) a pyridine carboxylic acid herbicide or an agriculturally acceptable N-oxide salt or ester thereof, and (b) a synthetic auxin herbicide, an auxin transport inhibitor, agriculturally acceptable salts or esters thereof, or combinations thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Disclosed herein are herbicidal compositions comprising a herbicidally effective amount of (a) a pyridine carboxylic acid herbicide or an agriculturally acceptable N-oxide, salt, or ester thereof, and (b) a synthetic auxin herbicide, auxin transport inhibitor, agriculturally acceptable salts or esters thereof, or combinations thereof. In some embodiments, (a) and (b) can be provided in a synergistic herbicidally effective amount. In some embodiments, (b) can comprise a synthetic auxin herbicide or an agriculturally acceptable salt or ester thereof, and the weight ratio of (a) to (b) can be from 1:8000 to 30:1 (e.g., 1:3000 to 60:1, from 1:2225 to 30:1, from 1:200 to 8:1, from 1:70 to 1:1, or from 1:85 to 3.5:1). In some embodiments, (b) can comprise an auxin transport inhibitor, or an agriculturally acceptable salt or ester thereof, and the weight ratio of (a) to (b) can be from 1:1000 to 85:1 (e.g., 1:200 to 12:1, from 1:30 to 5:1, from 1:2 to 12:1, from 1:1 to 6:1, or from 1.25:1 to 5:1).

The pyridine carboxylic acid herbicide can comprise a compound defined by Formula (I)

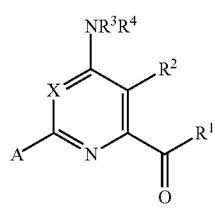

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups A1 to A36

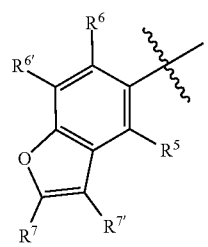

A1

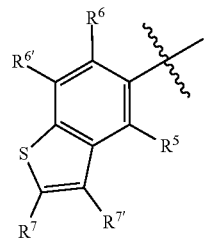

A2

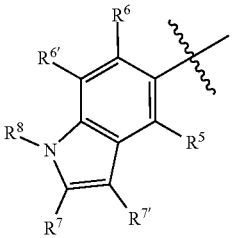

A3

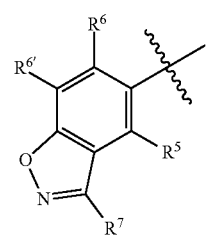 A4
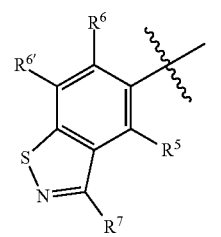 A5
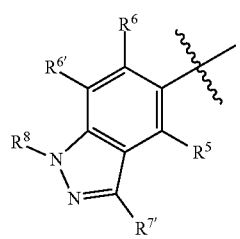 A6
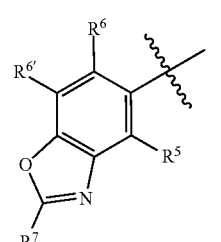 A7
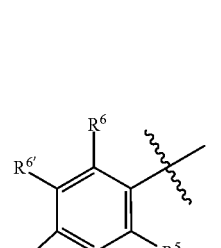 A8
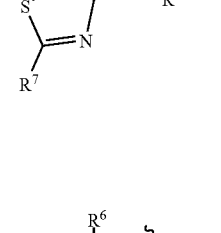 A9
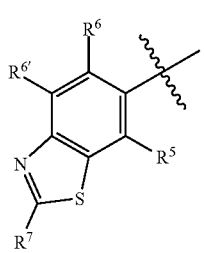 A10
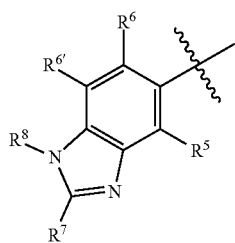 A11
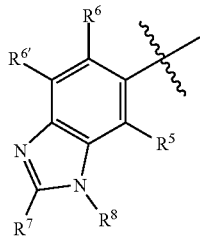 A12
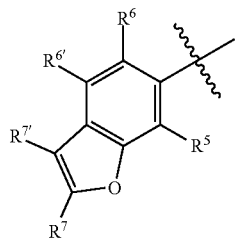 A13
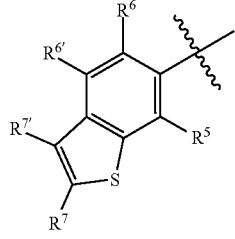 A14
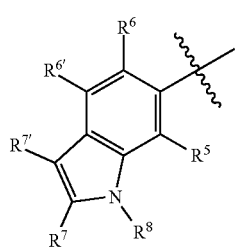 A15

| | |
|---|---|
| 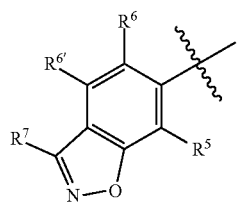 | A16 |
| 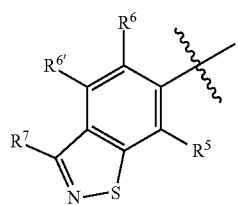 | A17 |
| 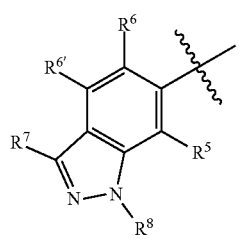 | A18 |
| 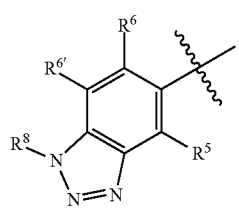 | A19 |
| 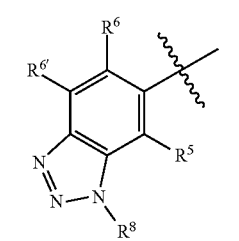 | A20 |
| 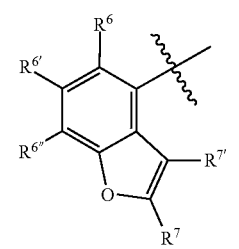 | A21 |
| 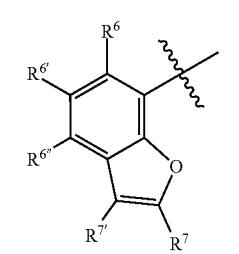 | A22 |
| 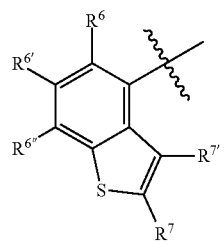 | A23 |
| 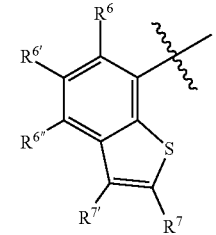 | A24 |
| 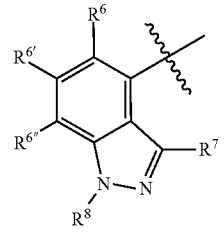 | A25 |
| 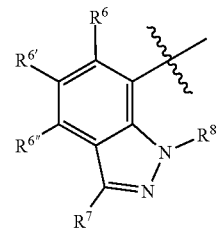 | A26 |
| 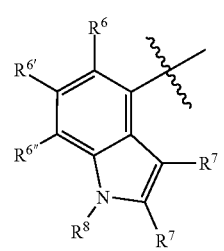 | A27 |
| 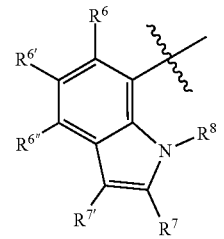 | A28 |

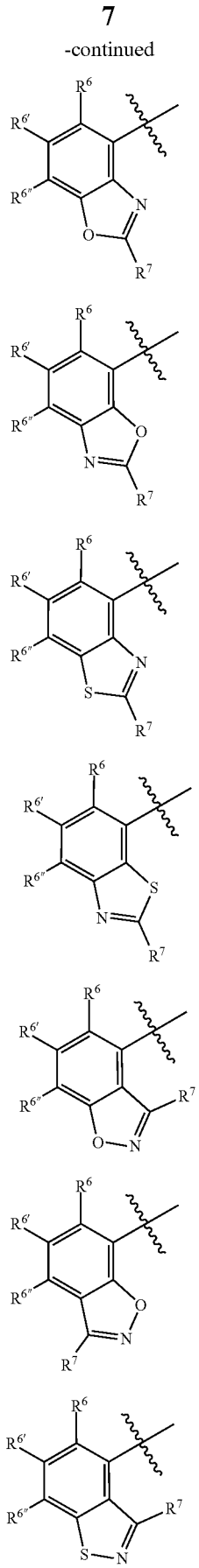

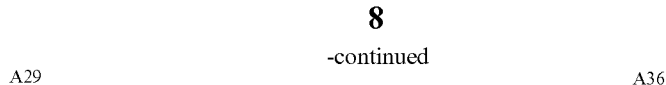

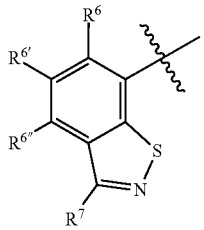

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, A is A1, A2, A3, A7, A8, A9, A10, A11, A12, A13, A14, or A15. In some cases, A is A1, A2, A3, A7, A8, A9, A10, A13, A14, or A15. In certain cases, A is A2, A3, A8, A13, or A15.

In certain embodiments, the pyridine carboxylic acid herbicide can comprise a compound defined by Formula (II):

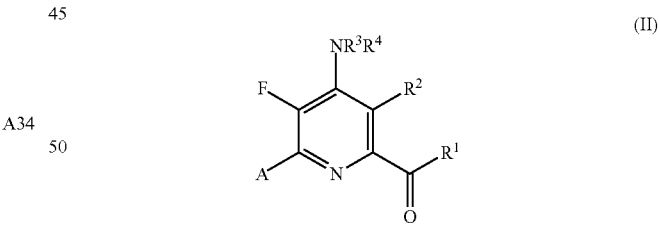

wherein $R^1$ is $OR^{1''}$ or $NR^{1''}R^{1'''}$, wherein $R^{1''}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

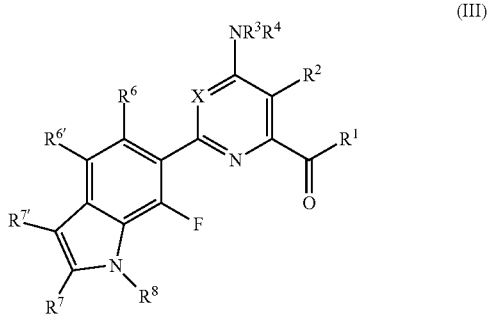

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $—CR^{17}=CR^{18}—SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, X is N, CH or CF. In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (IV):

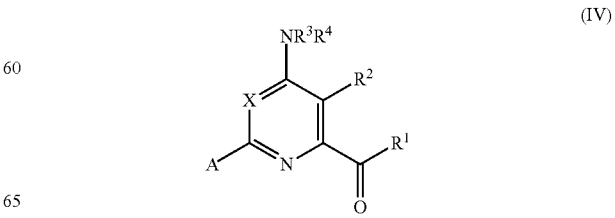

(IV)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, F, Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^2$ is $C_2$-$C_4$-alkenyl, $C_2$-$C_4$ haloalkenyl, or $C_1$-$C_4$-alkoxy. In certain embodiments, $R^2$ is methoxy, vinyl, 1-fluorovinyl, or 1-propenyl. In some cases, $R^3$ and $R^4$ are hydrogen. In some embodiments, A is A1, A2, A3, A7, A8, A9, A10, A13, A14, or A15. In certain cases, A is A2, A3, A8, A13, or A15. In certain cases, A is A1, A2, A3, A13, A14, or A15.

In certain embodiments, the pyridine carboxylic acid herbicide can include 4-amino-3-chloro-5-fluoro-6-(7-fluoro-1H-indol-6-yl) picolinic acid, or an agriculturally acceptable N-oxide, salt, or ester thereof.

In some embodiments, (b) can comprise a phenoxy herbicide, a benzoic acid herbicide, a carboxylic acid herbicide, agriculturally acceptable salts and esters thereof, or a combination thereof. In certain embodiments, (b) can include 2,4-D, 2,4-DB, MCPA, MCPB, 4-amino-3-chloro-6-(4-chloro-2-fluoro-3-methoxyphenyl)-5-fluoro-2-pyridinecarboxylic acid, benzyl 4-amino-3-chloro-6-(4-chloro-2-fluoro-3-methoxyphenyl)-5-fluoro-2-pyridinecarboxylate, aminocyclopyrachlor, aminopyralid, chloramben, clomeprop, dichlorprop, mecoprop, dicamba, clopyralid, fluroxypyr, halauxifen, halauxifen-methyl, picloram, quinclorac, quinmerac, triclopyr, agriculturally acceptable salts and esters thereof, or a combination thereof.

In some embodiments, (b) can comprise a semicarbazone herbicide, phthalamate herbicide, or other benzoic acid, agriculturally acceptable salts and esters thereof, or a combination thereof. In certain embodiments, (b) can include diflufenzopyr, naptalam, 2,3,5-triiodobenzoic acid, agriculturally acceptable salts and esters thereof, or a combination thereof.

The composition can further comprise an additional pesticide, a herbicidal safener, an agriculturally acceptable adjuvant or carrier, or a combination thereof. The composition can be provided as a herbicidal concentrate. In certain embodiments, the active ingredients in the composition consist of (a) and (b).

The present disclosure also relates to methods of controlling undesirable vegetation which comprise applying to vegetation or an area adjacent the vegetation or applying to soil or water to prevent the emergence or growth of vegetation a herbicidally effective amount of (a) a pyridine carboxylic acid herbicide or an agriculturally acceptable N-oxide, salt, or ester thereof, and (b) a synthetic auxin herbicide, an auxin transport inhibitor, agriculturally acceptable salts or esters thereof, or combinations thereof. In some embodiments, (a) and (b) are provided in a synergistically effective amount. In some embodiments, (a) and (b) are applied simultaneously. In some embodiments, (a) and (b) are applied post-emergence of the undesirable vegetation.

In some embodiments, (a) can comprise a pyridine carboxylic acid herbicide described above. In certain embodiments, (a) can comprise 4-amino-3-chloro-5-fluoro-6-(7-fluoro-1H-indol-6-yl) picolinic acid or an agriculturally acceptable N-oxide, salt, or ester thereof. In some cases, (a) can be applied in an amount of from 0.1 grams acid equivalent per hectare (g ae/ha) to 300 g ae/ha (e.g., from 0.5 g ae/ha to 300 g ae/ha, from 5 g ae/ha to 40 g ae/ha).

In some embodiments, (b) can comprise a phenoxy herbicide, benzoic acid herbicide, carboxylic acid herbicide, agriculturally acceptable salts and esters thereof, or a combination thereof. In certain embodiments, (b) can include 2,4-D, 2,4-DB, MCPA, MCPB, 4-amino-3-chloro-6-(4-chloro-2-fluoro-3-methoxyphenyl)-5-fluoro-2-pyridinecarboxylic acid, benzyl 4-amino-3-chloro-6-(4-chloro-2-fluoro-3-methoxyphenyl)-5-fluoro-2-pyridinecarboxylate, aminocyclopyrachlor, aminopyralid, chloramben, clomeprop, dichlorprop, mecoprop, dicamba, clopyralid, fluroxypyr, halauxifen, halauxifen-methyl, picloram, quinclorac, quinmerac, triclopyr, agriculturally acceptable salts and esters thereof, or a combination thereof. In some cases, (a) can be applied in an amount of from 0.1 g ae/ha to 300 g ae/ha (e.g., from 0.5 g ae/ha, from 5 g ae/ha to 40 g ae ha) and/or (b) can be applied in an amount of from 5 g ae/ha to 3000 g ae/ha (e.g., from 5 g ae/ha to 1000 g ae/ha). In some cases, (a) and (b) can be applied in a weight ratio of from 1:8800 to 240:1 (e.g., from 1:3000 to 60:1, from 1:224 to 4:1, from 1:200 to 8:1, from 1:70 to 1:1, or from 1:56 to 1:1).

In some embodiments, (b) can comprise a semicarbazone herbicide. In certain embodiments, (b) can include diflufenzopyr or an agriculturally acceptable salt or ester thereof. In some cases, (a) can be applied in an amount of from 0.1 g ae/ha to 300 g ae/ha (e.g., from 0.5 g ae/ha, from 5 g ae/ha to 40 g ae/ha) and/or (b) can be applied in an amount of from 1 g ae/ha to 1000 g ae/ha (e.g., from 3.5 g ae/ha to 15 g ae/ha). In some cases, (a) and (b) can be applied in a weight ratio of from 1:2000 to 300:1 (e.g., 1:200 to 12:1, from 1:100 to 10:1, from 1:25 to 5:1, from 1:2 to 12:1, from 1:1 to 6:1, from 1:3.3 to 1:2, or from 1.25:1 to 5:1).

In some embodiments, (b) can comprise a phthalamate herbicide or other benzoic acid, agriculturally acceptable salts or esters thereof. In certain embodiments, (b) can include naptalam, 2,3,5-triiodobenzoic acid, or an agriculturally acceptable salt or ester thereof. In some cases, (a) can be applied in an amount of from 0.1 g ae/ha to 300 g ae/ha (e.g., from 0.5 g ae/ha, from 5 g ae/ha to 40 g ae/ha) and/or (b) can be applied in an amount of from 2000 g ae/ha to 5000 g ae/ha (e.g., from 2000 g ae/ha to 3500 g ae/ha). In some cases, (a) and (b) can be applied in a weight ratio of from 1:11000 to 1:6.7 (e.g., from 1:4000 to 1:18.3, from 1:2000 to 1:25, or from 1:1000 to 1:50).

The description below sets forth details of one or more embodiments of the present disclosure. Other features, objects, and advantages will be apparent from the description and from the claims.

DETAILED DESCRIPTION

The present disclosure relates to herbicidal compositions comprising a herbicidally effective amount of (a) a pyridine carboxylic acid herbicide or an agriculturally acceptable N-oxide, salt, or ester thereof, and (b) a synthetic auxin herbicide, an auxin transport inhibitor, agriculturally acceptable salts or esters thereof, or a combination thereof. The present disclosure also relates to methods for controlling undesirable vegetation.

I. Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the terms "herbicide" and "herbicidal active ingredient" refer to an active ingredient that kills, controls, or otherwise adversely modifies the growth of vegetation, particularly undesirable vegetation, such as weeds, when applied in an appropriate amount.

As used herein, a herbicidally effective amount" refers to an amount of an active ingredient that causes a "herbicidal effect," i.e., an adversely modifying effect including, for instance, a deviation from natural growth or development, killing, regulation, desiccation, growth inhibition, growth reduction, and retardation.

As used herein, applying a herbicide or herbicidal composition refers to delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, the terms "crops" and "vegetation" can include, for instance, dormant seeds, germinant seeds, emerging seedlings, plants emerging from vegetative propagules, immature vegetation, and established vegetation.

As used herein, immature vegetation refers to small vegetative plants prior to reproductive stage, and mature vegetation refers to vegetative plants during and after the reproductive stage.

As used herein, the term "acyl" refers to a group of formula —C(O)R, where R is hydrogen, alkyl (e.g., $C_1$-$C_{10}$ alkyl), haloalkyl ($C_1$-$C_8$ haloalkyl), alkenyl ($C_2$-$C_8$ alkenyl), haloalkenyl (e.g., $C_2$-$C_8$ haloalkenyl), alkynyl (e.g., $C_2$-$C_8$ alkynyl), alkoxy ($C_1$-$C_8$ alkoxy), haloalkoxy ($C_1$-$C_8$ alkoxy), aryl, or heteroaryl, arylalkyl ($C_7$-$C_{10}$ arylalkyl), as defined below, where "C(O)" or "CO" is short-hand notation for C=O. In some embodiments, the acyl group can be a $C_1$-$C_6$ acyl group (e.g., a formyl group, a $C_1$-$C_5$ alkylcarbonyl group, or a $C_1$-$C_5$ haloalkylcarbonyl group). In some embodiments, the acyl group can be a $C_1$-$C_3$ acyl group (e.g., a formyl group, a $C_1$-$C_3$ alkylcarbonyl group, or a $C_1$-$C_3$ haloalkylcarbonyl group).

As used herein, the term "alkyl" refers to saturated, straight-chained or branched saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) haloalkyl groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkenyl" refers to unsaturated, straight-chained, or branched hydrocarbon moieties containing a double bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=$CH_2$; 1-propenyl refers to a group with the structure —CH=CH—$CH_3$; and 2-propenyl refers to a group with the structure —$CH_2$—CH=$CH_2$. Alkenyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

The term "haloalkenyl," as used herein, refers to an alkenyl group, as defined above, which is substituted by one or more halogen atoms.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkoxy" refers to a group of the formula R—O—, where R is unsubstituted or substituted alkyl as defined above. Unless otherwise specified, alkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-dimethyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, the term "haloalkoxy" refers to a group of the formula R—O—, where R is unsubstituted or substituted haloalkyl as defined above. Unless otherwise specified, haloalkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, and 1,1,1-trifluoroprop-2-oxy.

As used herein, the term "alkylthio" refers to a group of the formula R—S—, where R is unsubstituted or substituted alkyl as defined above. Unless otherwise specified, alkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-do-methylpropylthio, 1-ethylpropylthio, hexylthio, 1,1-dimethylpropylthio, 1,2-dimethyl propylthio, 1-methylpentylthio, 2-methylpentylthio, 3-methylpentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, the term "haloalkylthio" refers to an alkylthio group as defined above wherein the carbon atoms are partially or entirely substituted with halogen atoms. Unless otherwise specified, haloalkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein, the term "alkylcarbonyl" refers to an unsubstituted or substituted alkyl group bonded to a carbonyl group, $C_1$-$C_3$ alkylcarbonyl and $C_1$-$C_3$ haloalkylcarbonyl refer to groups wherein a $C_1$-$C_3$ unsubstituted or substituted alkyl or haloalkyl group is bonded to a carbonyl group (the group contains a total of 2 to 4 carbon atoms).

As used herein, the term "alkoxycarbonyl" refers to a group of the formula

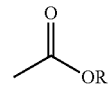

wherein R is unsubstituted or substituted alkyl.

As used herein, the term "arylalkyl" refers to an alkyl group substituted with an unsubstituted or substituted aryl group, $C_7$-$C_{10}$ arylalkyl refers to a group wherein the total number of carbon atoms in the group is 7 to 10, not including the carbon atoms present in any substituents of the aryl group.

As used herein, the term "alkylamino" refers to an amino group substituted with one or two unsubstituted or substituted alkyl groups, which may be the same or different.

As used herein, the term "haloalkylamino" refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ unsubstituted or substituted alkyl, and $C_1$-$C_6$ dialkylaminocarbonyl refers to a group of the formula $R_2NC(O)$— wherein each R is independently $C_1$-$C_6$ unsubstituted or substituted alkyl.

As used herein, the term "alkylcarbamyl" refers to a carbamyl group substituted on the nitrogen with an unsubstituted or substituted alkyl group.

As used herein, the term "alkylsulfonyl" refers to a group of the formula

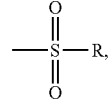

where R is unsubstituted or substituted alkyl.

As used herein, the term "carbamyl" (also referred to as carbamoyl and aminocarbonyl) refers to a group of the formula

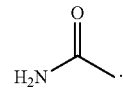

As used herein, the term "dialkylphosphonyl" refers to a group of the formula

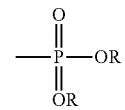

where R is independently unsubstituted or substituted alkyl in each occurrence.

As used herein, $C_1$-$C_6$ trialkylsilyl refers to a group of the formula —$SiR_3$ wherein each R is independently a $C_1$-$C_6$ unsubstituted or substituted alkyl group (the group contains a total of 3 to 18 carbon atoms).

As used herein, Me refers to a methyl group; OMe refers to a methoxy group; and i-Pr refers to an isopropyl group.

As used herein, the term "halogen" including derivative terms such as "halo" refers to fluorine, chlorine, bromine and iodine.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Compounds described herein can include N-oxides. Pyridine N-oxides can be obtained by oxidation of the corresponding pyridines. Suitable oxidation methods are described, for example, in Houben-Weyl, *Methoden der organischen Chemie* [*Methods in organic chemistry*], expanded and subsequent volumes to the 4th edition, volume E 7b, p. 565 f.

Pyridine Carboxylic Acid Herbicides

Compositions and methods of the present disclosure can include a pyridine carboxylic acid herbicide defined by Formula (I)

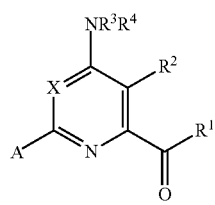

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups A1 to A36

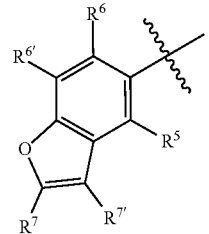

A1

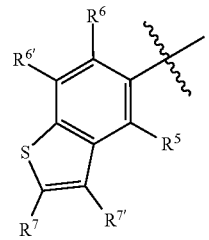

A2

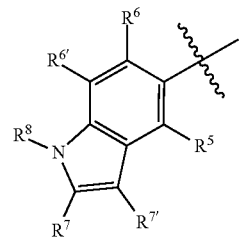

A3

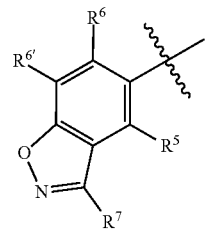

A4

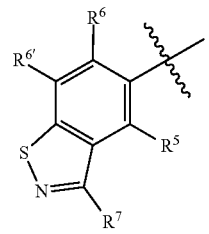

A5

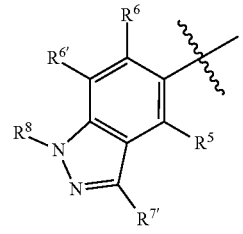

A6

-continued
A7
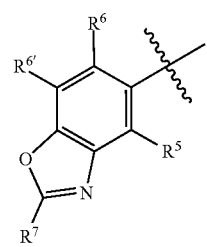
A8
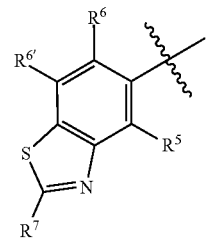
A9
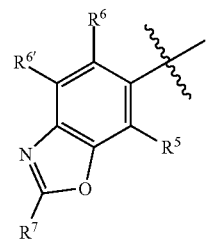
A10
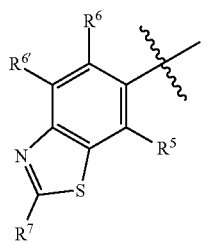
A11
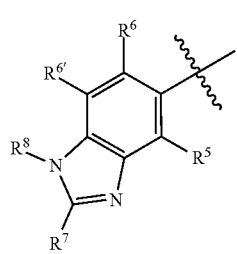
A12
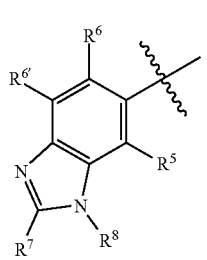
-continued
A13
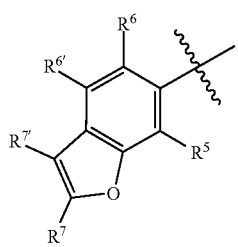
A14
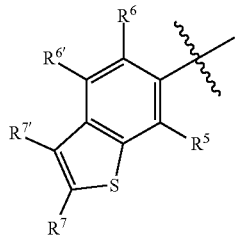
A15
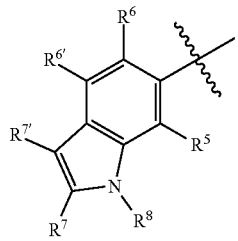
A16
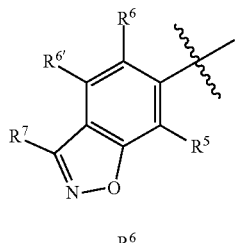
A17
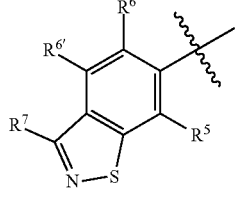
A18
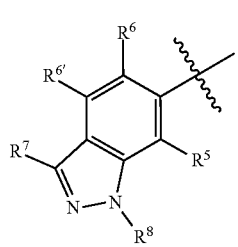
A19
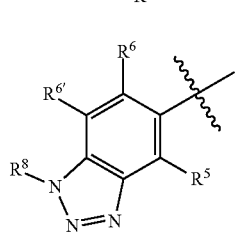

A20 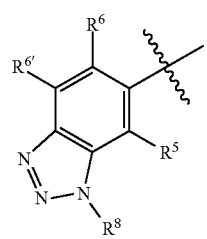
A21 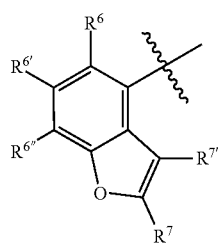
A22 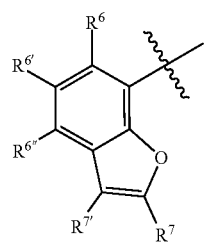
A23 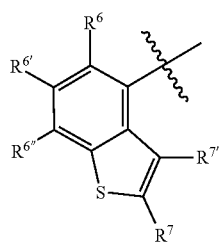
A24 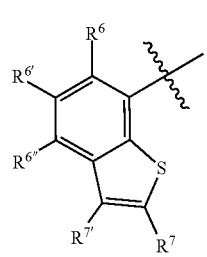
A25 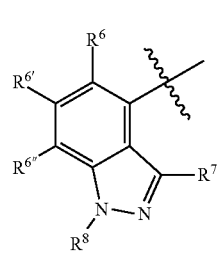
A26 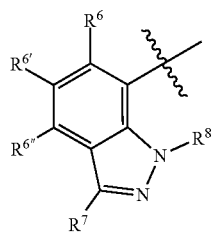
A27 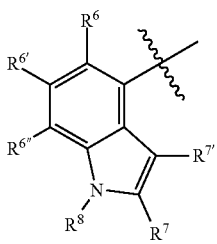
A28 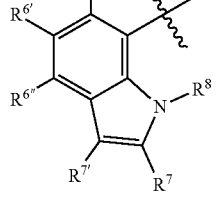
A29 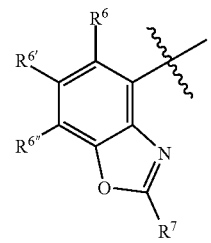
A30 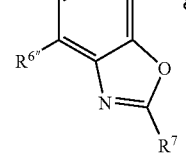
A31 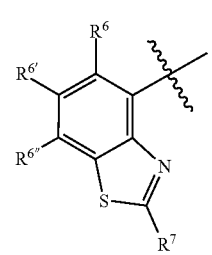

-continued

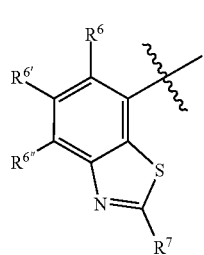
A32

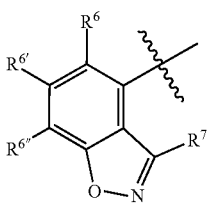
A33

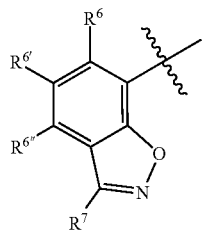
A34

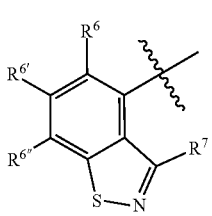
A35

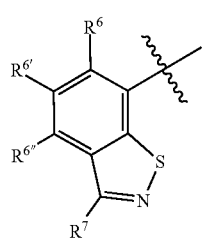
A36

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In some embodiments, $R^{1'}$ is hydrogen or $C_1$-$C_8$ alkyl. In some embodiments, $R^{1'}$ is hydrogen.

In some embodiments, $R^2$ is halogen, $C_1$-$C_4$ alkyl, $C_1$-$C_4$ haloalkyl, $C_2$-$C_4$ alkynyl, $C_2$-$C_4$-alkenyl, $C_2$-$C_4$ haloalkenyl, $C_1$-$C_4$-alkoxy, or $C_1$-$C_4$ haloalkoxy. In some embodiments, $R^2$ is halogen, $C_2$-$C_4$-alkenyl, $C_2$-$C_4$ haloalkenyl, or $C_1$-$C_4$-alkoxy. In some embodiments, $R^2$ is halogen. In some embodiments, $R^2$ is $C_2$-$C_4$-alkenyl or $C_2$-$C_4$ haloalkenyl. In some embodiments, $R^2$ is $C_1$-$C_4$ alkoxy. In some embodiments, $R^2$ is Cl, OMe, vinyl, or 1-propenyl. In some embodiments, $R^2$ is Cl. In some embodiments, $R^2$ is OMe. In some embodiments, $R^2$ is vinyl or 1-propenyl.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_1$-$C_6$ alkoxy or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, or $C_1$-$C_3$ haloalkylcarbonyl. In some embodiments, at least one of $R^3$ and $R^4$ are hydrogen. In some embodiments, $R^3$ and $R^4$ are both hydrogen.

In some embodiments, X is N, CH or CF. In some embodiments, X is N. In some embodiments, X is CH. In some embodiments, X is CF. In other embodiments, X is C—$CH_3$.

In some embodiments, A is A1, A2, A3, A4, A5, A6, A7, A8, A9, A10, A11, A12, A13, A14, A15, A16, A17, A18, A19, or A20. In other embodiments, A is one of A21, A22, A23, A24, A25, A26, A27, A28, A29, A30, A31, A32, A33, A34, A35, and A36.

In some embodiments, A is A1, A2, A3, A7, A8, A9, A10, A11, A12, A13, A14, or A15. In some embodiments, A is one of groups A1, A2, A3, A7, A8, A9, A10, A13, A14, and A15. In some embodiments, A is one of groups A1, A2, A3, A13, A14, and A15. In certain cases, A is A2, A3, A8, A13, or A15. In some embodiments, A is one of groups A13, A14, and A15. In some embodiments, A is A15.

In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, or amino. In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, or amino. In some embodiments, $R^5$ is hydrogen, halogen, $C_1$-$C_4$ alkyl or $C_1$-$C_4$ alkoxy. In some embodiments, $R^5$ is hydrogen or F. In some embodiments, $R^5$ is hydrogen. In other embodiments, $R^5$ is F.

In some embodiments, $R^6$ is hydrogen, halogen, $C_1$-$C_4$ alkyl, $C_1$-$C_4$ haloalkyl, $C_1$-$C_3$ alkoxy, or $C_1$-$C_3$ haloalkoxy. In some embodiments, $R^6$ is hydrogen or fluorine. In some embodiments, $R^6$ is hydrogen. In some embodiments, $R^6$ is fluorine.

In some embodiments, R$^{6'}$ is hydrogen or halogen. In some embodiments, R$^{6'}$ is hydrogen, F, or Cl. In some embodiments, R$^{6'}$ is hydrogen or F. In some embodiments, R$^{6'}$ is hydrogen.

In some embodiments, R$^{6''}$ is hydrogen, halogen, C$_1$-C$_4$ alkyl, C$_1$-C$_4$ haloalkyl, cyclopropyl, C$_2$-C$_4$ alkynyl, CN, or NO$_2$. In some embodiments, R$^{6''}$ is hydrogen. In some embodiments, R$^{6''}$ is halogen. In some embodiments, R$^{6''}$ is C$_1$-C$_4$ alkyl. In some embodiments, R$^{6''}$ is C$_1$-C$_4$ haloalkyl. In some embodiments, R$^{6''}$ is cyclopropyl. In some embodiments, R$^{6''}$ is C$_2$-C$_4$ alkynyl. In some embodiments, R$^{6''}$ is CN. In some embodiments, R$^{6''}$ is NO$_2$.

In some embodiments:
X is N, CH, CF, CCl, or CBr;
R$^1$ is OR$^{1'}$, wherein R$^{1'}$ is hydrogen or C$_1$-C$_4$ alkyl;
R$^2$ is chlorine;
R$^3$ and R$^4$ are hydrogen;
A is A1, A2, A3, A4, A5, A6, A7, A8, A9, A10, A11, A12, A13, A14, A15, A16, A17, A18, A19, or A20;
R$^5$ is hydrogen, halogen, OH, amino, CN, C$_1$-C$_3$ alkyl, C$_1$-C$_3$ alkoxy, C$_1$-C$_3$ alkylamino, or cyclopropyl;
R$^6$, R$^{6'}$, and R$^{6''}$ are independently hydrogen halogen, NH$_2$, CN, C$_1$-C$_3$ alkyl, C$_1$-C$_3$ alkoxy, cyclopropyl, or vinyl;
R$^7$ and R$^{7'}$ are independently hydrogen, halogen, C$_1$-C$_3$ alkyl, C$_1$-C$_3$ alkoxy, C$_1$-C$_3$ alkylthio, cyclopropyl, C$_1$-C$_3$ alkylamino, or phenyl; and
R$^8$ is hydrogen, C$_1$-C$_3$ alkyl, phenyl, or C$_1$-C$_3$ alkylcarbonyl.

In some embodiments, R$^2$ is halogen, C$_2$-C$_4$-alkenyl, C$_2$-C$_4$ haloalkenyl, or C$_1$-C$_4$-alkoxy; R$^3$ and R$^4$ are both hydrogen; and X is N, CH, or CF.

In some embodiments, R$^2$ is halogen; R$^3$ and R$^4$ are both hydrogen; and X is N, CH, or CF.

In some embodiments, R$^2$ is C$_2$-C$_4$-alkenyl or C$_2$-C$_4$ haloalkenyl; R$^3$ and R$^4$ are both hydrogen; and X is N, CH, or CF.

In some embodiments, R$^2$ is C$_1$-C$_4$-alkoxy; R$^3$ and R$^4$ are both hydrogen; and X is N, CH, or CF.

In some embodiments, R$^2$ is halogen, C$_2$-C$_4$-alkenyl, C$_2$-C$_4$ haloalkenyl, or C$_1$-C$_4$-alkoxy;
R$^3$ and R$^4$ are both hydrogen; X is N, CH, or CF; R$^5$ is hydrogen or F; R$^6$ is hydrogen or F; R$^{6'}$ is hydrogen; R$^{6''}$, if applicable to the relevant A group, is hydrogen or halogen; and R$^7$ and R$^{7'}$, if applicable to the relevant A group, are independently hydrogen or halogen.

In some embodiments, R$^2$ is halogen, C$_1$-C$_4$-alkoxy, or C$_2$-C$_4$-alkenyl; R$^3$ and R$^4$ are hydrogen; X is N, CH, or CF; and A is one of groups A1 to A20.

In some embodiments, R$^2$ is chlorine; R$^3$ and R$^4$ are hydrogen; X is N, CH, or CF; A is one of groups A1 to A20; R$^5$ is hydrogen or F; R$^6$ and R$^{6'}$ are independently hydrogen or F; and R$^7$ and R$^{7'}$, if applicable to the relevant A group, are independently hydrogen, halogen, C$_1$-C$_4$ alkyl, or C$_1$-C$_4$ haloalkyl.

In some embodiments, R$^2$ is chlorine, methoxy, vinyl, or 1-propenyl; R$^3$ and R$^4$ are hydrogen; and X is N, CH, or CF.

In some embodiments, R$^2$ is chlorine; R$^3$ and R$^4$ are hydrogen; and X is N, CH, or CF.

In some embodiments, R$^2$ is vinyl or 1-propenyl; R$^3$ and R$^4$ are hydrogen; and X is N, CH, or CF.

In some embodiments, R$^2$ is methoxy; R$^3$ and R$^4$ are hydrogen; and X is N, CH, or CF.

In some embodiments, R$^2$ is chlorine; R$^3$ and R$^4$ are hydrogen; and X is N.

In some embodiments, R$^2$ is chlorine; R$^3$ and R$^4$ are hydrogen; and X is CH.

In some embodiments, R$^2$ is chlorine; R$^3$ and R$^4$ are hydrogen; and X is CF.

In some embodiments, R$^2$ is chlorine; R$^1$ and R$^4$ are hydrogen; X is CF; A is one of A1, A2, A3, A7, A8, A9, A10, A13, A14, or A15; R$^5$ is F; and R$^6$ is H.

In some embodiments, R$^2$ is chlorine, methoxyl, vinyl, or 1-propenyl; R$^3$ and R$^4$ are hydrogen; X is N, CH, or CF; and A is one of A21 to A36.

In some embodiments, R$^2$ is chlorine, methoxy, vinyl, or 1-propenyl; R$^3$ and R$^4$ are hydrogen; X is CF; and A is one of

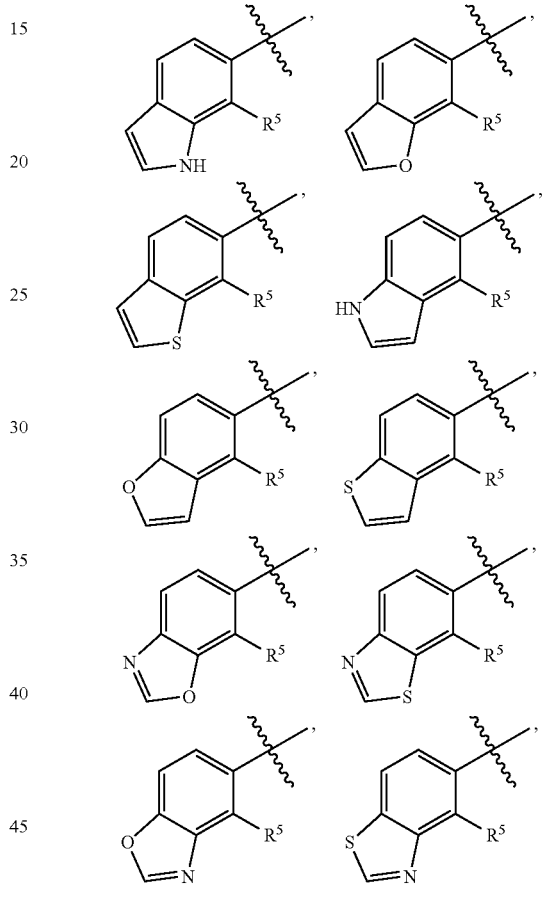

wherein R is hydrogen or F.

In some embodiments, R$^2$ is chlorine, methoxy, vinyl, or 1-propenyl; R$^3$ and R$^4$ are hydrogen; X is N, CH, or CF; and A is

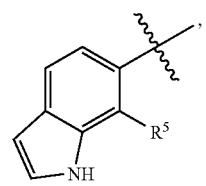

where R$^5$ is hydrogen or F.

In some embodiments, R$^2$ is chlorine, methoxy, vinyl, or 1-propenyl; R$^3$ and R$^4$ are hydrogen; X is N, CH, or CF; and A is

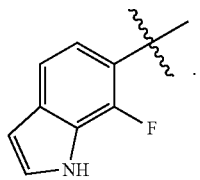 [SMILES: *c1ccc2cc[nH]c2c1F]

In some embodiments, $R^2$ is chlorine, methoxy, vinyl or 1-propenyl; $R^3$ and $R^4$ are hydrogen; X is CF; and A is

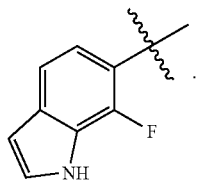 [SMILES: *c1ccc2cc[nH]c2c1F]

In some embodiments, the pyridine carboxylic acid herbicide can comprise a compound defined by Formula (I)

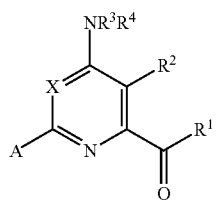

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_8$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

with the proviso that the pyridine carboxylic acid herbicide is not a compound defined by Formula (I)

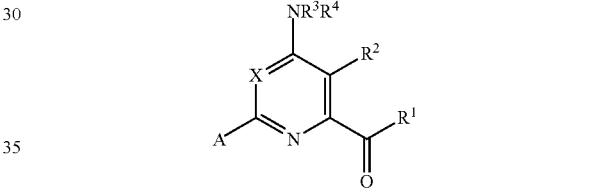

(I)

wherein

X is N, CH, CF, CCl, or CBr;

$R^1$ is $OR^{1'}$, wherein $R^{1'}$ is hydrogen or $C_1$-$C_4$ alkyl;

$R^2$ is chlorine;

$R^3$ and $R^4$ are hydrogen;

A is A1, A2, A3, A4, A5, A6, A7, A8, A9, A10, A11, A12, A13, A14, A15, A16, A17, A18, A19, or A20;

$R^5$ is hydrogen, halogen, OH, amino, CN, $C_1$-$C_3$ alkyl, $C_1$-$C_3$ alkoxy, $C_1$-$C_3$ alkylamino, or cyclopropyl;

$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;

$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and $R^8$ is hydrogen, $C_1$-$C_3$ alkyl, phenyl, or $C_1$-$C_3$ alkylcarbonyl;

or an agriculturally acceptable N-oxide or salt thereof.

In some of these embodiments, $R^1$ is $OR^1$. In some of these embodiments, X is CF. In some of these embodiments, A is A15. In some of these embodiments, $R^5$ is F.

In some embodiments:

X is CY, wherein Y is $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1''}$ or $NR^{1''}R^{1'''}$, wherein $R^{1''}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_8$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36:

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_8$ haloalkylthio;

$R^1$ is $OR^{1'}$ or $NR^{1''}R^{1'''}$, wherein $R^{1'}$ is $C_5$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_8$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is F, Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A6, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^{1'}$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl,
$C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_1$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently $C_1$-$C_4$ alkyl, $C_1$-$C_4$ haloalkyl, halocyclopropyl, $C_3$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino or $C_2$-$C_4$ haloalkylamino, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A4, A15, A16, A17, or A18;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ haloalkylthio, amino, $C_1$-$C_4$ alkylamino, or $C_2$-$C_4$ haloalkylamino; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1'''}$ and $R^{1''''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^1$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A3, A6, A11, A12, A15, A18, A19, or A20;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_8$ alkylthio, $C_1$-$C_3$ haloalkylthio, amino, $C_1$-$C_4$ alkylamino, $C_2$-$C_4$ haloalkylamino, or phenyl; and $R^8$ is $C_3$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, or $C_1$-$C_6$ trialkylsilyl.

In some of these embodiments, $R^1$ is $OR^1$. In some of these embodiments, X is CF. In some of these embodiments, A is A15. In some of these embodiments, $R^5$ is F.

In certain embodiments, the pyridine carboxylic acid herbicide can comprise a compound defined by Formula (II):

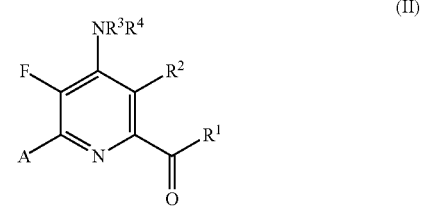

(II)

wherein $R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments:

$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio.

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

A is A1, A2, A3, A7, A8, A9, A10, A11, A12, A13, A14, A15, A21, A22, A23, A24, A27, A28, A29, A30, A31, or A32;

$R^5$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, $R^1$ is $OR^{1'}$, wherein $R^{1'}$ is hydrogen, $C_1$-$C_8$ alkyl, or $C_7$-$C_{10}$ arylalkyl.

In some embodiments, $R^2$ is halogen, $C_2$-$C_4$-alkenyl, $C_2$-$C_4$ haloalkenyl, or $C_1$-$C_4$-alkoxy.

In certain embodiments, $R^2$ is Cl, methoxy, vinyl, or 1-propenyl. In some embodiments, $R^3$ and $R^4$ are hydrogen.

In some embodiments, A is A1, A2, A3, A7, A8, A9, A10, A13, A14, or A15. In some embodiments, A is A1, A2, A3, A7, A8, A9, A10, A11, A13, A14, or A15. In some embodiments, A is A1, A2, A3, A7, A8, A9, A10, A13, A14, or A15. In certain embodiments, A is A2, A3, A8, A13, or A15. In certain embodiments, A is A1, A2, A3, A13, A14, or A15. In certain embodiments, A is A15.

In some embodiments, $R^5$ is hydrogen or F. In certain embodiments, $R^5$ is F. In certain embodiments, $R^5$ is H.

In some embodiments, $R^6$ is hydrogen or F. In certain embodiments, $R^6$ is F. In certain embodiments, $R^6$ is H. In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$, $R^{6'}$, and $R^{6''}$ are all hydrogen.

In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

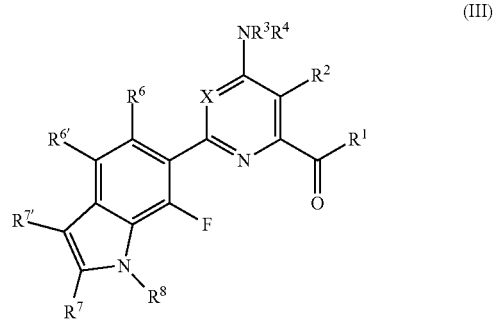

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$— $SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ $(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments:

X is N, CH, CF, CCl, or CBr;

$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio.

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, X is N, CH or CF. In some embodiments, X is N. In some embodiments, X is CH. In some embodiments, X is CF. In other embodiments, X is C—$CH_3$.

In some embodiments, $R^2$ is halogen, $C_2$-$C_4$-alkenyl, $C_2$-$C_4$ haloalkenyl, or $C_1$-$C_4$-alkoxy. In certain embodiments, $R^2$ is Cl, methoxy, vinyl, or 1-propenyl. In some embodiments, $R^3$ and $R^4$ are hydrogen.

In some embodiments, $R^6$ is hydrogen or F. In certain embodiments, $R^6$ is F. In certain embodiments, $R^6$ is H. In some embodiments, $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$ and $R^{6'}$ are both hydrogen.

In certain embodiments, $R^7$ and $R^{7'}$ are both hydrogen.

In certain embodiments, $R^6$, $R^{6'}$, $R^7$, and $R^{7'}$ are all hydrogen.

In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (IV):

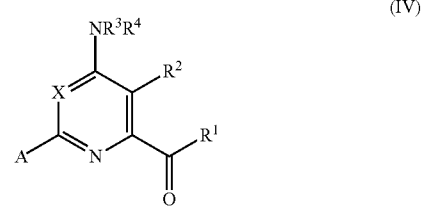

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, F, Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^3$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, X is N, CH or CF. In some embodiments, X is N. In some embodiments, X is CH. In some embodiments, X is CF. In other embodiments, X is C—$CH_3$.

In some embodiments, $R^2$ is $C_2$-$C_4$-alkenyl, $C_2$-$C_4$ haloalkenyl, or $C_1$-$C_4$-alkoxy. In certain embodiments, $R^2$ is methoxy, vinyl, 1-fluorovinyl, or 1-propenyl. In some embodiments, $R^3$ and $R^4$ are hydrogen.

In some embodiments, A is A1, A2, A3, A7, A8, A9, A10, A13, A14, or A15. In some embodiments, A is A1, A2, A3, A7, A8, A9, A10, A11, A13, A14, or A15. In some embodiments, A is A1, A2, A3, A7, A8, A9, A10, A13, A14, or A15. In certain embodiments, A is A2, A3, A8, A13, or A15. In certain embodiments, A is A1, A2, A3, A13, A14, or A15. In certain embodiments, A is A15.

In some embodiments, $R^5$ is hydrogen or F. In certain embodiments, $R^5$ is F. In certain embodiments, $R^5$ is H.

In some embodiments, $R^6$ is hydrogen or F. In certain embodiments, $R^6$ is F. In certain embodiments, $R^6$ is H. In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$, $R^{6'}$, and $R^{6''}$ are all hydrogen.

In certain embodiments, the pyridine carboxylic acid herbicide can comprise one of Compounds 1-24, the structures of which are shown in the table below.

| Compound No. | Structure |
|---|---|
| 1 | |
| 2 | |
| 3 | |
| 4 | 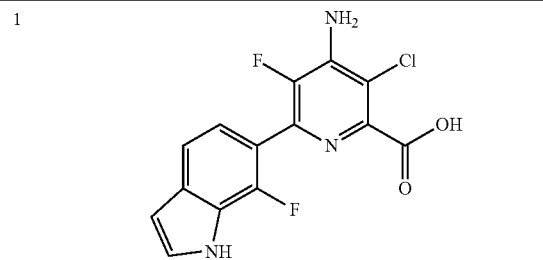 |
| 5 | 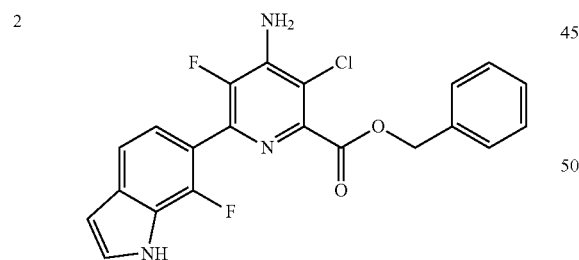 |
| 6 | 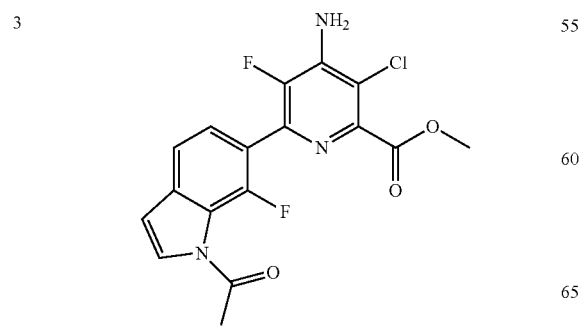 |
| 7 | 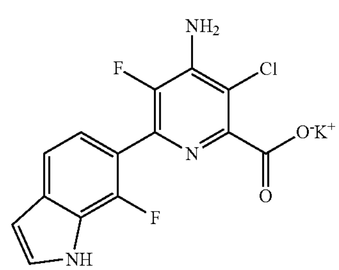 |

| Compound No. | Structure |
|---|---|
| 8 | 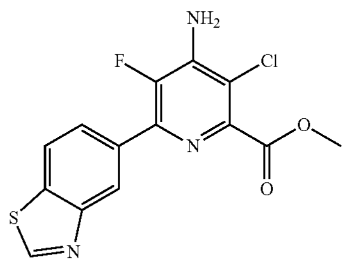 [SMILES: COC(=O)c1nc(-c2ccc3scnc3c2)c(F)c(N)c1Cl] |
| 9 | 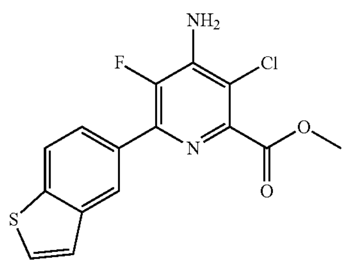 [SMILES: COC(=O)c1nc(-c2ccc3sccc3c2)c(F)c(N)c1Cl] |
| 10 | 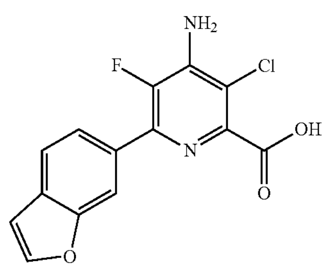 [SMILES: Nc1c(F)c(-c2ccc3ccoc3c2)nc(C(=O)O)c1Cl] |
| 11 | 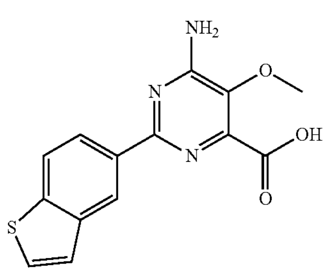 [SMILES: COc1c(N)nc(-c2ccc3sccc3c2)nc1C(=O)O] |
| 12 | 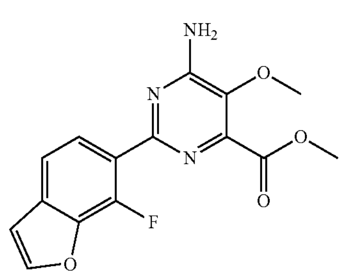 [SMILES: COC(=O)c1nc(-c2ccc3ccoc3c2F)nc(N)c1OC] |
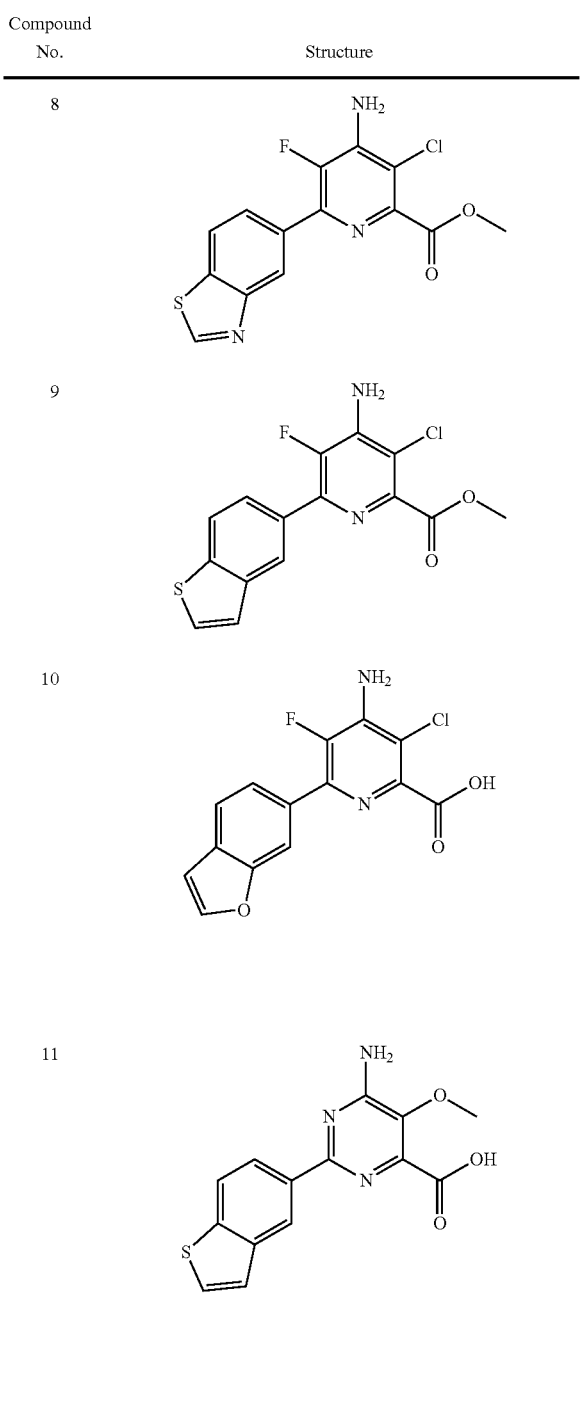
| Compound No. | Structure |
|---|---|
| 13 | 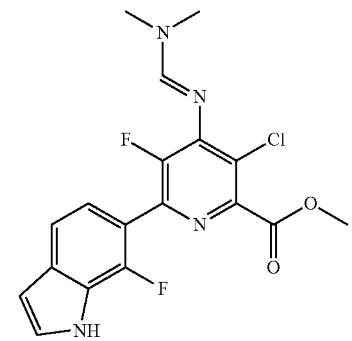 [SMILES: COC(=O)c1nc(-c2ccc3cc[nH]c3c2F)c(F)c(/N=C/N(C)C)c1Cl] |
| 14 | 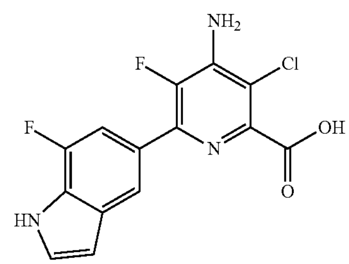 [SMILES: Nc1c(F)c(-c2cc(F)c3[nH]ccc3c2)nc(C(=O)O)c1Cl] |
| 15 | 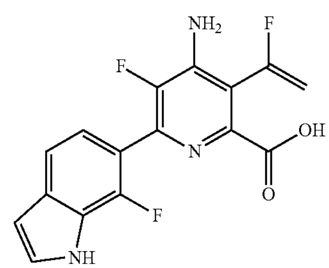 [SMILES: C=C(F)c1c(C(=O)O)nc(-c2ccc3cc[nH]c3c2F)c(F)c1N] |
| 16 | 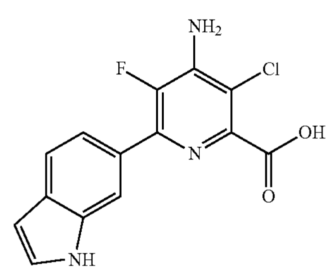 [SMILES: Nc1c(F)c(-c2ccc3cc[nH]c3c2)nc(C(=O)O)c1Cl] |
| 17 | 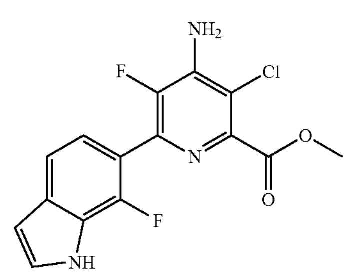 [SMILES: COC(=O)c1nc(-c2ccc3cc[nH]c3c2F)c(F)c(N)c1Cl] |
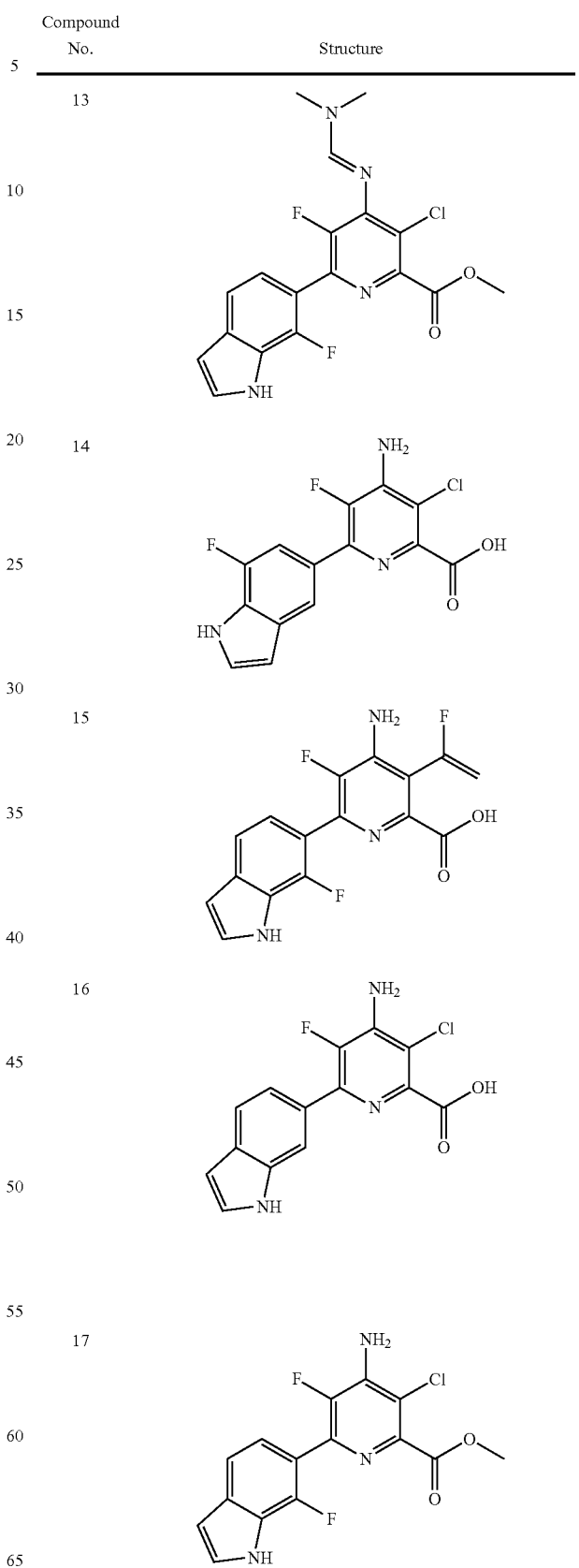

| Compound No. | Structure |
|---|---|
| 18 | (4-amino-3-chloro-5-fluoro-6-(7-fluoro-1H-indol-6-yl)picolinic acid butyl ester) |
| 19 | (methyl 3-chloro-5-fluoro-6-(7-fluoro-1H-indol-6-yl)-4-((methoxymethylene)amino)picolinate) |
| 20 | (methyl 4-amino-5-fluoro-6-(7-fluoro-1H-indol-6-yl)-3-methoxypicolinate) |
| 21 | (4-amino-5-fluoro-6-(7-fluoro-1H-indol-6-yl)-3-methoxypicolinic acid) |
| 22 | (methyl 4-amino-5-fluoro-6-(7-fluoro-1H-indol-6-yl)-3-vinylpicolinate) |
| 23 | (4-amino-3-chloro-6-(7-fluoro-1H-indol-6-yl)picolinic acid) |
| 24 | (4-amino-3-chloro-6-(benzothiazol-6-yl)-5-fluoropicolinic acid) |

In certain embodiments, the pyridine carboxylic acid herbicide can comprise 4-amino-3-chloro-5-fluoro-6-(7-fluoro-1H-indol-6-yl) picolinic acid, or an agriculturally acceptable N-oxide, salt, or ester thereof.

In some embodiments, the pyridine carboxylic acid herbicide can be provided as an agriculturally acceptable salt. Exemplary agriculturally acceptable salts of the pyridine carboxylic acid herbicides of Formula (I) include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, diglycolamine salts, choline salts, and quaternary ammonium salts such as those represented by the formula $R^9R^{10}R^{11}R^{12}N^+$ and wherein $R^9$, $R^{10}$, $R^{11}$ and $R^{12}$ (e.g., $R^9$-$R^{12}$) each independently can represent hydrogen, $C_1$-$C_{10}$ alkyl, $C_2$-$C_8$ alkenyl, $C_2$-$C_8$ alkynyl, $C_1$-$C_8$ alkoxy, $C_1$-$C_8$ alkylthio, or aryl groups, provided that $R^9$-$R^{12}$ are sterically compatible.

In some embodiments, the pyridine carboxylic acid herbicide can be provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl, butoxyethyl esters, substituted or unsubstituted aryl esters, orthoesters, substituted or unsubstituted alkylaryl esters, and substituted or unsubstituted arylalkyl esters. In some embodiments, the ester can comprise a $C_1$-$C_8$ alkyl ester, wherein the $C_1$-$C_8$ alkyl group is optionally substituted with one or more moieties selected from the group consisting of cyano, $C_2$-$C_8$ alkoxy, and $C_2$-$C_8$ alkylsulfonyl. For example, the ester can comprise a methyl, —$CH_2CN$, —$CH_2OCH_3$, —$CH_2OCH_2CH_2OCH_3$, or —$CH_2CH_2SO_2CH_3$ ester.

The ester can also be an acetal (e.g., a cyclic acetal) formed by protection of the carbonyl group in the pyridine carboxylic acid herbicides described above (e.g., by Formula (I)). For example, the pyridine carboxylic acid herbicides described above can be reacted with a suitable diol (e.g., a diol such as ethane-1,2-diol or butane-2,3-diol, for example, using standard protecting group chemistry, such as taught in Greene, et al., *Protective Groups in Organic Synthesis*, John Wiley and Sons, Fourth Edition, 2007, hereby incorporated by reference) to form a cyclic acetal. In one embodiment, the ester can be a cyclic acetal defined by the structure below, where $R^2$, $R^3$, $R^4$, X, and A are as described above.

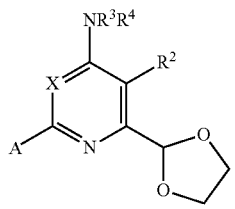

In some embodiments, the ester can comprise a substituted or unsubstituted benzyl ester. In some embodiments, the ester can comprise a benzyl ester optionally substituted with one or more moieties selected from the group consisting of halogen, $C_1$-$C_2$ alkyl, $C_1$-$C_2$ haloalkyl, and combinations thereof. In some embodiments, the ester can comprise a methyl ester.

The pyridine carboxylic acid herbicide, or an agriculturally acceptable N-oxide, salt, or ester thereof, can be applied to vegetation or an area adjacent the vegetation or applied to soil or water to prevent the emergence or growth of vegetation in an amount sufficient to induce a herbicidal effect. In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of 0.1 grams of acid equivalent per hectare (g ae/ha) or greater (e.g., 0.2 g ae/ha or greater, 0.3 g ae/ha or greater, 0.4 g ae/ha or greater, 0.5 g ae/ha or greater, 0.6 g ae/ha or greater, 0.7 g ae/ha or greater, 0.8 g ae/ha or greater, 0.9 g ae/ha or greater, 1 g ae/ha or greater, 1.1 g ae/ha or greater, 1.2 g ae/ha or greater, 1.3 g ae/ha or greater, 1.4 g ae/ha or greater, 1.5 g ae/ha or greater, 1.6 g ae/ha or greater, 1.7 g ae/ha or greater, 1.8 g ae/ha or greater, 1.9 g ae/ha or greater, 2 g ae/ha or greater, 2.25 g ae/ha or greater, 2.5 g ae/ha or greater, 2.75 g ae/ha or greater, 3 g ae/ha or greater, 4 g ae/ha or greater, 5 g ae/ha or greater, 6 g ae/ha or greater, 7 g ae/ha or greater, 8 g ae/ha or greater, 9 g ae/ha or greater, 10 g ae/ha or greater, 11 g ae/ha or greater, 12 g ae/ha or greater, 13 g ae/ha or greater, 14 g ae/ha or greater, 15 g ae/ha or greater, 16 g ae/ha or greater, 17 g ae/ha or greater, 18 g ae/ha or greater, 19 g ae/ha or greater, 20 g ae/ha or greater, 21 g ae/ha or greater, 22 g ae/ha or greater, 23 g ae/ha or greater, 24 g ae/ha or greater, 25 g ae/ha or greater, 26 g ae/ha or greater, 27 g ae/ha or greater, 28 g ae/ha or greater, 29 g ae/ha or greater, 30 g ae/ha or greater, 31 g ae/ha or greater, 32 g ae/ha or greater, 33 g ae/ha or greater, 34 g ae/ha or greater, 35 g ae/ha or greater, 36 g ae/ha or greater, 37 g ae/ha or greater, 38 g ae/ha or greater, 39 g ae/ha or greater, 40 g ae/ha or greater, 41 g ae/ha or greater, 42 g ae/ha or greater, 43 g ae/ha or greater, 44 g ae/ha or greater, 45 g ae/ha or greater, 46 g ae/ha or greater, 47 g ae/ha or greater, 48 g ae/ha or greater, 49 g ae/ha or greater, 50 g ae/ha or greater, 55 g ae/ha or greater, 60 g ae/ha or greater, 65 g ae/ha or greater, 70 g ae/ha or greater, 75 g a/ha or greater, 80 g ae/ha or greater, 85 g ae/ha or greater, 90 g ae/ha or greater, 95 g ae/ha or greater, 100 g ae/ha or greater, 110 g ae/ha or greater, 120 g ae/ha or greater, 130 g ae/ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, or 290 g ae/ha or greater).

In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of 300 g ae/ha or less (e.g., 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 49 g ae/ha or less, 48 g ae/ha or less, 47 g ae/ha or less, 46 g ae/ha or less, 45 g ae/ha or less, 44 g ae/ha or less, 43 g ae/ha or less, 42 g ae/ha or less, 41 g ae/ha or less, 40 g ae/ha or less, 39 g ae/ha or less, 38 g ae/ha or less, 37 g ae/ha or less, 36 g ae/ha or less, 35 g ae/ha or less, 34 g ae/ha or less, 33 g ae/ha or less, 32 g ae/ha or less, 31 g ae/ha or less, 30 g ae/ha or less, 29 g ae/ha or less, 28 g ae/ha or less, 27 g ae/ha or less, 26 g ae/ha or less, 25 g ae/ha or less, 24 g ae/ha or less, 23 g ae/ha or less, 22 g ae/ha or less, 21 g ae/ha or less, 20 g ae/ha or less, 19 g ae/ha or less, 18 g ae/ha or less, 17 g ae/ha or less, 16 g ae/ha or less, 15 g ae/ha or less, 14 g ae/ha or less, 13 g ae/ha or less, 12 g ae/ha or less, 11 g ae/ha or less, 10 g ae/ha or less, 9 g ae/ha or less, 8 g ae/ha or less, 7 g ae/ha or less, 6 g ae/ha or less, 5 g ae/ha or less, 4 g ae/ha or less, 3 g ae/ha or less, 2.75 g ae/ha or less, 2.5 g ae/ha or less, 2.25 g ae/ha or less, 2 g ae/ha or less, 1.9 g ae/ha or less, 1.8 g ae/ha or less, 1.7 g ae/ha or less, 1.6 g ae/ha or less, 1.5 g ae/ha or less, 1.4 g ae/ha or less, 1.3 g ae/ha or less, 1.2 g ae/ha or less, 1.1 g ae/ha or less, 1 g ae/ha or less, 0.9 g ae/ha or less, 0.8 g ae/ha or less, 0.7 g ae/ha or less, 0.6 g ae/ha or less, 0.5 g ae/ha or less, 0.4 g ae/ha or less, 0.3 g ae/ha or less, or 0.2 g ae/ha or less).

The pyridine carboxylic acid herbicide, or an agriculturally acceptable N-oxide, salt, or ester thereof, can be applied to vegetation or an area adjacent the vegetation or applied to soil or water to prevent the emergence or growth of vegetation in an amount ranging from any of the minimum values described above to any of the maximum values described above. In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of from 0.1-300 g ae/ha (e.g., from 0.5-300 g ae/ha, from 0.5-5 g ae/ha, from 0.1-5 g ae ha, from 2.5-40 g ae/ha, from 0.1-40 g ae/ha, from 0.5-40 g ae/ha, from 0.1-2.5 g ae/ha, from 0.5-2.5 g ae/ha, from 2-150 g ae/ha, from 5-75 g ae/ha, from 5-40 g ae/ha, from 30-40 g ae/ha, or from 5-15 g ae/ha). In some embodiments, the pyridine carboxylic acid herbicide, or an agriculturally acceptable N-oxide, salt, or ester thereof, is applied in an amount from 5-15 g ae/ha. In some embodiments, the pyridine carboxylic acid herbicide, or an agriculturally acceptable N-oxide, salt, or ester thereof, is applied in an amount from 5-40 g ae/ha.

Synthetic Auxin Herbicides

In addition to a pyridine carboxylic acid herbicide or agriculturally acceptable N-oxide, salt or ester thereof, the compositions can include a synthetic auxin herbicide. Synthetic auxin herbicides mimic natural plant hormones and can inhibit cell division and growth. Synthetic auxin herbicides include phenoxy herbicides, benzoic acid herbicides, and carboxylic acid herbicides.

In some embodiments, the composition can include a synthetic auxin herbicide selected from the group consisting of 4-CPA; 4-CPB; 4-CPP; 2,4-D, 2,4-DB; 3,4-DA; 3,4-DB; 3,4-DP; 2,4-DEP; 2,4-DEB; 2,4,5-T; 2,4,5-TB; 2,3,6-TBA, aminocyclopyrachlor, aminopyralid, clopyralid, dichlorprop, dichlorprop-P, dicamba, difenopenten, disul, diclofop, erbon, etnipromid, fenoprop, fluoxypyr, fluorxypyr-MHE, mecoprop, mecoprop-P, MCPA, MCPA-thioethyl, MCPB, naphthaleneacetamide, α-naphthaleneacetic acids, 1-naphthol, naphthoxyacetic acids, potassium naphthenate, picloram, quinclorac, quinmerac, sodium naphthenate, 4-aminopicolinic acid based herbicides, such as halauxifen, halauxifen-methyl, 4-amino-3-chloro-6-(4-chloro-2-fluoro-3-methoxyphenyl)-5-fluoro-2-pyridinecarboxylic acid, benzyl 4-amino-3-chloro-6-(4-chloro-2-fluoro-3-methoxyphenyl)-5-fluoro-2-pyridinecarboxylate, and those described in U.S. Pat. Nos. 7,314,849 and 7,432,227 to Balko, et al., agriculturally acceptable salts and esters thereof, and combinations thereof. In some embodiments, the synthetic auxin herbicide can comprise 2,4-D, MCPA, dichlorprop, mecoprop, dicamba, clopyralid, fluroxypyr, halauxifen, agriculturally acceptable salts and esters thereof, or combinations thereof. In some embodiments, the synthetic auxin herbicide can comprise 2,4-DB, aminocyclopyrachlor, aminopyralid, picloram, quinclorac, triclopyr, 4-amino-3-chloro-6-(4-chloro-2-fluoro-3-methoxyphenyl)-5-fluoro-2-pyridinecarboxylic acid, benzyl 4-amino-3-chloro-6-(4-chloro-2-fluoro-3-methoxyphenyl)-5-fluoro-2-pyridinecarboxylate, agriculturally acceptable salts and esters thereof, or combinations thereof.

2,4-D

In certain embodiments, the synthetic auxin herbicide can comprise 2,4-D or an agriculturally acceptable salt or ester thereof. 2,4-D, shown below, is a phenoxyacetic acid herbicide that provides broad spectrum control of many annual, biannual and perennial broad-leaved weeds and aquatic broad-leaved weeds in cereals, maize, sorghum, grasslands, established turf, grass seed crops, orchards (pome fruit and stone fruit), cranberries, asparagus, sugar cane, rice, forestry, and on non-crop land (including areas adjacent to water), 2,4-D, as well as methods of preparing 2,4-D, are known in the art. Its herbicidal activity is described, for example, in The Pesticide Manual, Sixteenth Edition, 2012.

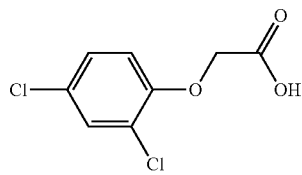 [SMILES: O=C(O)COc1ccc(Cl)cc1Cl]

In some embodiments, 2,4-D can be provided as an agriculturally acceptable salt or ester of 2,4-D. Exemplary agriculturally acceptable salts and esters of 2,4-D include, but are not limited to, 2,4-D-ammonium 2,4-D-butotyl, 2,4-D-2-butoxypropyl, 2,4-D-3-butoxypropyl, 2,4-D-butyl, 2,4-D choline, 2,4-D-diethylammonium, 2,4-D-dimethylammonium (2,4-D DMA), 2,4-D-diolamine, 2,4-D-dodecylammonium, 2,4-D-ethyl, 2,4-D-2-ethylhexyl (2,4-D EHE), 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, and clacyfos. In some embodiments, the 2,4-D can be provided as 2,4-D-2-ethyllhexyl (2,4-D EHE), shown below.

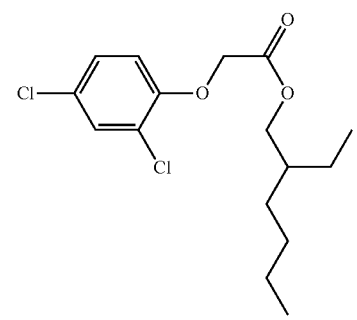 [SMILES: CCCCC(CC)COC(=O)COc1ccc(Cl)cc1Cl]

In some embodiments, 2,4-D can be provided as 2,4-D DMA, shown below.

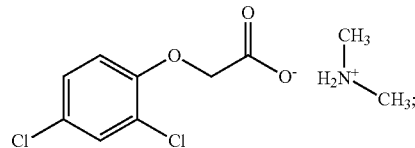

In some embodiments, the 2,4-D can be provided as 2,4-D choline, shown below.

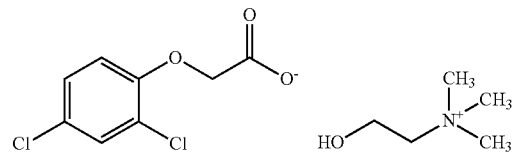

Exemplary uses of 2,4-D-choline include, but are not limited to, controlling annual and perennial broadleaf weeds, including, but not limited to, glyphosate-resistant broadleaf weeds, 2,4-D-Choline can be used in crops that have been made tolerant to 2,4-D, including, but not limited to, 2,4-D-tolerant soybeans, corn, and cotton, 2,4-D-Choline is generally, but is not required to be, applied post-emergent, 2,4-D-Choline can also be used for weed control in non-crop and perennial cropping systems.

MCPA

In certain embodiments, the synthetic auxin herbicide can comprise MCPA or an agriculturally acceptable salt or ester thereof. MCPA, shown below, is a phenoxyacetic acid herbicide that provides broad-spectrum control of many annual, biannual, and perennial broad-leaved weeds, woody weeds, and aquatic broad-leaved weeds in cereals, herbage seed crops, flax, rice, vines, peas, potatoes, asparagus, grassland, turf, under fruit trees, forestry, and on roadside verges and embankments. MCPA, as well as methods of preparing MCPA, are known in the art. Its herbicidal activity is described, for example, in The Pesticide Manual, Sixteenth Edition, 2012.

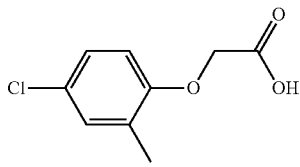

In some embodiments, MCPA can be provided as an agriculturally acceptable salt or ester of MCPA. Exemplary agriculturally acceptable salts of MCPA include, but are not limited to, MCPA-butotyl, MCPA-butyl, MCPA-dimethylammonium, MCPA-diolamine, MCPA-ethyl, MCPA-2-ethylhexyl (MCPA EHE), MCPA-isobutyl, MCPA-isoctyl, MCPA-isopropyl, MCPA-methyl, MCPA-olamine, MCPA-potassium, MCPA-sodium, MCPA-trolamine. In some embodiments, the MCPA can be provided as MCPA-2-ethylhexyl (MCPA EHE), shown below.

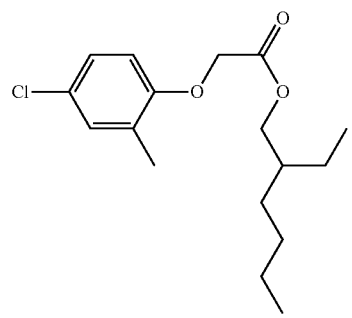 [SMILES: CCCCC(CC)COC(=O)COc1ccc(Cl)cc1C]

Dichlorprop

In certain embodiments, the synthetic auxin herbicide can comprise dichlorprop or an agriculturally acceptable salt or ester thereof. Dichlorprop, shown below, is a phenoxypropionic herbicide that provides broad-spectrum control of annual and perennial broad-leaved weeds in cereals and grasslands; brush control in non-crop land; control of broad-leaved aquatic weeds; and maintenance of embankments and roadside verges. Dichlorprop, as well as methods of making dichlorprop, are known in the art. Its herbicidal activity is described, for example, in The Pesticide Manual, Sixteenth Edition, 2012.

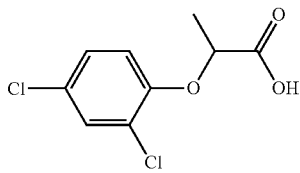

In some embodiments, dichlorprop can be provided as an agriculturally acceptable salt or ester of dichlorprop. Exemplary agriculturally acceptable salts and esters of dichlorprop include, but are not limited to, dichlorprop-butotyl, dichlorprop-dimethylammonium, dichlorprop-ethylammonium, dichlorprop-2-ethylhexyl, dichlorprop-isoctyl, dichlorprop-methyl, dichlorprop-potassium, dichlorprop-sodium, dichlorprop-P, dichlorprop-P-dimethylammonium, dichlorprop-P-2-ethylhexyl, dichlorprop-P-potassium, and dichlorprop-P-sodium. In some embodiments, the dichlorprop can be provided as dichlorprop-P, shown below.

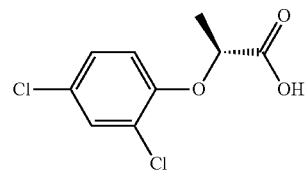

Mecoprop

In certain embodiments, the synthetic auxin herbicide can comprise mecoprop or an agriculturally acceptable salt or ester thereof. Mecoprop, shown below, is a phenoxy carboxylic acid herbicide that provides broad-spectrum control of broad-leaved weeds in wheat, barley, oats, herbage seed crops, grassland, and under fruit trees and vines. Mecoprop also provides control of docks (*Rumex* spp.) in meadows and pastures. Mecoprop, as well as methods of making mecoprop, are known in the art. Its herbicidal activity is described in The Pesticide Manual, Sixteenth Edition, 2012.

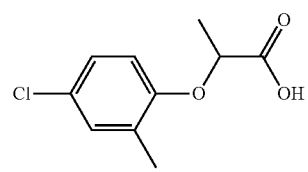

In some embodiments, mecoprop can be provided as an agriculturally acceptable salt or ester of mecoprop. Exemplary agriculturally acceptable salts and esters of mecoprop include, but are not limited to, mecoprop-butotyl, mecoprop-potassium, mecoprop-sodium, mecoprop-dimethylammonium, mecoprop-diolamine, mecoprop-ethadyl, mecoprop-2-ethylhexyl, mecoprop-isoctyl, mecoprop-methyl, mecoprop-trolamine, mecoprop-P, mecoprop-P-butotyl, mecoprop-P-dimethylammonium, mecoprop-P-ethylhexyl, and mecoprop-P-potassium. In some embodiments, the mecoprop can be provided as mecoprop-P, shown below.

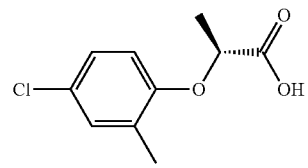

2,4-DB

In certain embodiments, the synthetic auxin herbicide can comprise 2,4-DB is a phenoxycarboxylic acid herbicide that provides post-emergence control of many annual and perennial broadleaf weeds in alfalfa, clovers, cereals and undersown cereals, grassland, forage legumes, soybeans, and peanuts. 2,4-DB, as well as methods of making 2,4-DB, are known in the art. Its herbicidal activity is described in *The Pesticide Manual*, Sixteenth Edition, 2012.

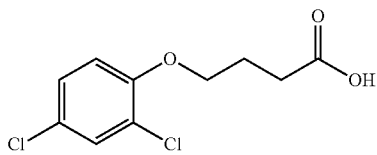 [SMILES: O=C(O)CCCOc1ccc(Cl)cc1Cl]

In some embodiments, 2,4-DB can be provided as an agriculturally acceptable salt or ester of 2,4-D. Exemplary agriculturally acceptable salts and esters of 2,4-DB include, but are not limited to, 2,4-DB-butyl, 2,4-DB-dimethylammonium (2,4-DB DMA), 2,4-DB-isoctyl, 2,4-DB-potassium, and 2,4-DB-sodium.

The synthetic auxin herbicide (e.g., 2,4-D, 2,4-DB, MCPA, dichlorprop, or mecoprop) or an agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the synthetic auxin herbicide or agriculturally acceptable salt or ester thereof is applied to vegetation or an area adjacent the vegetation or applied to soil or water to prevent the emergence or growth of vegetation in an amount of 1 gram acid equivalent per hectare (g ae/ha) or greater (e.g., 2 g ae/ha or greater, 3 g ae/ha or greater, 4 g ae/ha or greater, 5 g ae/ha or greater, 10 g ae/ha or greater, 15 g ae/ha or greater, 20 g ae/ha or greater, 25 g ae/ha or greater, 30 g ae/ha or greater, 35 g ae/ha or greater, 40 g ae/ha or greater, 45 g ae/ha or greater, 50 g ae/ha or greater, 55 g ae/ha or greater, 60 g ae/ha or greater, 65 g ae/ha or greater, 70 g ae/ha or greater, 75 g ae/ha or greater, 80 g ae/ha or greater, 85 g ae/ha or greater, 90 g ae/ha or greater, 95 g ae/ha or greater, 100 g ae/ha or greater, 110 g ae/ha or greater, 120 g ae/ha or greater, 130 g ae/ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, 290 g ae/ha or greater, 300 g ae/ha or greater, 310 g ae/ha or greater, 320 g ae/ha or greater, 330 g ae/ha or greater, 340 g ae/ha or greater, 350 g ae/ha or greater, 360 g ae/ha or greater, 370 g ae/ha or greater, 380 g ae/ha or greater, 390 g ae/ha or greater, 400 g ae/ha or greater, 420 g ae/ha or greater, 440 g ae/ha or greater, 460 g ae ha or greater, 480 g ae/ha or greater, 500 g ae/ha or greater, 520 g ae/ha or greater, 540 g ae/ha or greater, 560 g ae/ha or greater, 580 g ae/ha or greater, 600 g ae/ha or greater, 625 g ae/ha or greater, 650 g ae/ha or greater, 675 g ae/ha or greater, 700 g ae/ha or greater, 725 g ae/ha or greater, 750 g ae/ha or greater, 775 g ae/ha or greater, 800 g ae/ha or greater, 825 g ae/ha or greater, 850 g ae/ha or greater, 875 g ae/ha or greater, 900 g ae/ha or greater, 925 g ae/ha or greater, 950 g ae/ha or greater, 975 g ae/ha or greater, 1000 g ae/ha or greater, 1100 g ae/ha or greater, 1200 g ae/ha or greater, 1300 g ae/ha or greater, 1400 g ae/ha or greater, 1500 g ae/ha or greater, 1600 g ae/ha or greater, 1700 g ae/ha or greater, 1800 g ae/ha or greater, 1900 g ae/ha or greater, 2000 g ae/ha or greater, 2100 g ae/ha or greater, 2200 g ae/ha or greater, 2300 g ae/ha or greater, 2400 g ae/ha or greater, 2500 g ae/ha or greater, 2600 g ae/ha or greater, 2700 g ae/ha or greater, 2800 g ae/ha or greater, 2900 g ae/ha or greater, 3000 g ae/ha or greater, 3100 g ae/ha or greater, 3200 g ae ha or greater, 3300 g ae/ha or greater, 3400 g ae/ha or greater, 3500 g ae/ha or greater, 3600 g ae/ha or greater, 3700 g ae/ha or greater, 3800 g ae/ha or greater, or 3900 g ae/ha or greater,).

In some embodiments, the synthetic auxin herbicide or agriculturally acceptable salt or ester thereof is applied to vegetation or an area adjacent the vegetation or applied to soil or water to prevent the emergence or growth of vegetation in an amount of 4000 g ae/ha or less (e.g., 3900 g ae/ha or less, 3800 g ae/ha or less, 3700 g ae/ha or less, 3600 g ae/ha or less, 3500 g ae/ha or less, 3400 g ae/ha or less, 3300 g ae/ha or less, 3200 g ae/ha or less, 3100 g ae/ha or less, 3000 g ae/ha or less, 2900 g ae/ha or less, 2800 g ae/ha or less, 2700 g ae/ha or less, 2600 g ae/ha or less, 2500 g ae/ha or less, 2400 g ae/ha or less, 2300 g ae/ha or less, 2200 g ae/ha or less, 2100 g ae/ha or less, 2000 g ae/ha or less, 1900 g ae/ha or less, 1800 g ae/ha or less, 1700 g ae/ha or less, 1600 g ae/ha or less, 1500 g ae/ha or less, 1400 g a/ha or less, 1300 g ae/ha or less, 1200 g ae/ha or less, 1100 g ae/ha or less, 1000 g ae/ha or less, 975 g ae/ha or less, 950 g ae/ha or less, 925 g ae/ha or less, 900 g ae/ha or less, 875 g ae/ha or less, 850 g ae/ha or less, 825 g ae/ha or less, 800 g ae/ha or less, 775 g ae/ha or less, 750 g ae/ha or less, 725 g ae/ha or less, 700 g ae/ha or less, 675 g ae/ha or less, 650 g ae/ha or less, 625 g ae/ha or less, 600 g ae/ha or less, 580 g ae/ha or less, 560 g ae/ha or less, 540 g ae/ha or less, 520 g ae/ha or less, 500 g ae/ha or less, 480 g ae/ha or less, 460 g ae/ha or less, 440 g ae/ha or less, 420 g ae/ha or less, 400 g ac ha or less, 390 g ae/ha or less, 380 g ae/ha or less, 370 g ae/ha or less, 360 g ae ha or less, 350 g ae/ha or less, 340 g ae/ha or less, 330 g ae/ha or less, 320 g ae/ha or less, 310 g ae/ha or less, 300 g ae/ha or less, 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 45 g ae/ha or less, 40 g ae/ha or less, 35 g ae/ha or less, 30 g ae/ha or less, 25 g ae/ha or less, 20 g ae/ha or less, 15 g ae/ha or less, 10 g ae/ha or less, 5 g ae/ha or less, 4 g ae/ha or less, 3 g ae/ha or less, or 2 g ae/ha or less).

The synthetic auxin herbicide or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the synthetic auxin herbicide or agriculturally acceptable salt or ester thereof is applied to vegetation or an area adjacent the vegetation or applied to soil or water to prevent the emergence or growth of vegetation in an amount of from 1 g ae/ha to 4000 g ae/ha (e.g., 5 g ae/ha to 3000 g ae/ha, 1000-4000 g ae/ha, 1000-3000 g ae/ha, 1200-1500 g ae/ha, 280-2300 g ae/ha, 280-2250 g ae/ha, 1200-2700 g ae/ha, 450-800 g ae/ha, 100-400 g ae/ha, 70-300 g ae/ha, 10-400 g ae/ha, 50-400 g ae/ha, 5-1500 g ae/ha, 1500-3000 g ae/ha, 150-2500 g ae/ha, 2500-4000 g ae/ha, 1-900 g ae/ha, 900-1200 g ae/ha, 1-1000 g ae/ha, 1-850 g ae/ha, 1-800 g ae/ha, 1-760 g ae/ha, 1-700 g ae/ha, 1-660 g ae/ha, 1-620 g ae/ha, 1-600 g ae/ha, 1-560 g ae/ha, 5-750 g ae/ha, 750-1000 g ae/ha, 5-700 g ae/ha, 5-650 g ae/ha, 5-600 g ae/ha, 5-560 g ae/ha, 5-500 g ae/ha, 5-460 g ae/ha, 5-400 g ae/ha, 5460 g ae/ha, 5-400 g ae/ha, 5-360 g ae/ha, 5-300 g ae/ha, 5-280 g ae/ha, 5-260 g ae/ha, 5-240 g ae/ha, 5-220 g ae/ha, 5-200 g ae/ha, 5-180 g ae/ha, 5-160 g ae/ha, 5-140 g ae/ha, 5-120 g ae/ha, 5-100 g ae/ha, 5-90 g ae/ha, 5-80 g ae/ha, 5-70 g ae/ha, 5-60 g ae/ha, 5-50 g ae/ha, 5-40 g ae/ha, 5-30 g ae/ha, 5-20 g ae/ha, 5-10 g ae/ha, 10-560 g ae/ha, 20-500 g ae/ha, 30-460 g ae/ha, 40-400 g ae/ha, 50-360 g ae/ha, 60-300 g ae/ha, 70-280 g ae/ha, 70-100 g ae/ha, 70-140 g ae/ha, 100-140 g ae/ha, 100-280 g ae/ha, 140-500 g ae/ha, 140-440 g ae/ha, 140-420 g ae/ha, 140-380 g ae/ha, 140-360 g ae/ha, 140-340 g ae/ha, 140-300 g ae/ha, 140-280 g ae/ha, 140-220 g ae/ha, 800-2000 g ae/ha, 600-1500 g ae/ha, 400-1000 g ae/ha, 1200-2000 g ae/ha, 1400-2500 g ae/ha, 2000-4000 g ae/ha, 1600-2400 g ae/ha, 40-350 g ae/ha, 40-200 g ae/ha, 1-210 g ae/ha, 1-240 g ae/ha, 1-180 g ae/ha, or 1-560 g ae/ha).

In certain embodiments, the herbicidal composition comprises a synergistic herbicidally effective amount of (a) a pyridine carboxylic acid herbicide or an agriculturally acceptable N-oxide, salt or ester thereof, and (b) 2,4-D, 2,4-DB, MCPA, dichlorprop, mecoprop, dicamba, clopyralid, fluroxypyr, halauxifen, picloram, triclopyr, aminocyclopyrachlor, aminopyralid, quinclorac, 4-amino-3-chloro-6-(4-chloro-2-fluoro-3-methoxyphenyl)-5-fluoro-2-pyridinecarboxylic acid, or an agriculturally acceptable salt or ester thereof.

Dicamba

Compositions and methods of the present disclosure can include dicamba or an agriculturally acceptable salt or ester thereof. Dicamba, shown below, is a benzoic acid herbicide that provides broad-spectrum control of annual and perennial broad-leaved weeds and brush species in cereals, maize, sorghum, sugar cane, asparagus, perennial seed grasses, turf, pastures, rangeland, and non-crop land. Dicamba, as well as methods of making dicamba, are known in the art. Its herbicidal activity is described, for example, in The Pesticide Manual, Sixteenth Edition, 2012.

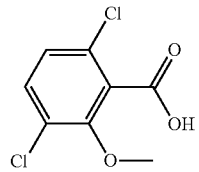

In some embodiments, dicamba can be provided as an agriculturally acceptable salt or ester of dicamba. Exemplary agriculturally acceptable salts and esters of dicamba include, but are not limited to, dicamba-diglycolamine, dicamba-dimethylammonium, dicamba-diolamine, dicamba-isopropylammonium, dicamba-methyl (disugran), dicamba-olamine, dicamba-potassium, dicamba-sodium, dicamba-trolamine, and cambendichlor.

Clopyralid

Compositions and methods of the present disclosure can include clopyralid or an agriculturally acceptable salt or ester thereof. Clopyralid, shown below, is a picolinic acid herbicide that provides broad-spectrum control of many annual and perennial broad-leaved weeds in sugar beet, fodder beet, spring rape, maize, cereals, brassicas, onions, leeks, strawberries flax, grassland and non-crop lands. Clopyralid, as well as methods of making clopyralid, are known in the art. Its herbicidal activity is described, for example, in The Pesticide Manual, Sixteenth Edition, 2012.

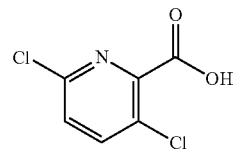 [SMILES: O=C(O)c1nc(Cl)ccc1Cl]

In some embodiments, clopyralid can be provided as an agriculturally acceptable salt or ester of clopyralid. Exemplary agriculturally acceptable salts and esters of clopyralid include, but are not limited to, clopyralid-methyl, clopyralid-olamine, clopyralid-potassium, and clopyralid-tris(2-hydroxypropyl)ammonium.

Fluroxypyr

Compositions and methods of the present disclosure can include fluroxypyr or an agriculturally acceptable salt or ester thereof. Fluroxypyr, shown below, is a pyridine carboxylic acid herbicide that provides protection against a variety of broad-leaved weeds in small grain crops, pastures, grasslands, orchards, plantation crops, maize, and forestry. Fluroxypyr, as well as methods of making fluroxypyr, are known in the art. Its herbicidal activity is described, for example, in The Pesticide Manual, Sixteenth Edition, 2012.

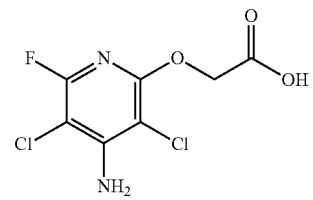 [SMILES: Nc1c(Cl)c(F)nc(OCC(=O)O)c1Cl]

In some embodiments, fluroxypyr can be provided as an agriculturally acceptable salt or ester of fluroxypyr. Exemplary agriculturally acceptable salts and esters of fluroxypyr include, but are not limited to, fluroxypyr-butometyl and fluroxypyr-meptyl (fluroxypyr-MHE). In some embodiments, the fluroxypyr can be provided as fluroxypyr-meptyl (fluroxypyr-MHE), shown below.

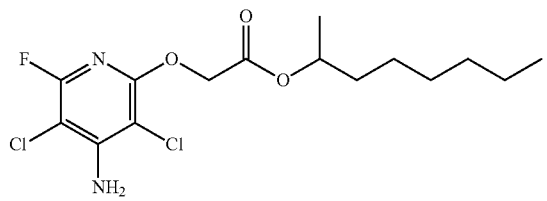 [SMILES: CCCCCCC(C)OC(=O)COc1nc(F)c(Cl)c(N)c1Cl]

Aminocyclopyrachlor

Compositions and methods of the present disclosure can include aminocyclo-pyrachlor or an agriculturally acceptable salt or ester thereof. Aminocyclopyrachlor is a pyrimidine carboxylic acid herbicide that provides control of broadleaf weeds and woody species, e.g., in rights-of-way, industrial sites, rangeland, permanent grass pastures and natural areas. Aminocyclopyrachlor, as well as methods of making amino-cyclopyrachlor, are known in the art. Its herbicidal activity is described in *The Pesticide Manual*, Sixteenth Edition, 2012.

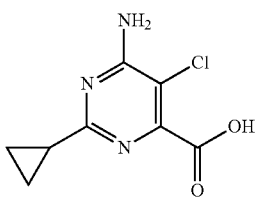 [SMILES: Nc1nc(C2CC2)nc(C(=O)O)c1Cl]

In some embodiments, aminocyclopyrachlor can be provided as an agriculturally acceptable salt or ester of aminocyclopyrachlor. Exemplary agriculturally acceptable salts and esters of aminocyclopyrachlor include, but are not limited to, aminocyclopyrachlor-potassium and aminocyclopyrachlor-methyl.

Dicamba, clopyralid, fluroxypyr, aminocyclopyrachlor, or an agriculturally acceptable salts or esters thereof can be applied to vegetation or an area adjacent the vegetation or applied to soil or water to prevent the emergence or growth of vegetation in an amount sufficient to induce a herbicidal effect. In some embodiments, the dicamba, clopyralid, fluroxypyr, aminocyclopyrachlor, or agriculturally acceptable salts or esters thereof can be applied to vegetation or an area adjacent the vegetation or applied to soil or water to prevent the emergence or growth of vegetation in an amount of 50 grams acid equivalent per hectare (g ae/ha) or greater (e.g., 60 g ae/ha or greater, 70 g ae/ha or greater, 80 g ae/ha or greater, 90 g ae/ha or greater, 100 g ae/ha or greater, 110 g ae/ha or greater, 120 g ae/ha or greater, 130 g ae/ha or greater, 140 g ae/ha or greater, 150 g ace/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, 290 g ae/ha or greater, 300 g ae/ha or greater, 310 g ae/ha or greater, 320 g ae/ha or greater, 330 g ae/ha or greater, 340 g ae/ha or greater, 350 g ae/ha or greater, 360 g ae/ha or greater, 370 g ae/ha or greater, 380 g ae/ha or greater, or 390 g ae/ha or greater).

In some embodiments, the dicamba, clopyralid, fluroxypyr, aminocyclopyrachlor, or agriculturally acceptable salts or esters thereof can be applied to vegetation or an area adjacent the vegetation or applied to soil or water to prevent the emergence or growth of vegetation in an amount of 400 g ae/ha or less (e.g., 390 g ae/ha or less, 380 g ae/ha or less, 370 g ae/ha or less, 360 g ae/ha or less, 350 g ae/ha or less, 340 g ace/ha or less, 330 g ae/ha or less, 320 g ae/ha or less, 310 g ae/ha or less, 300 g ae/ha or less, 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 90 g ae/ha or less, 80 g ae/ha or less, 70 g ae/ha or less, or 60 g ae/ha or less).

The dicamba, clopyralid, fluroxypyr, aminocyclopyrachlor, or agriculturally acceptable salts or esters thereof can be applied to vegetation or an area adjacent the vegetation or applied to soil or water to prevent the emergence or growth of vegetation in an amount ranging from any of the minimum values described above to any of the maximum values described above. In some embodiments, the dicamba, clopyralid, fluroxypyr, aminocyclopyrachlor, or agriculturally acceptable salts or esters thereof can be applied to vegetation or an area adjacent the vegetation or applied to soil or water to prevent the emergence or growth of vegetation in an amount of from 50 g ae/ha to 400 g ae/ha (e.g., 50-200 g ae/ha, 200-400 g ae/ha, 100-300 g ae/ha, 50-100 g ae/ha, 50-90 g ae/ha, or 60-80 g ae/ha).

Aminopyralid

Compositions and methods of the present disclosure can include aminopyralid or an agriculturally acceptable salt or ester thereof. Aminopyralid is a picolinic acid herbicide that provides long-term control of annual and perennial broadleaf weeds, e.g., in range and pasture. Aminocyclopyrachlor, as well as methods of making amino-cyclopyrachlor, are known in the art. Its herbicidal activity is described in *The Pesticide Manual*, Sixteenth Edition, 2012.

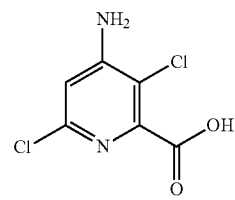 [SMILES: Nc1cc(Cl)nc(C(=O)O)c1Cl]

In some embodiments, aminopyralid can be provided as an agriculturally acceptable salt or ester of aminopyralid. Exemplary agriculturally acceptable salts and esters of aminopyralid include, but are not limited to, for example, aminopyralid-triisopropanolammonium (TIPA), shown below.

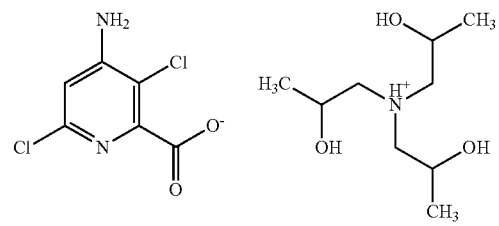

Halauxifen

In certain embodiments, the synthetic auxin inhibitor can comprise halauxifen or an agriculturally acceptable salt or ester thereof. Halauxifen, shown below, is an arylpicolinic acid herbicide that provides broad-spectrum control of broad-leaved weeds in cereal crops.

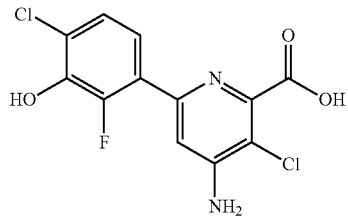 [SMILES: Nc1cc(-c2ccc(Cl)c(O)c2F)nc(C(=O)O)c1Cl]

In some embodiments, halauxifen can be provided as an agriculturally acceptable salt or ester of halauxifen. Exemplary agriculturally acceptable salts and esters of halauxifen include, but are not limited to, halauxifen-methyl. In some embodiments, the halauxifen is provided as halauxifen-methyl, shown below.

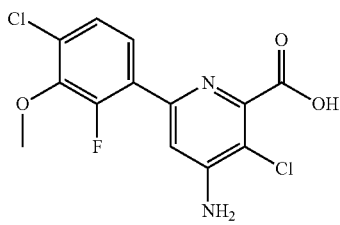 [SMILES: COc1c(Cl)ccc(-c2cc(N)c(Cl)c(C(=O)O)n2)c1F]

4-Amino-3-chloro-6-(4-chloro-2-fluoro-3-methoxyphenyl)-5-fluoro-2-pyridinecarboxylic Acid Compositions and methods of the present disclosure can include 4-amino-3-chloro-6-(4-chloro-2-fluoro-3-methoxyphenyl)-5-fluoro-2-pyridinecarboxylic acid or an agriculturally acceptable salt or ester thereof. 4-Amino-3-chloro-6-(4-chloro-2-fluoro-3-methoxyphenyl)-5-fluoro-2-pyridinecarboxylic acid is arylpicolinic acid that has been described in U.S. Pat. No. 7,314,849 B2. Exemplary uses of 4-amino-3-chloro-6-(4-chloro-2-fluoro-3-methoxyphenyl)-5-fluoro-2-pyridinecarboxylic acid include controlling undesirable vegetation, including grass, broadleaf and sedge weeds, in multiple non-crop and cropping situations.

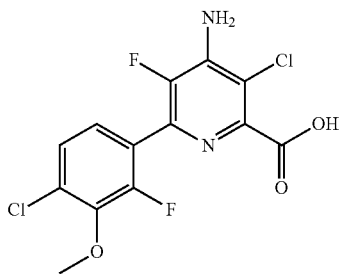 [SMILES: COc1c(Cl)ccc(-c2nc(C(=O)O)c(Cl)c(N)c2F)c1F]

In some embodiments, 4-amino-3-chloro-6-(4-chloro-2-fluoro-3-methoxyphenyl)-5-fluoro-2-pyridinecarboxylic acid can be provided as an agriculturally acceptable salt or ester of -amino-3-chloro-6-(4-chloro-2-fluoro-3-methoxyphenyl)-5-fluoro-2-pyridinecarboxylic acid. Exemplary agriculturally acceptable salts and esters of 4-amino-3-chloro-6-(4-chloro-2-fluoro-3-methoxyphenyl)-5-fluoro-2-pyridinecarboxylic acid include, but are not limited to, benzyl 4-amino-3-chloro-6-(4-chloro-2-fluoro-3-methoxyphenyl)-5-fluoropyridine-2-carboxylate, shown below.

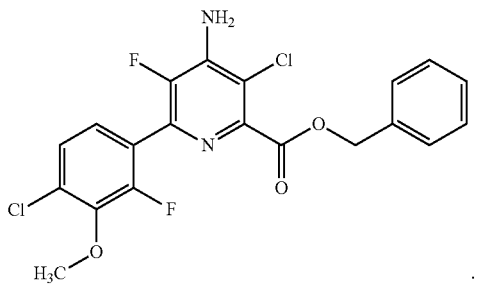 [SMILES: COc1c(Cl)ccc(-c2nc(C(=O)OCc3ccccc3)c(Cl)c(N)c2F)c1F]

The aminopyralid, halauxifen, 4-amino-3-chloro-6-(4-chloro-2-fluoro-3-methoxyphenyl)-5-fluoro-2-pyridinecarboxylic acid, or agriculturally acceptable salts or esters thereof can be applied to vegetation or an area adjacent the vegetation or applied to soil or water to prevent the emergence or growth of vegetation in an amount sufficient to induce a herbicidal effect. In some embodiments, aminopyralid, halauxifen, 4-amino-3-chloro-6-(4-chloro-2-fluoro-3-methoxyphenyl)-5-fluoro-2-pyridinecarboxylic acid, or agriculturally acceptable salts or esters thereof is applied to vegetation or an area adjacent the vegetation or applied to soil or water to prevent the emergence or growth of vegetation in an amount of 1 gram acid equivalent per hectare (g ae/ha) or greater (e.g., 1.5 g ae/ha or greater, 2 g ae/ha or greater, 2.5 g ae/ha or greater, 2 g ae/ha or greater, 2.5 g ae/ha or greater, 3 g ae/ha or greater, 4.5 g ae/ha or greater, 5 g ae/ha or greater, 5.5 g ae/ha or greater, 6 g ae/ha or greater, 6.5 g ace/ha or greater, 7 g ae/ha or greater, 7.5 g ae/ha or greater, 8 g ae/ha or greater, 8.5 g ae/ha or greater, 9 g ae/ha or greater, 9.5 g ae/ha or greater, 10 g ae/ha or greater, 12 g ae/ha or greater, 14 g ae/ha or greater, 16 g ae/ha or greater, 18 g ae/ha or greater, 20 g ae/ha or greater, 25 g ae/ha or greater, 30 g ae/ha or greater, 35 g ae/ha or greater, 40 g ae/ha or greater, 45 g ae/ha or greater, 50 g ae/ha or greater, 55 g ae/ha or greater, 60 g ae/ha or greater, 65 g ae/ha or greater, 70 g ae/ha or greater, 75 g ae/ha or greater, 80 g ae/ha or greater, 85 g ae/ha or greater, 90 g ae/ha or greater, 95 g ae/ha or greater, 100 g ae/ha or greater, 105 g ae/ha or greater, 110 g ae/ha or greater, 115 g ae/ha or greater, 120 g ae/ha or greater, 125 g ae/ha or greater, 130 g ae/ha or greater, 135 g ae/ha or greater, 140 g ae/ha or greater, or 145 g ae/ha or greater).

In some embodiments, aminopyralid, halauxifen, 4-amino-3-chloro-6-(4-chloro-2-fluoro-3-methoxyphenyl)-5-fluoro-2-pyridinecarboxylic acid, or agriculturally acceptable salts or esters thereof is applied to vegetation or an area adjacent the vegetation or applied to soil or water to prevent the emergence or growth of vegetation in an amount of 150 g ae/ha or less (e.g., 145 g ae/ha or less, 140 g ae/ha or less, 135 g ae/ha or less, 130 g ae/ha or less, 125 g ae/ha or less, 120 g ae/ha or less, 115 g ae/ha or less, 110 g ae/ha or less, 105 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 45 g ae/ha or less, 40 g ae/ha or less, 35 g ae/ha or less, 30 g ae/ha or less, 25 g ae/ha or less, 20 g ae/ha or less, 18 g ae/ha or less, 16 g ae/ha or less, 14 g ae/ha or less, 12 g ae/ha or less, 10 g ae/ha or less, 9.5 g ae/ha or less, 9 g ae/ha or less, 8.5 g ace/ha or less, 8 g ae/ha or less, 7.5 g ae/ha or less, 7 g ae/ha or less, 6.5 g ae/ha or less, 6 g ae/ha or less, 5.5 g ae/ha or less, 5 g ae/ha or less, 4.5 g ae/ha or less, 4 g ae/ha or less, 3.5 g ae/ha or less, 3 g ae/ha or less, 2.5 g ae/ha or less, 2 g ae/ha or less, or 1.5 g ae/ha or less).

The aminopyralid, halauxifen, 4-amino-3-chloro-6-(4-chloro-2-fluoro-3-methoxyphenyl)-5-fluoro-2-pyridinecarboxylic acid, or agriculturally acceptable salts or esters thereof can be applied to vegetation or an area adjacent the vegetation or applied to soil or water to prevent the emergence or growth of vegetation in an amount ranging from any of the minimum values described above to any of the maximum values described above. In some embodiments, the aminopyralid, halauxifen, 4-amino-3-chloro-6-(4-chloro-2-fluoro-3-methoxyphenyl)-5-fluoro-2-pyridinecarboxylic acid, or agriculturally acceptable salts or esters thereof is applied to vegetation or an area adjacent the vegetation or applied to soil or water to prevent the emergence or growth of vegetation in an amount of from 1 g ae/ha to 150 g ae/ha (e.g., 1-70 g ae/ha, 70-150 g ae/ha, 70-120 g ae/ha, 1-80 g ae/ha, 1-90 g ae/ha, or 20-80 g ae/ha).

Quinclorac

Compositions and methods of the present disclosure can include quinclorac or an agriculturally acceptable salt or ester thereof. Quinclorac, shown below, is a quinoline carboxylic acid herbicide that provides pre- and post-emergence control of grass weeds (*Echinochloa* spp., *Aeschynomene* spp., *Sesbania* spp.) and other weeds in direct-seeded and transplanted rice. Quinclorac, as well as methods of making quinclorac, are known in the art. Its herbicidal activity is described, for example, in *The Pesticide Manual*, Sixteenth Edition, 2012.

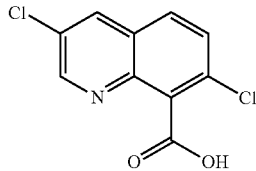 [SMILES: O=C(O)c1c(Cl)ccc2cc(Cl)cnc12]

In some embodiments, quinclorac can be provided as an agriculturally acceptable salt or ester of quinclorac. Exemplary agriculturally acceptable salts and esters of quinclorac include, but are not limited to, quinclorac-dimethylammonium.

Picloram

In certain embodiments, the synthetic auxin herbicide can comprise picloram or an agriculturally acceptable salt or ester thereof. Picloram is a picolinic acid herbicide that provides management of unwanted vegetation, e.g., in rangeland, grass pastures, forestry, as well as non-crop land and right-of-way sites. Picloram, as well as methods of making picloram, are known in the art. Its herbicidal activity is described in *The Pesticide Manual*, Sixteenth Edition, 2012.

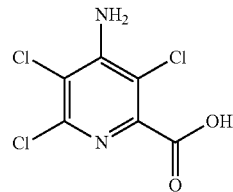 [SMILES: Nc1c(Cl)c(Cl)nc(C(=O)O)c1Cl]

In some embodiments, picloram can be provided as an agriculturally acceptable salt or ester of picloram. Exemplary agriculturally acceptable salts and esters of picloram include, but are not limited to, picloram-dimethylammonium, picloram-isoctyl, picloram-potassium, picloram-triethylammonium, picloram-triisopropanolammonium (TIPA), picloram-triisopropylammonium, and picloram-trolamine (triethanolammonium). In some embodiments, the picloram can be provided as picloram-potassium, shown below.

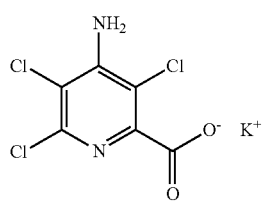 [SMILES: Nc1c(Cl)c(Cl)nc(C(=O)[O-])c1Cl ; [K+]]

In some embodiments, the picloram can be provided as picloram-TIPA, shown below.

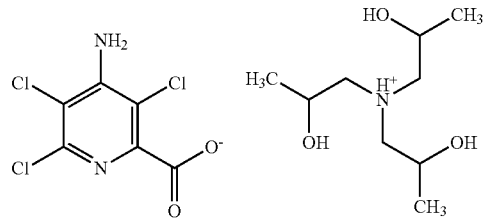

Triclopyr

In certain embodiments, the synthetic auxin herbicide can include triclopyr or an agriculturally acceptable salt or ester thereof. Triclopyr is a picolinic acid herbicide that provides control of woody plants and broadleaf weed species, e.g., in grassland, uncultivated land, industrial areas, coniferous forests, rice and plantation crops. Triclopyr, as well as methods of making triclopyr, are known in the art. Its herbicidal activity is described in *The Pesticide Manual*, Sixteenth Edition, 2012.

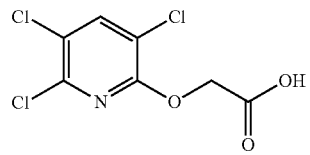 [SMILES: O=C(O)COc1nc(Cl)c(Cl)cc1Cl]

In some embodiments, triclopyr can be provided as an agriculturally acceptable salt or ester of triclopyr. Exemplary agriculturally acceptable salts and esters of triclopyr include, but are not limited to, for example, triclopyr-triethylammonium (TEA), triclopyr choline, and triclopyr-butotyl (butoxyethyl or BEE). In some embodiments, the triclopyr can be provided as triclopyr-triethylammonium (TEA), shown below.

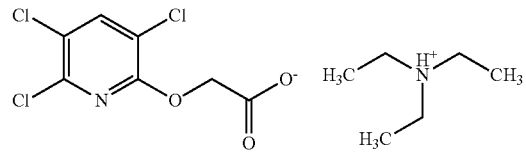

In some embodiments, the triclopyr can be provided as triclopyr-choline, shown below.

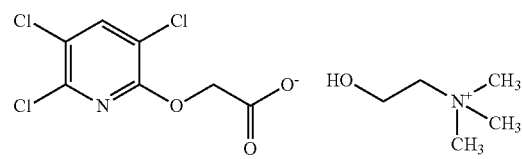

In some embodiments, the triclopyr can be provided as triclopyr-BEE, shown below.

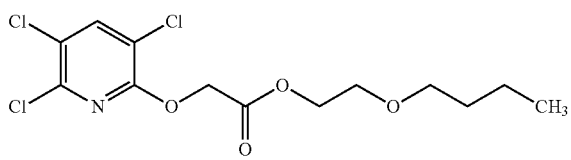 [SMILES: CCCCOCCOC(=O)COc1nc(Cl)c(Cl)cc1Cl]

The quinclorac, picloram, triclopyr, or agriculturally acceptable salts or esters thereof can be applied to vegetation or an area adjacent the vegetation or applied to soil or water to prevent the emergence or growth of vegetation in an amount sufficient to induce a herbicidal effect. In some embodiments, the quinclorac, picloram, triclopyr, or agriculturally acceptable salts or esters thereof is applied to vegetation or an area adjacent the vegetation or applied to soil or water to prevent the emergence or growth of vegetation in an amount of 10 grams acid equivalent per hectare (g ae/ha) or greater (e.g., 20 g ae/ha or greater, 30 g ae/ha or greater, 40 g ae/ha or greater, 50 g ae/ha or greater, 60 g ae/ha or greater, 70 g ae/ha or greater, 80 g ae/ha or greater, 90 g ae/ha or greater, 100 g ae/ha or greater, 200 g ae/ha or greater, 300 g ae/ha or greater, 400 g ae/ha or greater, 500 g ae/ha or greater, 600 g ae/ha or greater, 700 g ae/ha or greater, 800 g ae/ha or greater, 900 g ae/ha or greater, 1000 g ae/ha or greater, 1100 g ae/ha or greater, 1200 g ae/ha or greater, 1300 g ae/ha or greater, 1400 g ae/ha or greater, 1500 g ae/ha or greater, 1600 g ae/ha or greater, 1700 g ae/ha or greater, 1800 g ae/ha or greater, 1900 g ae/ha or greater, 2000 g ae/ha or greater, 2100 g ae/ha or greater, 2200 g ae/ha or greater, 2210 g ae/ha or greater, 2220 g ae/ha or greater, or 2230 g ae/ha or greater).

In some embodiments, the quinclorac, picloram, triclopyr, or agriculturally acceptable salts or esters thereof is applied to vegetation or an area adjacent the vegetation or applied to soil or water to prevent the emergence or growth of vegetation in an amount of 2240 g ae/ha or less (e.g., 2230 g ae/ha or less, 2220 g ae/ha or less, 2210 g ae/ha or less, 2000 g ae/ha or less, 1900 g ae/ha or less, 1800 g ae/ha or less, 1700 g ae/ha or less, 1600 g ae/ha or less, 1500 g ae/ha or less, 1400 g ae/ha or less, 1300 g ae/ha or less, 1200 g ae/ha or less, 1100 g ae/ha or less, 1000 g ae/ha or less, 900 g ae/ha or less, 800 g ae/ha or less, 700 g ae/ha or less, 600 g ae/ha or less, 500 g ae/ha or less, 400 g ae/ha or less, 300 g ae/ha or less, 200 g ae/ha or less, 100 g ae/ha or less, 90 g ae ha or less, 80 g ae/ha or less, 70 g ae/ha or less, 60 g ae/ha or less, 50 g ae/ha or less, 40 g ae/ha or less, or 30 g ae/ha or less).

The quinclorac, picloram, triclopyr, or agriculturally acceptable salts or esters thereof can be applied to vegetation or an area adjacent the vegetation or applied to soil or water to prevent the emergence or growth of vegetation in an amount ranging from any of the minimum values described above to any of the maximum values described above. In some embodiments, the quinclorac, picloram, triclopyr, or agriculturally acceptable salts or esters thereof is applied to vegetation or an area adjacent the vegetation or applied to soil or water to prevent the emergence or growth of vegetation in an amount of from 10 g ae/ha to 2240 g ae/ha (e.g., 1000-2240 g ae/ha, 10-1000 g ae/ha, 10-500 g ae/ha, 20-1200 g ae/ha, 50-1500 g ae/ha, 100-500 g ae/ha, or 150-750 g ae/ha).

Auxin Transport Inhibitors

In addition to the pyridine carboxylic acid herbicide or agriculturally acceptable N-oxide, salt or ester thereof, the compositions can include an auxin transport inhibitor. Auxin transport inhibitors inhibit polar transport of naturally occurring auxin, indoleacetic acid (IAA), and synthetic auxin-mimicking herbicides in sensitive plants. Examples of auxin transport inhibitors include phthalamate herbicides, semicarbazone herbicides, and others. In some embodiments, the auxin transport inhibitor can comprise a semicarbazone herbicide. In some embodiments, the auxin transport inhibitor can comprise a phthalamate herbicide. In some embodiments, the auxin transport inhibitor can comprise other benzoic acids.

In some embodiments, the composition can include an auxin transport inhibitor selected from the group consisting of diflufenzopyr, naptalam, 2,3,5-triiodobenzoic acid (2,3,5-TIBA), agriculturally acceptable salts and esters thereof, and combinations thereof.

Diflufenzopyr

In certain embodiments, the auxin transport inhibitor can comprise diflufenzopyr or an agriculturally acceptable salt or ester thereof. Diflufenzopyr, shown below, is a semicarbazone herbicide that provides control of broad-leaved and perennial weeds in maize, pastures, rangeland, and non-crop areas. Diflufenzopyr, as well as methods of preparing diflufenzopyr, are known in the art. Its herbicidal activity is described, for example, in The Pesticide Manual, Sixteenth Edition, 2012.

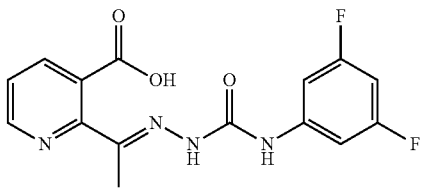 [SMILES: C/C(=N\NC(=O)Nc1cc(F)cc(F)c1)c1ncccc1C(=O)O]

The auxin transport inhibitor (e.g., diflufenzopyr) or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the auxin transport inhibitor (e.g., diflufenzopyr) or agriculturally acceptable salt or ester thereof is applied to vegetation or an area adjacent the vegetation or applied to soil or water to prevent the emergence or growth of vegetation in an amount of 1 gram of acid equivalent per hectare (g ae/ha) or greater (e.g., 1.5 g ae/ha or greater, 2 g ae/ha or greater, 2.5 g ae/ha or greater, 3 g ae/ha or greater, 3.5 g ae/ha or greater, 4 g ae/ha or greater, 5 g ae/ha or greater, 6 g ae/ha or greater, 7 g ae/ha or greater, 8 g ae/ha or greater, 9 g ae/ha or greater, 10 g ae/ha or greater, 15 g ae/ha or greater, 20 g ae/ha or greater, 25 g ae/ha or greater, 30 g ae/ha or greater, 35 g ae/ha or greater, 40 g ae/ha or greater, 45 g ae/ha or greater, 50 g ae/ha or greater, 55 g ae/ha or greater, 60 g ae/ha or greater, 65 g ae/ha or greater, 70 g ae/ha or greater, 75 g ae/ha or greater, 80 g ae/ha or greater, 85 g ae/ha or greater, 90 g ae/ha or greater, 95 g ae/ha or greater, 100 g ae/ha or greater, 110 g ae/ha or greater, 120 g ae/ha or greater, 130 g ae/ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, 290 g ae/ha or greater, 300 g ae/ha or greater, 310 g ae/ha or greater, 320 g ae/ha or greater, 330 g ae/ha or greater, 340 g ae/ha or greater, 350 g ae/ha or greater, 360 g ae/ha or greater, 370 g ae/ha or greater, 380 g ae/ha or greater, 390 g ae/ha or greater, 400 g ae/ha or greater, 420 g ae/ha or greater, 440 g ae/ha or greater, 460 g ae/ha or greater, 480 g ae/ha or greater, 500 g ae/ha or greater, 520 g ae/ha or greater, 540 g ae/ha or greater, 560 g ae/ha or greater, 580 g ae/ha or greater, 600 g ae/ha or greater, 625 g ae/ha or greater, 650 g ae/ha or greater, 675 g ae/ha or greater, 700 g ae/ha or greater, 725 g ae/ha or greater, 750 g ae/ha or greater, 775 g ae/ha or greater, 800 g ae/ha or greater, 825 g ae/ha or greater, 850 g ae/ha or greater, 875 g ae/ha or greater, 900 g ae/ha or greater, 925 g ae/ha or greater, 950 g ae/ha or greater, or 975 g ae/ha or greater).

In some embodiments, the auxin transport inhibitor (e.g., diflufenzopyr) or agriculturally acceptable salt or ester thereof is applied to vegetation or an area adjacent the vegetation or applied to soil or water to prevent the emergence or growth of vegetation in an amount of 1000 g ae/ha or less (e.g., 975 g ae/ha or less, 950 g ae/ha or less, 925 g ae/ha or less, 900 g ae/ha or less, 875 g ae/ha or less, 850 g ae/ha or less, 825 g ae/ha or less, 800 g ae/ha or less, 775 g ae/ha or less, 750 g ae/ha or less, 725 g ae/ha or less, 700 g ae/ha or less, 675 g ae/ha or less, 650 g ae/ha or less, 625 g ae/ha or less, 600 g ae/ha or less, 580 g ae/ha or less, 560 g ae/ha or less, 540 g ae/ha or less, 520 g ae/ha or less, 500 g ae/ha or less, 480 g ae/ha or less, 460 g ae/ha or less, 440 g ae/ha or less, 420 g ae/ha or less, 400 g ae/ha or less, 390 g ae/ha or less, 380 g ae/ha or less, 370 g ae/ha or less, 360 g ae/ha or less, 350 g ae/ha or less, 340 g ae/ha or less, 330 g ae/ha or less, 320 g ae/ha or less, 310 g ae/ha or less, 300 g ae/ha or less, 290 g ae/ha or less, 280 g ae/ha or less, 270 g ae/ha or less, 260 g ae/ha or less, 250 g ae ha or less, 240 g ae/ha or less, 230 g ae/ha or less, 220 g ae/ha or less, 210 g ae/ha or less, 200 g ae/ha or less, 190 g ae ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 45 g ae/ha or less, 40 g ae/ha or less, 35 g ae ha or less, 30 g ae/ha or less, 25 g ae/ha or less, 20 g ae ha or less, 15 g ae/ha or less, 10 g ae/ha or less, 9 g ae/ha or less, 8 g ae/ha or less, 7 g ae/ha or less, 6 g ae/ha or less, 5 g ae/ha or less, 4 g ae/ha or less, 3.5 g ae/ha or less, 3 g ae/ha or less, 2.5 g ae/ha or less, 2 g ae/ha or less, or 1.5 g ae/ha or less).

The auxin transport inhibitor (e.g., diflufenzopyr) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the auxin transport inhibitor (e.g., diflufenzopyr) or agriculturally acceptable salt or ester thereof is applied to vegetation or an area adjacent the vegetation or applied to soil or water to prevent the emergence or growth of vegetation in an amount of from 1-1000 g ae/ha (e.g., from 1-750 g ae/ha, from 3.5-750 g ae/ha, from 3.5-700 g ae/ha, from 3.5-650 g ae/ha, from 3.5-600 g ae/ha, from 3.5-560 g ae/ha, from 3.5-500 g ae/ha, from 3.5-460 g ae/ha, from 3.5-400 g ae/ha, from 3.5-460 g ae/ha, from 3.5-400 g ae/ha, from 3.5-360 g ae/ha, from 3.5-300 g ae/ha, from 3.5-280 g ae/ha, from 3.5-260 g ae/ha, from 3.5-240 g ae/ha, from 3.5-220 g ae/ha, from 3.5-200 g ae/ha, from 3.5-180 g ae/ha, from 3.5-160 g ae/ha, from 3.5-140 g ae/ha, from 3.5-120 g ae/ha, from 3.5-100 g ae/ha, from 3.5-90 g ae/ha, from 3.5-80 g ae/ha, from 3.5-70 g ae/ha, from 3.5-60 g ae/ha, from 3.5-50 g ae/ha, from 3.5-40 g ae/ha, from 3.5-30 g ae/ha, from 3.5-20 g ae/ha, from 3.5-15 g ae/ha, from 3.5-10 g ae/ha, from 1-50 g ae/ha, from 1-40 g ae/ha, from 1-30 g ae/ha, from 1-20 g ae/ha, from 1-15 g ae/ha, from 1-10 g ae a, from 10-560 g ae/ha, from 20-500 g ae/ha, from 30-460 g ae/ha, from 40-400 g ae/ha, from 50-360 g ae/ha, from 60-300 g ae/ha, from 70-280 g ae/ha, from 70-100 g ae/ha, from 70-140 g ae ha, from 100-140 g ae/ha, from 100-280 g ae/ha, or from 140-280 g ae/ha). In certain embodiments, the auxin transport inhibitor (e.g., diflufenzopyr) or agriculturally acceptable salt or ester thereof is applied to vegetation or an area adjacent the vegetation or applied to soil or water to prevent the emergence or growth of vegetation in an amount of from 3.5-15 g ae/ha.

Naptalam

In certain embodiments, the auxin transport inhibitor can comprise naptalam or an agriculturally acceptable salt or ester thereof. Naptalam is a phthalamate herbicide that provides pre-emergence control of many broad-leaved weeds and some grasses in cucurbits, asparagus, peanuts, soybeans, and established woody ornamentals. It is described in *The Pesticide Manual*, Fourteenth Edition, 2006. Exemplary forms of naptalam include its sodium salt.

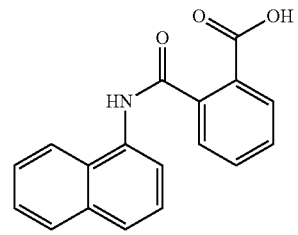 [SMILES: O=C(O)c1ccccc1C(=O)Nc1cccc2ccccc12]

2,3,5-Triiodobenzoic Acid

In certain embodiments, the auxin transport inhibitor can comprise 2,3,5-triiodobenzoic acid or an agriculturally acceptable salt or ester thereof. 2,3,5-Triiodobenzoic acid inhibits auxin efflux and thus blocks polar auxin movement between cells (Dhonukshe et al. *Proc. Natl. Acad. Sci.* 2008:105(11) 4489-4494).

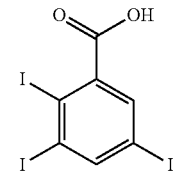 [SMILES: O=C(O)c1cc(I)cc(I)c1I]

The auxin transport inhibitor (e.g., naptalam or 2,3,5-triiodobenzoic acid) or agriculturally acceptable salts or esters thereof can be applied to vegetation or an area adjacent the vegetation or applied to soil or water to prevent the emergence or growth of vegetation in an amount sufficient to induce a herbicidal effect. In some embodiments, the auxin transport inhibitor (e.g., naptalam or 2,3,5-triiodobenzoic acid) or agriculturally acceptable salts or esters thereof is applied to vegetation or an area adjacent the vegetation or applied to soil or water to prevent the emergence or growth of vegetation in an amount of 140 grains acid equivalent per hectare (g ae/ha) or greater (e.g., 150 g ae/ha or greater, 200 g ae/ha or greater, 250 g ae/ha or greater, 300 g ae/ha or greater, 350 g ae/ha or greater, 400 g ae/ha or greater, 450 g ae/ha or greater, 500 g ae/ha or greater, 550 g ae/ha or greater, 600 g ae/ha or greater, 650 g ae/ha or greater, 700 g ae/ha or greater, 750 g ae/ha or greater, 800 g ae/ha or greater, 850 g ae/ha or greater, 900 g ae/ha or greater, 1000 g ae/ha or greater, 1100 g ae/ha or greater, 1200 g ae/ha or greater, 1300 g ae/ha or greater, 1400 g ae/ha or greater, 1500 g ae/ha or greater, 1600 g ae/ha or greater, 1700 g ae/ha or greater, 1800 g ae/ha or greater, 1900 g ae/ha or greater, 2000 g ae/ha or greater, 2200 g ae/ha or greater, 2400 g ae/ha or greater, 2600 g ae/ha or greater, 2800 g ae/ha or greater, 3000 g ae/ha or greater, 3200 g ae/ha or greater, 3400 g ae/ha or greater, 3600 g ae/ha or greater, 3800 g ae/ha or greater, 3850 g ae/ha or greater, 3900 g ae/ha or greater, 3950 g ae/ha or greater, 4000 g ae/ha or greater, 4050 g ae/ha or greater, 4100 g ae/ha or greater, 4150 g ae/ha or greater, 4200 g ae/ha or greater, 4250 g ae/ha or greater, 4300 g ae/ha or greater, 4350 g ae/ha or greater, 4400 g ae/ha or greater, 4450 g ae/ha or greater, 4500 g ae/ha or greater, 4550 g ae/ha or greater, 4600 g ae/ha or greater, 4650 g ae/ha or greater, 4700 g ae/ha or greater, 4750 g ae/ha or greater, 4800 g ae/ha or greater, 4850 g ae/ha or greater, 4900 g ae/ha or greater, 4950 g ae/ha or greater, 5000 g ae/ha or greater, 5050 g ae/ha or greater, 5100 g ae/ha or greater, 5150 g ae/ha or greater, 5200 g ae/ha or greater, 5250 g ae/ha or greater, 5300 g ae/ha or greater, 5350 g ae/ha or greater, 5400 g ae/ha or greater, or 5450 g ae/ha or greater).

In some embodiments, the auxin transport inhibitor (e.g., naptalam or 2,3,5-triiodobenzoic acid) or agriculturally acceptable salt or ester thereof is applied to vegetation or an area adjacent the vegetation or applied to soil or water to prevent the emergence or growth of vegetation in an amount of 5500 g ae/ha or less (e.g., 5450 g ae/ha or less, 5400 g ae/ha or less, 5350 g ae/ha or less, 5300 g ae/ha or less, 5250 g ae/ha or less, 5200 g ae/ha or less, 5150 g ae/ha or less, 5100 g ae/ha or less, 5050 g ae/ha or less, 5000 g ae/ha or less, 4950 g ae/ha or less, 4900 g ae/ha or less, 4850 g ae/ha or less, 4800 g ae/ha or less, 4750 g ae/ha or less, 4700 g ae/ha or less, 4650 g ae/ha or less, 4600 g ae/ha or less, 4550 g ae/ha or less, 4500 g ae/ha or less, 4450 g ae/ha or less, 4400 g ae/ha or less, 4350 g ae/ha or less, 4300 g ae/ha or less, 4250 g ae/ha or less, 4200 g ae/ha or less, 4150 g ae/ha or less, 4100 g ae/ha or less, 4050 g ae/ha or less, 4000 g ae/ha or less, 3950 g ac/la or less, 3900 g ae/ha or less, 3850 g ae/ha or less, 3800 g ae/ha or less, 3600 g ae/ha or less, 3400 g ae/ha or less, 3200 g ae/ha or less, 3000 g ae/ha or less, 2800 g ae/ha or less, 2600 g ae/ha or less, 2400 g ae/ha or less, 2200 g ae/ha or less, 2000 g ae/ha or less, 1900 g ae/ha or less, 1800 g ae/ha or less, 1700 g ae/ha or less, 1600 g ae/ha or less, 1500 g ae/ha or less, 1400 g ae/ha or less, 1300 g ae/ha or less, 1200 g ae/ha or less, 1100 g ae/ha or less, 1000 g ae/ha or less, 900 g ae/ha or less, 800 g ae/ha or less, 750 g ae/ha or less, 700 g ae/ha or less, 650 g ae/ha or less, 600 g ae/ha or less, 550 g ae/ha or less, 500 g ae/ha or less, 450 g ae/ha or less, 400 g ae/ha or less, 350 g ae/ha or less, 300 g ae/ha or less, 250 g ae/ha or less, 200 g ae/ha or less, or 150 g ae/ha or less).

The auxin transport inhibitor (e.g., naptalam or 2,3,5-triiodobenzoic acid) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the auxin transport inhibitor (e.g., naptalam or 2,3,5-triiodobenzoic acid) or agriculturally acceptable salt or ester thereof is applied to vegetation or an area adjacent the vegetation or applied to soil or water to prevent the emergence or growth of vegetation in an amount of from 140-5500 g ae/ha (e.g., 140-3000 g ae/ha, 3000-5500 g ae/ha, 140-2000 g ae/ha, 1400-3500 g ae/ha, 200-2000 g ae/ha, 200-3000 g ae/ha, 200-4000 g ae/ha, 250-2000 g ae/ha, 250-3000 g ae/ha, 250-4000 g ae/ha, 300-2000 g ae/ha, 300-3000 g ae/ha, 300-4000 g ae/ha, 500-2000 g ae/ha, 500-3000 g ae/ha, 500-4000 g ae/ha, or 1000-3000 g ae/ha). In certain embodiments, the auxin transport inhibitor (e.g., naptalam or 2,3,5-triiodobenzoic acid) or agriculturally acceptable salt or ester thereof is applied to vegetation or an area adjacent the vegetation or applied to soil or water to prevent the emergence or growth of vegetation in an amount of from 2000-3000 g ae/ha.

II. Compositions

A. Herbicidal Mixtures or Combinations

The (a) a pyridine carboxylic acid herbicide or an agriculturally acceptable N-oxide, salt, or ester thereof is mixed with or applied in combination with (b) a synthetic auxin herbicide, auxin transport inhibitor, agriculturally acceptable salts or esters thereof, or combinations thereof. In some embodiments, (a) and (b) can be provided in an amount sufficient to induce a herbicidal effect. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Tenth Edition, 2014, p. 487, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X * Y}{100}$$

wherein

X=effect in percent using (a) a pyridine carboxylic acid herbicide or an agriculturally acceptable N-oxide, salt, or ester thereof at an application rate a;

Y=effect in percent using (b) a synthetic auxin herbicide, auxin transport inhibitor, agriculturally acceptable salts or esters thereof, or combinations thereof at an application rate b;

E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of (a) a pyridine carboxylic acid herbicide or an agriculturally acceptable N-oxide, salt, or ester thereof and (b) a synthetic auxin herbicide, auxin transport inhibitor, agriculturally acceptable salts or esters thereof, or combinations thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the observed effect for undesired vegetation is at least 1%, at least 2%, at least 3%, at least 4%, at least 5%, at least 10%, at least 15%, at least 20%, or at least 25% greater than the effect (E) calculated according to the Colby equation (e.g., an observed effect of 96% would be 4% greater than an calculated effect (E) of 92%). In some embodiments, for undesired vegetation, the difference ($D_O$) between 100% and the observed effect is at least 5%, at least 10%, at least 15%, at least 20%, at least 25%, at least 30%, at least 35%, at least 40%, at least 45%, or at least 50% less than the difference ($D_E$) between 100% and the effect (E) calculated according to the Colby equation (e.g., an observed effect of 96% would produce a $D_O$ of 4%, a calculated effect (E) of 92% would produce a $D_E$ of 8%, and $D_O$ would be 50% less than or half of $D_E$).

In some embodiments, the weight ratio of (a) a pyridine carboxylic acid herbicide or an agriculturally acceptable N-oxide, salt, or ester thereof to (b) a synthetic auxin herbicide, or an agriculturally acceptable salt or ester thereof is 1:8000 or more (e.g., 1:7800 or more, 1:7600 or more, 1:7400 or more, 1:7200 or more, 1:7000 or more, 1:6750 or more, 1:6500 or more, 1:6250 or more, 1:6000 or more, 1:5750 or more, 1:5500 or more, 1:5250 or more, 1:5000 or more, 1:4500 or more, 1:4000 or more, 1:3500 or more, 1:3000 or more 1:2900 or more, 1:2800 or more, 1:2700 or more, 1:2600 or more, 1:2500 or more, 1:2400 or more, 1:2300 or more, 1:2200 or more, 1:2100 or more, 1:2000 or more, 1:1900 or more, 1:1800 or more, 1:1750 or more 1:1700 or more, 1:1600 or more, 1:1500 or more, 1:1400 or more, 1:1300 or more, 1:1250 or more, 1:1200 or more, 1:1100 or more, 1:1000 or more, 1:900 or more, 1:800 or more, 1:700 or more, 1:600 or more, 1:500 or more, 1:400 or more, 1:300 or more, 1:200 or more, 1:100 or more, 1:90 or more, 1:80 or more, 1:70 or more, 1:60 or more, 1:50 or more, 1:45 or more, 1:40 or more, 1:35 or more, 1:30 or more, 1:25 or more, 1:20 or more, 1:15 or more, 1:10 or more, 1:9 or more, 1:8 or more, 1:7 or more, 1:6 or more, 1:5 or more, 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.25:1 or more, 2.5:1 or more, 2.75:1 or more, 3:1 or more, 3.25:1 or more, 3.5:1 or more, 3.75:1 or more, 4:1 or more, 4.25:1 or more, 4.5:1 or more, 4.75:1 or more, 5:1 or more, 6:1 or more, 7:1 or more, 8:1 or more, 9:1 or more, 10:1 or more, 15:1 or more, 20:1 or more, 25:1 or more, 30:1 or more, 35:1 or more, 40:1 or more, 45:1 or more, 50:1 or more, 55:1 or more, 60:1 or more, 70:1 or more, 80:1 or more, 90:1 or more, 100:1 or more, 120:1 or more, 140:1 or more, 160:1 or more, 180:1 or more, 200:1 or more, 220:1 or more, 240:1 or more, 260:1 or more, or 280:1 or more).

In some embodiments, the weight ratio of (a) a pyridine carboxylic acid herbicide or an agriculturally acceptable N-oxide, salt, or ester thereof to (b) a synthetic auxin herbicide, or an agriculturally acceptable salt or ester thereof is 300:1 or less (e.g., 280:1 or less, 260:1 or less, 240:1 or less, 220:1 or less, 200:1 or less, 180:1 or less, 160:1 or less, 140:1 or less, 120:1 or less, 100:1 or less, 90:1 or less, 80:1 or less, 70:1 or less, 60:1 or less, 55:1 or less, 50:1 or less, 45:1 or less, 40:1 or less, 35:1 or less, 30:1 or less, 25:1 or less, 20:1 or less, 15:1 or less, 10:1 or less, 9:1 or less, 8:1 or less, 7:1 or less, 6:1 or less, 5:1 or less, 4.75:1 or less, 4.5:1 or less, 4.25:1 or less, 4:1 or less, 3.75:1 or less, 3.5:1 or less, 3.25:1 or less, 3:1 or less, 2.75:1 or less, 2.5:1 or less, 2.25:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, 1:4.75 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, 1:900 or less, 1:1000 or less, 1:1100 or less, 1:1200 or less, 1:1250 or less, 1:1300 or less, 1:1400 or less, 1:1500 or less, 1:1600 or less, 1:1700 or less, 1:1750 or less, 1:1800 or less, 1:1900 or less, 1:2000 or less, 1:2100 or less, 1:2200 or less, 1:2300 or less, 1:2400 or less, 1:2500 or less, 1:2600 or less, 1:2700 or less, 1:2800 or less, 1:2900 or less, 1:3000 or less, 1:3500 or less, 1:4000 or less, 1:4500 or less, 1:5000 or less, 1:5250 or less, 1:5500 or less, 1:5750 or less, 1:6000 or less, 1:6250 or less, 1:6500 or less, 1:6750 or less, 1:7000 or less, 1:7200 or less, 1:7400 or less, 1:7600 or less, or 1:7800 or less).

The weight ratio of (a) a pyridine carboxylic acid herbicide or an agriculturally acceptable N-oxide, salt, or ester thereof to (b) a synthetic auxin herbicide, or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) a synthetic auxin herbicide, or an agriculturally acceptable salt or ester thereof is from 1:8000 to 300:1 (e.g., from 1:7000 to 260:1, from 1:6000 to 220:1, from 1:5000 to 200:1, from 1:4000 to 160:1, from 1:3000 to 120:1, from 1:2000 to 100:1, from 1:1000 to 80:1, from 1:750 to 75:1, from 1:500 to 50:1, from 1:350 to 40:1, from 1:225 to 30:1, from 1:200 to 25:1, from 1:200 to 20:1, from 1:180 to 15:1, from 1:160 to 12:1, from 1:150 to 10:1, from 1:100 to 8:1, from 1:90 to 5:1, from 1:80 to 3.5:1, from 1:70 to 7:1, 1:3000 to 60:1, from 1:2500 to 50:1, from 1:2000 to 40:1, from 1:1500 to 30:1, from 1:1000 to 20:1, from 1:900 to 10:1, from 1:800 to 9:1, from 1:700 to 8:1, from 1:600 to 8:1, from 1:500 to 8:1, from 1:400 to 8:1, from 1:300 to 8:1, from 1:900 to 50:1, from 1:800 to 40:1, from 1:700 to 30:1, from 1:600 to 20:1, from 1:500 to 15:1, from 1:400 to 10:1, from 1:300 to 9:1, from 1:200 to 8:1, from 1:100 to 7:1, from 1:50 to 6:1, from 1:40 to 5:1, from 1:30 to 4:1, from 1:20 to 3:1, from 1:10 to 2:1, from 1:5 to 5:1, from 1:4 to 4:1, from 1:3 to 3:1, from 1:2 to 2:1 from 1:1.9 to 1.9:1, from 1:1.8 to 1.8:1, from 1:1.7 to 1.7:1, from 1:1.6 to 1.6:1, from 1:1.5 to 1.5:1, from 1:1.4 to 1.4:1, from 1:1.5 to 1.3:1, from 1:1.2 to 1.2:1, from 1:1.1 to 1.1:1, from 1:35 to 1:1, from 1:34 to 1:1, from 1:33 to 1:1, from 1:32 to 1:1, from 1:31 to 1:1, from 1:30 to 1:1, from 1:29 to 1:1, from 1:28 to 1:1, from 1:27 to 1:1, from 1:26 to 1:1, from 1:25 to 1:1, from 1:24 to 1:1, from 1:23 to 1:1, from 1:22 to 1:1, from 1:21 to 1:1, from 1:20 to 1:1, from 1:19 to 1:1, from 1:18 to 1:1, from 1:17 to 1:1, from 1:16 to 1:1, from 1:15 to 1:1, from 1:14 to 1:1, from 1:13 to 1:1, from 1:12 to 1:1, from 1:11 to 1:1, from 1:10 to 1:1, from 1:9 to 1:1, from 1:8 to 1:1, from 1:7 to 1:1, from 1:6 to 1:1, from 1:5 to 1:1, from 1:4 to 1:1, from 1:3 to 1:1, from 1:2 to 1:1, from 1:1.9 to 1:1, from 1:1.8 to 1:1, from 1:1.7 to 1:1, from 1:1.6 to 1:1, from 1:1.5 to 1:1, from 1:1.4 to 1:1, from 1:1.3 to 1:1, from 1:1.2 to 1:1, or from 1:1.1 to 1:1).

In some embodiments, (b) includes dicamba, clopyralid, fluroxypyr, aminocyclopyrachlor, or an agriculturally acceptable salt or ester thereof. In some embodiments, the weight ratio of (a) a pyridine carboxylic acid herbicide or an agriculturally acceptable N-oxide, salt, or ester thereof to (b) dicamba or an agriculturally acceptable salt or ester thereof is 1:800 or more (e.g., 1:700 or more, 1:600) or more, 1:500 or more, 1:400 or more, 1:300 or more, 1:200 or more, 1:100 or more, 1:90 or more, 1:80 or more, 1:70 or more, 1:60 or more, 1:50 or more, 1:45 or more, 1:40 or more, 1:35 or more, 1:30 or more, 1:25 or more, 1:20 or more, 1:15 or more, 1:10 or more, 1:9 or more, 1:8 or more, 1:7 or more, 1:6 or more, 1:5 or more, 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.1:1 or more, 2.2:1 or more, 2.3:1 or more, 2.4:1 or more, 2.5:1 or more, 2.6:1 or more, 2.7:1 or more, 2.8:1 or more, 2.9:1 or more, 3:1 or more, 3.2:1 or more, 3.4:1 or more, 3.6:1 or more, 3.8:1 or more, 4:1 or more, 4.2:1 or more, 4.4:1 or more, 4.6:1 or more, 4.8:1 or more, 5:1 or more, 5.1:1 or more, 5.2:1 or more, 5.3:1 or more, 5.4:1 or more, 5.5:1 or more, 5.6:1 or more, 5.7:1 or more, 0.5.8:1 or more, or 5.9:1 or more).

In some embodiments, the weight ratio of (a) a pyridine carboxylic acid herbicide or an agriculturally acceptable N-oxide, salt, or ester thereof to (b) dicamba, clopyralid, fluroxypyr, aminocyclopyrachlor, or an agriculturally acceptable salt or ester thereof is 6:1 or less (e.g., 5.9:1 or less, 5.8:1 or less, 5.7:1 or less, 5.6:1 or less, 5.5:1 or less, 5.4:1 or less, 5.3:1 or less, 5.2:1 or less, 5.1:1 or less, 5:1 or less, 4.8:1 or less, 4.6:1 or less, 4.4:1 or less, 4.2:1 or less, 4:1 or less, 3.8:1 or less, 3.6:1 or less, 3.4:1 or less, 3.2:1 or less, 3:1 or less, 2.9:1 or less, 2.8:1 or less, 2.7:1 or less, 2.6:1 or less, 2.5:1 or less, 2.4:1 or less, 2.3:1 or less, 2.2:1 or less, 2.1:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, 1:4.75 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, or 1:700 or less).

The weight ratio of (a) a pyridine carboxylic acid herbicide or an agriculturally acceptable N-oxide, salt, or ester thereof to (b) dicamba, clopyralid, fluroxypyr, aminocyclopyrachlor, or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) dicamba or an agriculturally acceptable salt or ester thereof is from 1:800 to 6:1 (e.g., from 1:400 to 5:1, from 1:400 to 3:1, from 1:200 to 4:1, from 1:160 to 1:5, from 1:100 to 3:1, from 1:80 to 1:2.5, from 1:50 to 2:1, from 1:25 to 1:1, from 1:40 to 6:1, from 1:20 to 4:1, from 1:20 to 3:1, from 1:10 to 2:1, from 1:2 to 2:1 from 1:1.9 to 1.9:1, from 1:1.8 to 1.8:1, from 1:1.7 to 1.7:1, from 1:1.6 to 1.6:1, from 1:1.5 to 1.5:1, from 1:1.4 to 1.4:1, from 1:1.5 to 1.3:1, from 1:1.2 to 1.2:1, from 1:1.1 to 1.1:1, from 1:35 to 1:1, from 1:34 to 1:1, from 1:33 to 1:1, from 1:32 to 1:1, from 1:31 to 1:1, from 1:30 to 1:1, from 1:29 to 1:1, from 1:28 to 1:1, from 1:27 to 1:1, from 1:26 to 1:1, from 1:25 to 1:1, from 1:24 to 1:1, from 1:23 to 1:1, from 1:22 to 1:1, from 1:21 to 1:1, from 1:20 to 1:1, from 1:19 to 1:1, from 1:18 to 1:1, from 1:17 to 1:1, from 1:16 to 1:1, from 1:15 to 1:1, from 1:14 to 1:1, from 1:13 to 1:1, from 1:12 to 1:1, from 1:11 to 1:1, from 1:10 to 1:1, from 1:9 to 1:1, from 1:8 to 1:1, from 1:7 to 1:1, from 1:6 to 1:1, from 1:5 to 1:1, from 1:4 to 1:1, from 1:3 to 1:1, from 1:2 to 1:1, from 1:1.9 to 1:1, from 1:1.8 to 1:1, from 1:1.7 to 1:1, from 1:1.6 to 1:1, from 1:1.5 to 1:1, from 1:1.4 to 1:1, from 1:1.3 to 1:1, from 1:1.2 to 1:1, or from 1:1.1 to 1:1).

In some embodiments, (b) includes aminopyralid, halauxifen, 4-amino-3-chloro-6-(4-chloro-2-fluoro-3-methoxyphenyl)-5-fluoro-2-pyridinecarboxylic acid, or an agriculturally acceptable salt or ester thereof. In some embodiments, the weight ratio of (a) a pyridine carboxylic acid herbicide or an agriculturally acceptable N-oxide, salt, or ester thereof to (b) aminopyralid, halauxifen, 4-amino-3-chloro-6-(4-chloro-2-fluoro-3-methoxyphenyl)-5-fluoro-2-pyridinecarboxylic acid, or an agriculturally acceptable salt or ester thereof is 1:300 or more (e.g., 1:200 or more, 1:100 or more, 1:90 or more, 1:80 or more, 1:70 or more, 1:60 or more, 1:50 or more, 1:45 or more, 1:40 or more, 1:35 or more, 1:30 or more, 1:25 or more, 1:20 or more, 1:15 or more, 1:10 or more, 1:9 or more, 1:8 or more, 1:7 or more, 1:6 or more, 1:5 or more, 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.1:1 or more, 2.2:1 or more, 2.3:1 or more, 2.4:1 or more, 2.5:1 or more, 2.6:1 or more, 2.7:1 or more, 2.8:1 or more, 2.9:1 or more, 3:1 or more, 3.1:1 or 3.2:1 or more, 3.3:1 or more, 3.4:1 or more, 3.5:1 or more, 3.6:1 or more, 3.7:1 or more, 3.8:1 or more, 3.9:1 or more, 4:1 or more, 4.1:1 or more, 4.2:1 or more, 4.3:1 or more, 4.4:1 or more, 4.5:1 or more, 4.6:1 or more, 4.7:1 or more, 4.8:1 or more, 4.9:1 or more, 5:1 or more, 6:1 or more, 7:1 or more, 8:1 or more, 9:1 or more, 10:1 or more, 15:1 or more, 20:1 or more, 25:1 or more, 30:1 or more, 35:1 or more, 40:1 or more, 50:1 or more, 60:1 or more, 70:1 or more, 80:1 or more, 90:1 or more, 100:1 or more, 120:1 or more, 140:1 or more, 160:1 or more, 180:1 or more, 200:1 or more, 220:1 or more, 240:1 or more, 260:1 or more, or 280:1 or more).

In some embodiments, the weight ratio of (a) a pyridine carboxylic acid herbicide or an agriculturally acceptable N-oxide, salt, or ester thereof to (b) aminopyralid, halauxifen, 4-amino-3-chloro-6-(4-chloro-2-fluoro-3-methoxyphenyl)-5-fluoro-2-pyridinecarboxylic acid, or an agriculturally acceptable salt or ester thereof is 300:1 or less (e.g., 280:1 or less, 260:1 or less, 240:1 or less, 220:1 or less, 200:1 or less, 180:1 or less, 160:1 or less, 140:1 or less, 120:1 or less, 100:1 or less, 90:1 or less, 80:1 or less, 70:1 or less, 60:1 or less, 50:1 or less, 40:1 or less, 30:1 or less, 20:1 or less, 10:1 or less, 9:1 or less, 8:1 or less, 7:1 or less, 6:1 or less, 5:1 or less, 4.9:1 or less, 4.8:1 or less, 4.7:1 or less, 4.6:1 or less, 4.5:1 or less, 4.4:1 or less, 4.3:1 or less, 4.2:1 or less, 4.1:1 or less, 4:1 or less, 3.9:1 or less, 3.8:1 or less, 3.7:1 or less, 3.6:1 or less, 3.5:1 or less, 3.4:1 or less, 3.3:1 or less, 3.2:1 or less, 3.1:1 or less, 3:1 or less, 2.9:1 or less, 2.8:1 or less, 2.7:1 or less, 2.6:1 or less, 2.5:1 or less, 2,4:1 or less, 2.3:1 or less, 2.2:1 or less, 2.1:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, 1:4.75 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, or 1:200 or less).

The weight ratio of (a) a pyridine carboxylic acid herbicide or an agriculturally acceptable N-oxide, salt, or ester thereof to (b) aminopyralid, halauxifen, 4-amino-3-chloro-6-(4-chloro-2-fluoro-3-methoxyphenyl)-5-fluoro-2-pyridinecarboxylic acid, or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) aminopyralid, halauxifen, 4-amino-3-chloro-6-(4-chloro-2-fluoro-3-methoxyphenyl)-5-fluoro-2-pyridinecarboxylic acid, or an agriculturally acceptable salt or ester thereof is from 1:300 to 300:1 (e.g., from 1:300 to 5:1, from 1:250 to 250:1, from 1:200 to 200:1, from 1:150 to 150:1, from 1:100 to 100:1, from 1:50 to 50:1, from 1:25 to 25:1, from 1:10 to 10:1, from 1:60 to 1:1, from 1:40 to 5:1, from 1:30 to 4:1, from 1:20 to 3:1, from 1:10 to 2:1, from 1:5 to 5:1, from 1:4 to 4:1, from 1:3 to 3:1, from 1:2 to 2:1 from 1:1.9 to 1.9:1, from 1:1.8 to 1.8:1, from 1:1.7 to 1.7:1, from 1:1.6 to 1.6:1, from 1:1.5 to 1.5:1, from 1:1.4 to 1.4:1, from 1:1.5 to 1.3:1, from 1:1.2 to 1.2:1, from 1:1.1 to 1.1:1, from 1:35 to 1:1, from 1:34 to 1:1, from 1:33 to 1:1, from 1:32 to 1:1, from 1:31 to 1:1, from 1:30 to 1:1, from 1:29 to 1:1, from 1:28 to 1:1, from 1:27 to 1:1, from 1:26 to 1:1, from 1:25 to 1:1, from 1:24 to 1:1, from 1:23 to 1:1, from 1:22 to 1:1, from 1:21 to 1:1, from 1:20 to 1:1, from 1:19 to 1:1, from 1:18 to 1:1, from 1:17 to 1:1, from 1:16 to 1:1, from 1:15 to 1:1, from 1:14 to 1:1, from 1:13 to 1:1, from 1:12 to 1:1, from 1:11 to 1:1, from 1:10 to 1:1, from 1:9 to 1:1, from 1:8 to 1:1, from 1:7 to 1:1, from 1:6 to 1:1, from 1:5 to 1:1, from 1:4 to 1:1, from 1:3 to 1:1, from 1:2 to 1:1, from 1:1.9 to 1:1, from 1:1.8 to 1:1, from 1:1.7 to 1:1, from 1:1.6 to 1:1, from 1:1.5 to 1:1, from 1:1.4 to 1:1, from 1:1.3 to 1:1, from 1:1.2 to 1:1, or from 1:1.1 to 1:1).

In some embodiments, (b) includes quinclorac, picloram, triclopyr, or an agriculturally acceptable salt or ester thereof. In some embodiments, the weight ratio of (a) a pyridine carboxylic acid herbicide or an agriculturally acceptable N-oxide, salt, or ester thereof to (b) quinclorac, picloram, triclopyr, or an agriculturally acceptable salt or ester thereof is 1:4480 or more (e.g., 1:4400 or more, 1:4200 or more, 1:4000 or more, 1:3750 or more, 1:3500 or more, 1:3250:1 or more, 1:3000 or more, 1:2750 or more, 1:2500 or more, 1:2250 or more, 1:2000 or more, 1:1500 or more, 1:1000 or more, 1:750 or more, 1:500 or more, 1:400 or more, 1:300 or more, 1:200 or more, 1:100 or more, 1:90 or more, 1:80 or more, 1:70 or more, 1:60 or more, 1:50 or more, 1:45 or more, 1:40 or more, 1:35 or more, 1:30 or more, 1:25 or more, 1:20 or more, 1:15 or more, 1:10 or more, 1:9 or more, 1:8 or more, 1:7 or more, 1:6 or more, 1:5 or more, 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.1:1 or more, 2.2:1 or more, 2.25:1 or more, 2.3:1 or more, 2,4:1 or more, 2.5:1 or more, 2.6:1 or more, 2.7:1 or more, 2.75:1 or more, 2.8:1 or more, 2.9:1 or more, 3:1 or more, 3.1:1 or more 3.2:1 or more, 3.3:1 or more, 3.4:1 or more, 3.5:1 or more, 3.6:1 or more, 3.7:1 or more, 3.8:1 or more, 3.9:1 or more, 4:1 or more, 4.1:1 or more, 4.2:1 or more, 4.3:1 or more, 4.4:1 or more, 4.5:1 or more, 4.6:1 or more, 4.7:1 or more, 4.8:1 or more, 4.9:1 or more, 5:1 or more, 5.25:1 or more, 5.5:1 or more, 5.75:1 or more, 6:1 or more, 7:1 or more, 9:1 or more, 9:1 or more, 10:1 or more, 15:1 or more, 20:1 or more, 25:1 or more, or 30:1 or more).

In some embodiments, the weight ratio of (a) a pyridine carboxylic acid herbicide or an agriculturally acceptable N-oxide, salt, or ester thereof to (b) quinclorac, picloram, triclopyr, or an agriculturally acceptable salt or ester thereof is 30:1 or less (e.g., 25:1 or less, 20:1 or less, 15:1 or less, 10:1 or less, 9:1 or less, 8:1 or less, 7:1 or less, 6:1 or less, 5.75:1 or less, 5.5:1 or less, 5.25:1 or less, 5:1 or less, 4.9:1 or less, 4.8:1 or less, 4.7:1 or less, 4.6:1 or less, 4.5:1 or less, 4.4:1 or less, 4.3:1 or less, 4.2:1 or less, 4.1:1 or less, 4:1 or less, 3.9:1 or less, 3.8:1 or less, 3.7:1 or less, 3.6:1 or less, 3.5:1 or less, 3.4:1 or less, 3.3:1 or less, 3.2:1 or less, 3.1:1 or less, 3:1 or less, 2.9:1 or less, 2.8:1 or less, 2.75:1 or less, 2.7:1 or less, 2.6:1 or less, 2.5:1 or less, 2,4:1 or less, 2.3:1 or less, 2.25:1 or less, 2.2:1 or less, 2.1:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, 1:4.75 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:200 or less, 1:300 or less, 1:400 or less, 1:500 or less, 1:750 or less, 1:1000 or less, 1:1500 or less, 1:2000 or less, 1:2250 or less, 1:2500 or less, 1:2750 or less, 1:3000 or less, 1:3250 or less, 1:3500 or less, 1:3750 or less, 1:4000 or less, 1:4200 or less, 1:4400 or less, or 1:4480 or less).

The weight ratio of (a) a pyridine carboxylic acid herbicide or an agriculturally acceptable N-oxide, salt, or ester thereof to (b) quinclorac, picloram, triclopyr, or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) quinclorac, picloram, triclopyr, or an agriculturally acceptable salt or ester thereof is from 1:4480 to 30:1 (e.g., from 1:4400 to 30:1, from 1:4000 to 27:1, from 1:3500 to 25:1, from 1:3000 to 20:1, from 1:2000 to 15:1, from 1:1000 to 10:1, from 1:750 to 7.5:1, from 1:500 to 5:1, 1:400 to 6:1, from 1:400 to 4:1, from 1:300 to 30:1, from 1:250 to 25:1, from 1:200 to 20:1, from 1:180 to 18:1, from 1:160 to 16:1, from 1:150 to 15:1, from 1:100 to 10:1, from 1:90 to 9:1, from 1:80 to 8:1, from 1:70 to 7:1, from 1:60 to 1:1, from 1:50 to 6:1, from 1:40 to 5:1, from 1:30 to 4:1, from 1:20 to 3:1, from 1:10 to 2:1, from 1:5 to 5:1, from 1:4 to 4:1, from 1:3 to 3:1, from 1:2 to 2:1 from 1:1.9 to 1.9:1, from 1:1.8 to 1.8:1, from 1:1.7 to 1.7:1, from 1:1.6 to 1.6:1, from 1:1.5 to 1.5:1, from 1:1.4 to 1.4:1, from 1:1.5 to 1.3:1, from 1:1.2 to 1.2:1, from 1:1.1 to 1.1:1, from 1:35 to 1:1, from 1:34 to 1:1, from 1:33 to 1:1, from 1:32 to 1:1, from 1:31 to 1:1, from 1:30 to 1:1, from 1:29 to 1:1, from 1:28 to 1:1, from 1:27 to 1:1, from 1:26 to 1:1, from 1:25 to 1:1, from 1:24 to 1:1, from 1:23 to 1:1, from 1:22 to 1:1, from 1:21 to 1:1, from 1:20 to 1:1, from 1:19 to 1:1, from 1:18 to 1:1, from 1:17 to 1:1, from 1:16 to 1:1, from 1:15 to 1:1, from 1:14 to 1:1, from 1:13 to 1:1, from 1:12 to 1:1, from 1:11 to 1:1, from 1:10 to 1:1, from 1:9 to 1:1, from 1:8 to 1:1, from 1:7 to 1:1, from 1:6 to 1:1, from 1:5 to 1:1, from 1:4 to 1:1, from 1:3 to 1:1, from 1:2 to 1:1, from 1:1.9 to 1:1, from 1:1.8 to 1:1, from 1:1.7 to 1:1, from 1:1.6 to 1:1, from 1:1.5 to 1:1, from 1:1.4 to 1:1, from 1:1.3 to 1:1, from 1:1.2 to 1:1, or from 1:1.1 to 1:1). In some embodiments, the active ingredients in the compositions disclosed herein consist of (a) a pyridine carboxylic acid herbicide or an agriculturally acceptable N-oxide, salt, or ester thereof and (b) a synthetic auxin herbicide or an agriculturally acceptable salt or ester thereof.

In some embodiments, the weight ratio of (a) a pyridine carboxylic acid herbicide or an agriculturally acceptable N-oxide, salt, or ester thereof in g ae/ha to (b) an auxin transport inhibitor, or an agriculturally acceptable salt or ester thereof in g ae/ha is 1:1000 or more (e.g., 1:900 or more, 1:800 or more, 1:700 or more, 1:600 or more, 1:500 or more, 1:400 or more, 1:300 or more, 1:200 or more, 1:100 or more, 1:90 or more, 1:80 or more, 1:70 or more, 1:60 or more, 1:50 or more, 1:45 or more, 1:40 or more, 1:35 or more, 1:30 or more, 1:25 or more, 1:20 or more, 1:15 or more, 1:10 or more, 1:9 or more, 1:8 or more, 1:7 or more, 1:6 or more, 1:5 or more, 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1:1.1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.25:1 or more, 2.5:1 or more, 2.75:1 or more, 3:1 or more, 3.25:1 or more, 3.5:1 or more, 3.75:1 or more, 4:1 or more, 4.25:1 or more, 4.5:1 or more, 4.75:1 or more, 5:1 or more, 6:1 or more, 7:1 or more, 8:1 or more, 9:1 or more, 10:1 or more, 15:1 or more, 20:1 or more, 25:1 or more, 30:1 or more, 35:1 or more, 40:1 or more, 45:1 or more, 50:1 or more, 55:1 or more, 60:1 or more, 65:1 or more, 70:1 or more, 75:1 or more, or 80:1 or more).

In some embodiments, the weight ratio of (a) a pyridine carboxylic acid herbicide or an agriculturally acceptable N-oxide, salt, or ester thereof in g ae/ha to (b) an auxin transport inhibitor, or an agriculturally acceptable salt or ester thereof in g ae/ha is 85:1 or less (e.g., 80:1 or less, 75:1 or less, 70:1 or less, 65:1 or less, 60:1 or less, 55:1 or less, 50:1 or less, 45:1 or less, 40:1 or less, 35:1 or less, 30:1 or less, 25:1 or less, 20:1 or less, 15:1 or less, 10:1 or less, 9:1 or less, 8:1 or less, 7:1 or less, 6:1 or less, 5:1 or less, 4.75:1 or less, 4.5:1 or less, 4.25:1 or less, 4:1 or less, 3.75:1 or less, 3.5:1 or less, 3.25:1 or less, 3:1 or less, 2.75:1 or less, 2.5:1 or less, 2.25:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, 1:4.75 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, or 1:900 or less).

The weight ratio of (a) a pyridine carboxylic acid herbicide or an agriculturally acceptable N-oxide, salt, or ester thereof in g ae/ha to (b) an auxin transport inhibitor, or an agriculturally acceptable salt or ester thereof in g ae/ha can range from any of the minimum ratios described above to any of the maximum values described above. For example, in some embodiments, the weight ratio of (a) a pyridine carboxylic acid herbicide or an agriculturally acceptable N-oxide, salt, or ester thereof in g ae/ha to (b) a auxin transport inhibitor, or an agriculturally acceptable salt or ester thereof in g ae/ha is from 1:1000 to 85:1 (e.g., 1:1000 to 20:1, from 1:900 to 10:1, from 1:800 to 9:1, from 1:700 to 8:1, from 1:600 to 8:1, from 1:500 to 8:1, from 1:400 to 8:1, from 1:300 to 8:1, from 1:900 to 50:1, from 1:800 to 40:1, from 1:700 to 30:1, from 1:600 to 20:1, from 1:500 to 15:1, from 1:400 to 10:1, from 1:300 to 9:1, from 1:200 to 12:1, from 1:100 to 12:1, from 1:50 to 12:1, from 1:20 to 12:1, from 1:10 to 12:1, from 1:2 to 12:1, from 1:1 to 12:1, from 1:2 to 6:1, from 1:1 to 6:1, from 1:100 to 7:1, from 1:50 to 6:1, from 1:40 to 5:1, from 1:30 to 4:1, from 1:20 to 3:1, from 1:10 to 2:1, from 1:5 to 5:1, from 1:4 to 4:1, from 1:3 to 3:1, from 1:2 to 2:1 from 1:1.9 to 1.9:1, from 1:1.8 to 1.8:1, from 1:1.7 to 1.7:1, from 1:1.6 to 1.6:1, from 1:1.5 to 1.5:1, from 1:1.4 to 1.4:1, from 1:1.3 to 1.3:1, from 1:1.2 to 1.2:1, from 1:1.1 to 1.1:1, from 1:35 to 1:1, from 1:34 to 1:1, from 1:33 to 1:1, from 1:32 to 1:1, from 1:31 to 1:1, from 1:30 to 1:1, from 1:29 to 1:1, from 1:28 to 1:1, from 1:27 to 1:1, from 1:26 to 1:1, from 1:25 to 1:1, from 1:24 to 1:1, from 1:23 to 1:1, from 1:22 to 1:1, from 1:21 to 1:1, from 1:20 to 1:1, from 1:19 to 1:1, from 1:18 to 1:1, from 1:17 to 1:1, from 1:16 to 1:1, from 1:15 to 1:1, from 1:14 to 1:1, from 1:13 to 1:1, from 1:12 to 1:1, from 1:11 to 1:1, from 1:10 to 1:1, from 1:9 to 1:1, from 1:8 to 1:1, from 1:7 to 1:1, from 1:6 to 1:1, from 1:5 to 1:1, from 1:4 to 1:1, from 1:3 to 1:1, from 1:2 to 1:1, from 1:1.9 to 1:1, from 1:1.8 to 1:1, from 1:1.7 to 1:1, from 1:1.6 to 1:1, from 1:1.5 to 1:1, from 1:1.4 to 1:1, from 1:1.3 to 1:1, from 1:1.2 to 1:1, or from 1:1.1 to 1:1).

In certain embodiments, the weight ratio of (a) a pyridine carboxylic acid herbicide or an agriculturally acceptable N-oxide, salt, or ester thereof in g ae/ha to (b) an auxin transport inhibitor, or an agriculturally acceptable salt or ester thereof in g ae/ha is from 1:200 to 12:1 (e.g., from 1:2 to 12:1, from 1:1 to 6:1, or from 1.25:1 to 5:1).

In some embodiments, the auxin transport inhibitor includes diflufenzopyr, naptalam, 2,3,5-triiodobenzoic acid, or an agriculturally acceptable salt or ester thereof.

In some examples, the active ingredients in the compositions disclosed herein consist of (a) a pyridine carboxylic acid herbicide or an agriculturally acceptable N-oxide, salt, or ester thereof and (b) an auxin transport inhibitor, or an agriculturally acceptable salt or ester thereof.

B. Formulations

The present disclosure also relates to formulations of the compositions and methods disclosed herein. In some embodiments, the formulation can be in the form of a single package formulation including both (a) a pyridine carboxylic acid herbicide or an agriculturally acceptable N-oxide, salt, or ester thereof and (b) a synthetic auxin herbicide, auxin transport inhibitor, agriculturally acceptable salts or esters thereof, or combinations thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, self-emulsifying formulations, pastes, dusts, and materials for spreading or granules.

In some embodiments, (a) a pyridine carboxylic acid herbicide or an agriculturally acceptable N-oxide, salt, or ester thereof and/or (b) a synthetic auxin herbicide, auxin transport inhibitor, agriculturally acceptable salts or esters thereof, or combinations thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the pyridine carboxylic acid herbicide or an agriculturally acceptable N-oxide, salt, or ester thereof. In some embodiments, the additive is premixed with the synthetic auxin herbicide, auxin transport inhibitor, agriculturally acceptable salts or esters thereof, or combinations thereof.

C. Other Actives

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: acetochlor, acifluorfen, aclonifen, acrolein, alachlor, allidochlor, alloxydim, allyl alcohol, alorac, ametridione, ametryn, amibuzin, amicarbazone, amidosulfuron, amiprofos-methyl, amitrole, ammonium sulfamate, anilofos, anisuron, asulam, atraton, atrazine, azafenidin, aziprotryne, barban, BCPC, beflubutamid, benazolin, bencarbazone, benfluralin, benfuresate, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, carbasulam, carbetamide, carboxazole, chlorprocarb, carfentrazone-ethyl, CDEA, CEPC, chlomethoxyfen, chloranocryl, chlorazifop, chlorazine, chlorbromuron, chlorbufam, chloreturon, chlorfenac, chlorfenprop, chlorflurazole, chlorflurenol, chloridazon, chlorimuron, chlormequat, chlornitrofen, chloropon, chlorotoluron, chloroxuron, chloroxynil, chlorpropham, chlorsulfuron, chlorthal, chlorthiamid, cinidon-ethyl, cinmethylin, cisanilide, clacyfos, clethodim, cliodinate, clodinafop, clofop, clomazone, cloproxydim, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dichlobenil, dichloralurea, dichlormate, diclofop, diclosulam, diethamquat, diethatyl, difenopenten, difenoxuron, difenzoquat, diflufenican, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, dithiopyr, diuron, DMPA, DNOC, DSMA, EBEP, eglinazine, endothal, epronaz, EPTC, esprocarb, etalfluralin, ethbenzamide, ethametsulfuron, ethidimuron, ethiolate, ethobenzamid, etobenzamid, ethofumesate, ethoxyfen, etinofen, etobenzanid, EXD, fenasulam, isoxadifen-ethyl, fenoxaprop, fenoxaprop-P, fenoxasulfone, fenthiaprop, fenquinotrione, fentrazamide, fenuron, ferrous sulfate, flamprop, flamprop-M, fluazifop, fluazifop-P, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halosafen, haloxydine, haloxyfop, haloxyfop-P, hexachloroacetone, hexaflurate, hexazinone, IAA, IBA, imazamethabenz, imazapic, imazapyr, imazaquin, indanofan, indaziflam, iodobonil, iodomethane, iodosulfuron, iodosulfuron-ethyl-sodium, iofensulfuron, ioxynil, ipazine, ipfencarbazone, iptymidam, isocarbamid, isocil, isomethiozin, isonoruron, isopolinate, isopropalin, isoproturon, isouron, isoxaben, isoxachlortole, isoxaflutole, isoxpyrifop, karbutilate, ketospiradox, kuicaoxi, lactofen, lenacil, linuron, MAA, MAMA, medinoterb, mefenacet, mefluidide, mesoprazine, mesosulfuron, mesotrione, metam, metamifop, metamitron, metazachlor, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, molinate, monalide, monisouron, monochloroacetic acid, monolinuron, monuron, morfamquat, MSMA, naproanilide, napropamide, napropamide-M, neburon, nicosulfuron, nipyraclofen, nitralin, nitrofen, nitrofluorfen, norflurazon, noruron, orbencarb, ortho-dichlorobenzene, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazoxyfen, pyributicarb, pyriclor, pyridafol, pyridate, pyrithiobac-sodium, pyroxasulfone, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil tcrbucarb, terbuchlor, terbumeton, terbuthylazine, terbutryn, tetrafluron, thenvlchlor, thiameturon, thiazafluron, thiazopyr, thidiazimin, thidiazuron, thiencarbazone-methyl, thifensulfuron, thifensulfurn-methyl, thiobencarb, tiafenacil, tiocarbazil, tioclorim, tolpyralate, topramezone, tralkoxydim, tri-allate, triafamone, triasulfuron, triaziflam, tribenuron, tribenuron-methyl, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, xylachlor, salts, esters, optically active isomers, and mixtures thereof.

In some embodiments, the additional pesticide or an agriculturally acceptable salt or ester thereof is provided in a premixed formulation with (a), (b), or combinations thereof. In some embodiments, the pyridine carboxylic acid herbicide or an agriculturally acceptable N-oxide, salt, or ester thereof is provided in a premixed formulation with an additional pesticide. In some embodiments, the synthetic auxin herbicide or an agriculturally acceptable salt or ester thereof is provided in a premixed formulation with an additional pesticide. In some embodiments, the auxin transport inhibitor or an agriculturally acceptable salt or ester thereof is provided in a premixed formulation with an additional pesticide.

D. Adjuvants/Carriers/Colorants/Adhesives

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, herbicide safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphate alcohol ethoxylate; natural primary alcohol ($C_{12}$-$C_{16}$) ethoxylate; di-sec-butylphenol EO-PO block copolymer polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); and PEG(400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro [4.5]decane, oxabetrinil, R29148, and N-phenyl-sulfonylbenzoic acid amides, as well as thereof agriculturally acceptable salts and, provided they have a carboxyl group, their agriculturally acceptable derivatives. In some embodiments, the safener can be cloquintocet or an ester or salt or ester thereof, such as cloquintocet (mexyl). In some embodiments, the safener can be dichlormid. In some embodiments, the safener is employed in rice, cereal, or corn/maize. For example, dichlormid or cloquintocet can be used to antagonize harmful effects of the compositions on rice, row crops, and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivatives, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono-, di-, and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions, can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

III. Methods of Use

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

In some embodiments, a method of controlling undesirable vegetation which comprises contacting the vegetation or the locus thereof with or applying to the soil or water to prevent the emergence or growth of vegetation any of the compositions is disclosed herein.

The compositions disclosed herein can be applied pre-emergence (before the emergence of undesirable vegetation) or post-emergence (i.e., during and/or after emergence of the undesirable vegetation). If desired, the compositions can be applied as an in-water application.

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by). In some embodiments, the compositions disclosed herein can be applied as dry formulations (e.g., granules, WDGs, etc.) into water.

In some embodiments, herbicidal activity is exhibited by the compounds of the mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, wheat, barley, triticale, rye, teff, oats, corn/maize, cotton, soy, sorghum, rice, sugarcane and range land (e.g., pasture grasses). In some embodiments, the undesirable vegetation is controlled in a row crop (e.g., corn/maize, sorghum, soybean, sunflower, sugarbeet, cotton, or spring rape/canola). In some embodiments, the compositions and methods disclosed herein can be used for controlling undesired vegetation in corn/maize, wheat, or a combination thereof.

The compositions and methods disclosed herein can be used for controlling undesired vegetation in non-crop areas. Exemplary non-crop areas include, but are not limited to, turfgrass, pastures, grasslands, rangelands, fallow land, rights-of-way, aquatic settings, tree and vine, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, crops that are resistant to photosystem II inhibitors, or crop plants that, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, aryloxyphenoxypropionates, acetyl CoA carboxylase (ACCase) inhibitors, imidazolinones, acetolactate synthase (ALS) inhibitors, 4-hydroxyphenyl-pyruvate dioxy genase (HPPD) inhibitors, protoporphyrinogen oxidase (PPO) inhibitors, triazines, bromoxynil, or combinations thereof. In some embodiments, the undesirable vegetation is controlled in glyphosate, glufosinate, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing single, multiple or stacked traits conferring tolerance to single or multiple chemistries and/or multiple modes of action. In some embodiments, the undesirable vegetation can be controlled in a crop that is ACCase-tolerant, ALS-tolerant, or a combination thereof. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

In some embodiments, the compositions disclosed herein can be used for controlling undesirable vegetation including grasses, broadleaf weeds, sedge weeds, and combinations thereof. In some embodiments, the compositions disclosed herein can be used for controlling undesirable vegetation including, but not limited to, Polygonum species such as wild buckwheat (Polygonum convolvulus), Amaranthus species such as pigweed (Amaranthus retroflexus), Chenopodium species such as common lambsquarters (Chenopodium album L.), Sida species such as prickly sida (Sida spinosa L.), Ambrosia species such as common ragweed (Ambrosia artemisiifolia), Cyperus species such as nutsedge (Cyperus esculentus), Setaria species such as giant foxtail (Setaria faberi), Sorghum species, Acanthospermum species, Anthemis species, Atriplex species, Brassica species, Cirsium species, Convolvulus species, Conyza species, such as horseweed (Conyza canadensis), Cassia species, Commelina species, Datura species, Euphorbia species, Geranium species, Galinsoga species, Ipomea species such as morning-glory, Lamium species, Malva species, Matricaria species, Persicaria species, Prosopis species, Rumex species, Sisymbrium species, Solanum species, Trifolium species, Xanthium species, Veronica species, Viola species such as wild pansy (Viola tricolor), common chickweed (Stellaria media), velvetleaf (Abutilon theophrasti), hemp sesbania (Sesbania exaltata Cory), Anoda cristata, Bidens pilosa, Brassica kaber, shepherd's purse (Capsella bursa-pastoris), cornflower (Centaurea cyanus or Cyanus segetum), hempnettle (Galeopsis tetrahit), cleavers (Galium aparine), Helianthus annuus, Desmodium tortuosum, kochia (Kochia scoparia), Medicago arabica, Mercurialis annua, Myosotis arvensis, common poppy (Papaver rhoeas), Raphanus raphanistrum, Russian thistle (Salsola kali or Salsola iberica), wild mustard (Sinapis arvensis), Sonchus arvensis, Thlaspi arvense, Tagetes minuta, Richardia brasiliensis, Plantago major, Plantago lanceolata, bird's-eye speedwell (Veronica persica) and speedwell.

In some embodiments, the undesirable vegetation includes velvetleaf (Abutilon theophrasti, ABUTH), blackgrass (Alopecurus myosuroides, ALOMY), pigweed (Amaranthus retroflexus, AMARE), wild oat (Avena fatua, AVEFA), Chinese kale (Brassica alboglabra, BRSAG), brown mustard (Brassica juncea, BRSJU), rutabaga (Brassica napus var. napobrassica, BRSNA), black mustard (Brassica nigra, BRSNI), spring rape (Brassica napus, BRSNN), spring rape—Roundup Ready (Brassica napus, BRSNN-RR), winter rape (Brassica napus, BRSNW), turnip (Brassica rapa, BRSRR), common lambsquarters (Chenopodium album L., CHEAL), Canadian thistle (Cirsium arvense, CIRAR), nutsedge (Cyperus esculentus, CYPES), large crabgrass (Digitaria sanguinalis, DIGSA), barnyardgrass (Echinochloa crusgalli, ECHCG), poinsettia (Euphorbia heterophylla, EPHHL), soybean (Glycine max, GLXMA), sunflower (Helianthus annus, HELAN), ivyleaf morningglory (Ipomoea hederacea, IPOHE), kochia (Kochia scoparia, KCHSC), mallow (Malva pusilla, MALPU), wild buckwheat (Polygonum convolvulus, POLCO), lady's-thumb (Polygonum persicaria, POLPE), wild radish (Raphanus raphanistrum, RAPRA), Russian thistle (Salsola iberica, SASKR), wild mustard (Sinapsis arvensis, SINAR), grain sorghum (Sorghum vulgare, SORVU), Indian hedge mustard (Sisymbrium orientale, SSYOR), common chickweed (Stellaria media, STEME), ivyleaved speedwell (Veronica hederifolia, VERHE) and wild pansy (Viola tricolor, VIOTR), or a combination thereof.

In some embodiments, the undesirable vegetation includes velvetleaf (Abutilon theophrasti, ABUTH), pigweed (AMARE, Amaranthus retroflexus), spring rape (Brassica napus, BRSNN), winter rape (BRSNW, Brassica napus), common lambsquarters (CHEAL, Chenopodium album L.), Canadian thistle (CIRAR, Cirsium arvense), nutsedge (Cyperus esculentus, CYPES), poinsettia (Euphorbia heterophylla, EPHHL), sunflower (Helianthus annus, HELAN), kochia (KCHSC, Kochia scoparia), mallow (MALPU, Malva pusilla), wild buckwheat (POLCO, Polygonum convolvulus), lady's thumb (POLPE, Polygonum persicaria), grain sorghum (Sorghum vulgare, SORVU), common chickweed (Stellaria media, STEME), and wild pansy (Viola tricolor, VIOTR), or a combination thereof.

The herbicidal compositions described herein can be used to control herbicide resistant or tolerant weeds. The methods employing the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxvacetamides, tetrazolinones), fatty acid and lipid synthesis inhibitors (e.g., phosphorodithioates, thiocarbamates, benzofuranes, chlorocarbonic acids), protoporphvrinogen oxidase (PPO) inhibitors (e.g., diphenylethers, N-phenylphthalimides, oxadiazoles, oxazolidinediones, phenylpyrazoles, pyrimidinediones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

By way of non-limiting illustration, examples of certain embodiments of the present disclosure are given below.

EXAMPLES

Example 1—Greenhouse Trials

Methodology—Evaluation of Postemergence Herbicidal Activity in Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical or experimental material were dissolved in a volume of 97:3 volume per volume (v/v) acetone/dimethyl sulfoxide (DMSO) to stock solutions. If the compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stock solutions of the formulated materials were prepared following the same procedure. Spray solutions of the synthetic auxins or auxin transport inhibitors and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 7 (soluble concentrate (SL) formulation) was combined with 2,4 D EHE (emulsifiable concentrate (EC)), MCPA EHE, Dichlorprop-P (as the potassium salt), mecoprop-P (as the potassium salt), dicamba-dimethylammonium (DMA) salt (as Banvel® 4S), clopyralid (as Lontrel™ 35A Herbicidal Concentrate), and fluroxypyr-MHE (EC) and applied to spring barley (HORVS), and winter wheat (TRZAW) and the phytotoxicity of the herbicidal compositions were measured. In addition, the efficacy of the herbicidal composition on pigweed (AMARE, *Amaranthus retroflexus*), winter rape (BRSNW, *Brassica napus*), common lambsquarters (CHEAL, *Chenopodium album* L.), Canadian thistle (CIRAR, *Cirsium arvense*), and kochia (KCHSC, *Kochia scoparia*) was evaluated. The results are summarized in Tables 1-7.

TABLE 1

Effect (% visual injury) of compound 7 and 2,4-D EHE on cereal weeds, spring barley (HORVS), and winter wheat (TRZAW).

| Application rate (g ae/ha) | compound 7<br>2,4-D EHE | 8.75<br>0 | 0<br>280 | 8.75<br>280 |
|---|---|---|---|---|
| AMARE | Obs | 70 | 30 | 95 |
|  | Exp | — | — | 79 |
|  | Δ |  |  | 16 |
| BRSNW | Obs | 58 | 85 | 100 |
|  | Exp | — | — | 94 |
|  | Δ |  |  | 6 |
| CIRAR | Obs | 25 | 73 | 88 |
|  | Exp | — | — | 79 |
|  | Δ |  |  | 8 |
| KCHSC | Obs | 55 | 10 | 73 |
|  | Exp | — | — | 60 |
|  | Δ |  |  | 13 |
| HORVS | Obs | 0 | 0 | 0 |
|  | Exp | — | — | 0 |
|  | Δ |  |  | 0 |
| TRZAW | Obs | 0 | 5 | 0 |
|  | Exp | — | — | 5 |
|  | Δ |  |  | −5 | g ae/ha = grams acid equivalent per hectare;
2,4-D EHE = 2-ethylhexyl (2,4-dichlorophenoxy)acetate;
AMARE = *Amaranthus retroflexus* (pigweed);
BRSNW = *Brassica napus* (winter rape);
CIRAR = *Cirsium arvense* (Canadian thistle);
KCHSC = *Kochia scoparia* (kochia);
HORVS = *Hordeum vulgare* (spring barley);
TRZAW = *Triticum aestivum* (winter wheat)

TABLE 2

Effect (% visual injury) of compound 7 and MCPA EHE on cereal weeds.

| Application rate (g ae/ha) | compound 7<br>MCPA EHE | 8.75<br>0 | 0<br>280 | 8.75<br>280 |
|---|---|---|---|---|
| AMARE | Obs | 70 | 35 | 84 |
|  | Exp | — | — | 81 |
|  | Δ |  |  | 4 |
| BRSNW | Obs | 58 | 73 | 98 |
|  | Exp | — | — | 88 |
|  | Δ |  |  | 9 |
| CHEAL | Obs | 60 | 75 | 94 |
|  | Exp | — | — | 90 |
|  | Δ |  |  | 4 |
| KCHSC | Obs | 55 | 0 | 78 |
|  | Exp | — | — | 55 |
|  | Δ |  |  | 23 |
| HORVS | Obs | 0 | 0 | 0 |
|  | Exp | — | — | 0 |
|  | Δ |  |  | 0 |

TABLE 2-continued

Effect (% visual injury) of compound 7 and MCPA EHE on cereal weeds.

| Application rate (g ae/ha) | compound 7<br>MCPA EHE | 8.75<br>0 | 0<br>280 | 8.75<br>280 |
|---|---|---|---|---|
| TRZAW | Obs | 0 | 3 | 0 |
|  | Exp | — | — | 3 |
|  | Δ |  |  | −3 | g ae/ha = grams acid equivalent per hectare
MCPA EHE = 2-ethylhexyl (4-chloro-2-methylphenoxy)acetate
AMARE = *Amaranthus retroflexus* (pigweed)
BRSNW = *Brassica napus* (winter rape)
CHEAL = *Chenopodium album* L. (common lambsquarters)
KCHSC = *Kochia scoparia* (kochia)
HORVS = *Hordeum vulgare* (spring barley)
TRZAW = *Triticum aestivum* (winter wheat)

TABLE 3

Effect (% visual injury) of compound 7 and Dichlorprop-P on cereal weeds.

| Application rate (g ae/ha) | compound 7<br>Dichlorprop-P | 8.75<br>0 | 0<br>280 | 8.75<br>280 |
|---|---|---|---|---|
| AMARE | Obs | 70 | 40 | 100 |
|  | Exp | — | — | 82 |
|  | Δ |  |  | 18 |
| BRSNW | Obs | 58 | 83 | 97 |
|  | Exp | — | — | 93 |
|  | Δ |  |  | 4 |
| CIRAR | Obs | 25 | 75 | 85 |
|  | Exp | — | — | 81 |
|  | Δ |  |  | 4 |
| HORVS | Obs | 0 | 0 | 0 |
|  | Exp | — | — | 0 |
|  | Δ |  |  | 0 |
| TRZAW | Obs | 0 | 0 | 0 |
|  | Exp | — | — | 0 |
|  | Δ |  |  | 0 | g ae/ha = grams acid equivalent per hectare
AMARE = *Amaranthus retroflexus* (pigweed)
BRSNW = *Brassica napus* (winter rape)
CIRAR = *Cirsium arvense* (Canadian thistle)
HORVS = *Hordeum vulgare* (spring barley)
TRZAW = *Triticum aestivum* (winter wheat)

TABLE 4

Effect (% visual injury) of compound 7 and mecoprop-P on cereal weeds.

| Application rate (g ae/ha) | compound 7<br>Mecoprop-P | 8.75<br>0 | 0<br>400 | 8.75<br>400 |
|---|---|---|---|---|
| AMARE | Obs | 70 | 58 | 99 |
|  | Exp | — | — | 87 |
|  | Δ |  |  | 11 |
| BRSNW | Obs | 58 | 88 | 98 |
|  | Exp | — | — | 95 |
|  | Δ |  |  | 3 |
| HORVS | Obs | 0 | 0 | 0 |
|  | Exp | — | — | 0 |
|  | Δ |  |  | 0 |
| TRZAW | Obs | 0 | 0 | 0 |
|  | Exp | — | — | 0 |
|  | Δ |  |  | 0 | g ae/ha = grams acid equivalent per hectare
AMARE = *Amaranthus retroflexus* (pigweed)
BRSNW = *Brassica napus* (winter rape)
HORVS = *Hordeum vulgare* (spring barley)
TRZAW = *Triticum aestivum* (winter wheat)

TABLE 5

Effect (% visual injury) of compound 7 and dicamba-DMA on cereal weeds.

| Application rate (g ae/ha) | compound 7<br>Dicamba-DMA | 8.75<br>0 | 0<br>140 | 8.75<br>140 |
|---|---|---|---|---|
| AMARE | Obs | 70 | 67 | 98 |
|  | Exp | — | — | 90 |
|  | Δ |  |  | 7 |
| BRSNW | Obs | 58 | 40 | 84 |
|  | Exp | — | — | 75 |
|  | Δ |  |  | 9 |
| HORVS | Obs | 0 | 0 | 0 |
|  | Exp | — | — | 0 |
|  | Δ |  |  | 0 |
| TRZAW | Obs | 0 | 0 | 0 |
|  | Exp | — | — | 0 |
|  | Δ |  |  | 0 | g ae/ha = grams acid equivalent per hectare
AMARE = *Amaranthus retroflexus* (pigweed)
BRSNW = *Brassica napus* (winter rape)
HORVS = *Hordeum vulgare* (spring barley)
TRZAW = *Triticum aestivum* (winter wheat)

TABLE 6

Effect (% visual injury) of compound 7 and clopyralid on cereal weeds.

| Application rate (g ae/ha) | compound 7<br>clopyralid | 8.75<br>0 | 0<br>100 | 8.75<br>100 |
|---|---|---|---|---|
| AMARE | Obs | 70 | 3 | 89 |
|  | Exp | — | — | 71 |
|  | Δ |  |  | 18 |
| BRSNW | Obs | 58 | 0 | 80 |
|  | Exp | — | — | 58 |
|  | Δ |  |  | 23 |
| CHEAL | Obs | 60 | 0 | 85 |
|  | Exp | — | — | 60 |
|  | Δ |  |  | 25 |
| CIRAR | Obs | 25 | 85 | 93 |
|  | Exp | — | — | 89 |
|  | Δ |  |  | 4 |
| HORVS | Obs | 0 | 5 | 0 |
|  | Exp | — | — | 5 |
|  | Δ |  |  | −5 |
| TRZAW | Obs | 0 | 3 | 0 |
|  | Exp | — | — | 3 |
|  | Δ |  |  | −3 | g ae/ha = grams acid equivalent per hectare
AMARE = *Amaranthus retroflexus* (pigweed)
BRSNW = *Brassica napus* (winter rape)
CHEAL = *Chenopodium album* L. (common lambsquarters)
CIRAR = *Cirsium arvense* (Canadian thistle)
HORVS = *Hordeum vulgare* (spring barley)
TRZAW = *Triticum aestivum* (winter wheat)

TABLE 7

Effect (% visual injury) of compound 7 and fluroxypyr-MHE on cereal weeds.

| Application rate (g ae/ha) | compound 7<br>Fluroxypyr-MHE | 5<br>0 | 10<br>0 | 0<br>70 | 5<br>70 | 10<br>70 |
|---|---|---|---|---|---|---|
| CHEAL | Obs | 80 | 100 | 10 | 97 | 100 |
|  | Exp | — | — | — | 82 | 100 |
|  | Δ |  |  |  | 15 | 0 |
| CIRAR | Obs | 50 | 65 | 10 | 70 | 85 |
|  | Exp | — | — | — | 55 | 69 |
|  | Δ |  |  |  | 15 | 17 |

TABLE 7-continued

Effect (% visual injury) of compound
7 and fluroxypyr-MHE on cereal weeds.

| Application rate (g ae/ha) | compound 7 | 5 | 10 | 0 | 5 | 10 |
|---|---|---|---|---|---|---|
| | Fluroxypyr-MHE | 0 | 0 | 70 | 70 | 70 |
| HORVS | Obs | 0 | 15 | 20 | 10 | 25 |
| | Exp | — | — | — | 20 | 32 |
| | Δ | | | | −10 | −7 | g ae/ha = grams acid equivalent per hectare
fluroxypyr-MHE = fluroxypyr methylheptyl ester = fluroxypyr-meptyl
CHEAL = *Chenopodium album* L. (common lambsquarters)
CIRAR = *Cirsium arvense* (Canadian thistle)
HORVS = *Hordeum vulgare* (spring barley)

Example 2—Patio Trials

Methodology—Evaluation of Postemergence Herbicidal Activity in Crops

Seeds of the desired test plant species were planted in Sun Gro MetroMix® 306 planting mix, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied to the seeds. The plants were grown for 7-36 days (d) on a fenced, open-air patio. Nutrients and water were added on a regular basis. The plants were employed for testing when they reached the second or third true leaf stage.

Weighed amounts of technical or experimental material were dissolved in a volume of 97:3 volume per volume (v/v) acetone/dimethyl sulfoxide (DMSO) to stock solutions. If the compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stock solutions of the formulated materials were prepared following the same procedure. Spray solutions of the synthetic auxins or auxin transport inhibitors and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters (m²) at a spray height of 18 inches (43 centimeters (cm)) above average plant canopy. Control plants were sprayed in the same manner with the solvent blank.

The treated plants and control plants were placed back on the patio and watered by sub-irrigation to prevent wash-off of the test compounds. Temperatures and photoperiods were dependent on the natural weather conditions during the trials. Weather conditions during trials were conducive for plant growth and development. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 7 (SL) was combined with 2,4 D EHE (EC), MCPA EHE, and halauxifen-methyl (as Arylex™; suspension concentrate (SC)) and applied to winter wheat (TRZAW) and the phytotoxicity of the herbicidal compositions were measured. In addition, the efficacy of the herbicidal composition on pigweed (AMARE, *Amaranthus retroflexus*) and kochia (KCHSC, *Kochia scoparia*) was evaluated. The results are summarized in Tables 8-10.

TABLE 8

Effect (% visual injury) of compound 7
and halauxifen-methyl on cereal weeds.

| Application rate (g ae/ha) | compound 7 | 8.75 | 0 | 8.75 |
|---|---|---|---|---|
| | halauxifen-methyl | 0 | 8.75 | 8.75 |
| KCHSC | Obs | 5 | 60 | 73 |
| | Exp | — | — | 62 |
| | Δ | | | 11 |
| TRZAW | Obs | 5 | 10 | 8 |
| | Exp | — | — | 15 |
| | Δ | | | −7 | g ae/ha = grams acid equivalent per hectare
KCHSC = *Kochia scoparia* (kochia)
TRZAW = *Triticum aestivum* (winter wheat)

TABLE 9

Effect (% visual injury) of compound
7 and 2,4-D EHE on cereal weeds.

| Application rate (g ae/ha) | compound 7 | 8.75 | 17.5 | 0 | 8.75 | 17.5 |
|---|---|---|---|---|---|---|
| | 2,4-D EHE | 0 | 0 | 280 | 280 | 280 |
| AMARE | Obs | 30 | 40 | 50 | 100 | 100 |
| | Exp | — | — | — | 65 | 70 |
| | Δ | | | | 35 | 30 |
| KCHSC | Obs | 5 | 0 | 10 | 20 | 60 |
| | Exp | — | — | — | 15 | 10 |
| | Δ | | | | 6 | 50 | g ae/ha = grams acid equivalent per hectare
2,4-D EHE = 2-ethylhexyl (2,4-dichlorophenoxy)acetate
AMARE = *Amaranthus retroflexus* (pigweed)
KCHSC = *Kochia scoparia* (kochia)

TABLE 10

Effect (% visual injury) of compound
7 and MCPA EHE on cereal weeds.

| Application rate (g ae/ha) | compound 7 | 8.75 | 17.5 | 0 | 8.75 | 17.5 |
|---|---|---|---|---|---|---|
| | MCPA EHE | 0 | 0 | 280 | 280 | 280 |
| KCHSC | Obs | 5 | 0 | 20 | 60 | 30 |
| | Exp | — | — | — | 24 | 20 |
| | Δ | | | | 36 | 10 |
| TRZAW | Obs | 5 | 0 | 0 | 5 | 0 |
| | Exp | — | — | — | 5 | 0 |
| | Δ | | | | 0 | 0 | g ae/ha = grams acid equivalent per hectare
MCPA EHE = 2-ethylhexyl (4-chloro-2-methylphenoxy)acetate
KCHSC = *Kochia scoparia* (kochia)
TRZAW = *Triticum aestivum* (winter wheat)

Example 3—Greenhouse Trials

Following the protocol in Example 1, compound 1 and compound 2 were combined with 2,4 D EHE (EC) and applied to kochia (KCHSC, *Kochia scoparia*) and the phytotoxicity of the herbicidal compositions was measured. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 11-12.

TABLE 11

Effect (% visual injury) of compound 1 and 2,4-D EHE on cereal weeds.

| Application rate (g ae/ha) | compound 1 | 8.75 | 0 | 8.75 |
|---|---|---|---|---|
|  | 2,4-D EHE | 0 | 280 | 280 |
| KCHSC | Obs | 43 | 10 | 75 |
|  | Exp | — | — | 48 |
|  | Δ |  |  | 27 | g ae/ha = grams acid equivalent per hectare
2,4-D EHE = 2-ethylhexyl (2,4-dichlorophenoxy)acetate
KCHSC = *Kochia scoparia* (kochia)

TABLE 12

Effect (% visual injury) of compound 2 and 2,4-D EHE on cereal weeds.

| Application rate (g ae/ha) | compound 2 | 8.75 | 0 | 8.75 |
|---|---|---|---|---|
|  | 2,4-D EHE | 0 | 280 | 280 |
| KCHSC | Obs | 55 | 10 | 68 |
|  | Exp | — | — | 60 |
|  | Δ |  |  | 8 | g ae/ha = grams acid equivalent per hectare
2,4-D EHE = 2-ethylhexyl (2,4-dichlorophenoxy)acetate
KCHSC = *Kochia scoparia* (kochia)

Example 4—Field Trials

Small plot field trials were established in Canada to evaluate efficacy and crop safety of Compound 7 with 2,4-D EHE. Trials were established as randomized complete blocks with 3-4 replicates. Individual plots were 2-3 meters (m) wide and 8-10 m long. Applications were made with backpack or tractor-mounted sprayers delivering a spray volume output of 100 liters per hectare (L/ha) using pressurized carbon dioxide ($CO_2$) as a propellant. Compound 7 was combined with 2,4 D EHE (660 g ae/L EC formulation) and applied to spring wheat (TRZAS), and the phytotoxicity of the herbicidal compositions was measured. In addition, the efficacy of the herbicidal composition on Canadian thistle (CIRAR, *Cirsium arvense*), kochia (KCHSC, *Kochia scoparia*), mallow (MALPU, *Malva pusilla*), wild buckwheat (POLCO, *Polygonum convolvulus*), and lady's thumb (POLPE, *Polygonum persicaria*) was evaluated. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Table 13.

TABLE 13

Effect (% visual injury) of compound 7 and 2,4-D EHE on cereal weeds.

| Application rate (g ae/ha) | compound 7 | 35 | 0 | 35 |
|---|---|---|---|---|
|  | 2,4-D EHE | 0 | 560 | 560 |
| KCHSC | 46-64 DAA | Obs | 62 | 25 | 81 |
|  |  | Exp | — | — | 72 |
|  |  | Δ |  |  | 10 |
| POLCO | 15 DAA | Obs | 50 | 51 | 84 |
|  |  | Exp | — | — | 76 |
|  |  | Δ |  |  | 9 |
| POLPE | 14-16 DAA | Obs | 20 | 55 | 71 |
|  |  | Exp | — | — | 64 |
|  |  | Δ |  |  | 7 |
| CIRAR | 46-64 DAA | Obs | 20 | 65 | 80 |
|  |  | Exp | — | — | 72 |
|  |  | Δ |  |  | 8 |
| MALPU | 26-33 DAA | Obs | 15 | 74 | 90 |
|  |  | Exp | — | — | 78 |
|  |  | Δ |  |  | 12 |
| TRZAS | 6-8 DAA | Obs | 3 | 3 | 5 |
|  |  | Exp | — | — | 6 |
|  |  | Δ |  |  | −1 |
| TRZAS | 14-16 DAA | Obs | 3 | 0 | 3 |
|  |  | Exp | — | — | 3 |
|  |  | Δ |  |  | 0 | g ae/ha = grams acid equivalent per hectare
DAA = days after exposure
2,4-D EHE = 2-ethylhexyl (2,4-dichlorophenoxy)acetate
KCHSC = *Kochia scoparia* (kochia)
POLCO = *Polygonum convolvulus* (wild buckwheat)
POLPE = *Polygonum persicaria* (lady's thumb)
CIRAR = *Cirsium arvense* (Canadian thistle)
MALPU = *Malva pusilla* (mallow)
TRZAS = *Triticum aestivum* (spring wheat)

Example 5—Greenhouse Trials

Following the protocol in Example 1, the herbicide 2,4 D EHE (EC) was combined with compound 1, compound 8, compound 9, compound 10, compound 11, compound 12, compound 13, compound 14, compound 15, and compound 16 and applied to winter wheat (TRZAW) and maize (ZEAMX), and the phytotoxicity of the herbicidal compositions was measured. In addition, the efficacy of the herbicidal compositions on velvetleaf (*Abutilon theophrasti*, ABUTH), pigweed (AMARE, *Amaranthus retroflexus*), spring rape (*Brassica napus*, BRSNN), common lambsquarters (*Chenopodium album* L., CHEAL), Canadian thistle (*Cirsium arvense*, CIRAR), nutsedge (*Cyperus esculentus*, CYPES), poinsettia (*Euphorbia heterophylla*, EPHHL), sunflower (*Helianthus annus*, HELAN), wild buckwheat (*Polygonum convolvulus*, POLCO), grain sorghum (*Sorghum vulgare*, SORVU), common chickweed (*Stellaria media*, STEME), and wild pansy (*Viola tricolor*, VIOTR) was evaluated. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 14-23.

TABLE 14

Effect (% visual injury) of compound 1 and 2,4-D EHE on weeds.

| Application rate (g ae/ha) | compound 1 2,4-D EHE | | 5 0 | 0 140 | 5 140 |
|---|---|---|---|---|---|
| VIOTR | Obs | | 25 | 35 | 70 |
| | Exp | | — | — | 51 |
| | Δ | | | | 19 |
| CIRAR | Obs | | 20 | 50 | 78 |
| | Exp | | — | — | 60 |
| | Δ | | | | 18 |
| BRSNN | Obs | | 60 | 60 | 96 |
| | Exp | | — | — | 84 |
| | Δ | | | | 12 |
| SORVU | Obs | | 13 | 0 | 35 |
| | Exp | | — | — | 13 |
| | Δ | | | | 23 |
| CYPES | Obs | | 25 | 0 | 70 |
| | Exp | | — | — | 25 |
| | Δ | | | | 45 | g ae/ha = grams acid equivalent per hectare
2,4-D EHE = 2-ethylhexyl (2,4-dichlorophenoxy)acetate
VIOTR = *Viola tricolor* (wild pansy)
CIRAR = *Cirsium arvense* (Canadian thistle)
BRSNN = *Brassica napus* (spring rape)
SORVU = *Sorghum vulgare* (grain sorghum)
CYPES = *Cyperus esculentus* (nutsedge)

TABLE 15

Effect (% visual injury) of compound 8 and 2,4-D EHE on weeds.

| Application rate (g ae/ha) | compound 8 2,4-D EHE | | 5 0 | 0 140 | 5 140 |
|---|---|---|---|---|---|
| VIOTR | Obs | | 10 | 35 | 63 |
| | Exp | | — | — | 42 |
| | Δ | | | | 21 |
| CIRAR | Obs | | 30 | 50 | 80 |
| | Exp | | — | — | 65 |
| | Δ | | | | 15 |
| BRSNN | Obs | | 63 | 60 | 93 |
| | Exp | | — | — | 85 |
| | Δ | | | | 8 |
| EPHHL | Obs | | 84 | 35 | 100 |
| | Exp | | — | — | 90 |
| | Δ | | | | 10 |
| ABUTH | Obs | | 20 | 55 | 70 |
| | Exp | | — | — | 66 |
| | Δ | | | | 4 |
| AMARE | Obs | | 78 | 95 | 100 |
| | Exp | | — | — | 99 |
| | Δ | | | | 1 |
| STEME | Obs | | 45 | 63 | 80 |
| | Exp | | — | — | 79 |
| | Δ | | | | 1 |
| TRZAW | Obs | | 5 | 0 | 5 |
| | Exp | | — | — | 5 |
| | Δ | | | | 0 | g ae/ha = grains acid equivalent per hectare
2,4-D EHE = 2-ethylhexyl (2,4-dichlorophenoxy)acetate
VIOTR = *Viola tricolor* (wild pansy)
CIRAR = *Cirsium arvense* (Canadian thistle)
BRSNN = *Brassica napus* (spring rape)
EPHHL = *Euphorbia heterophylla* (poinsettia)
ABUTH = *Abutilon theophrasti* (velvetleaf)
AMARE = *Amaranthus retroflexus* (pigweed)
STEME = *Stellaria media* (common chickweed)
TRZAW = *Triticum aestivum* (winter wheat)

TABLE 16

Effect (% visual injury) of compound 9 and 2,4-D EHE on weeds.

| Application rate (g ae/ha) | compound 9 2,4-D EHE | | 5 0 | 0 140 | 5 140 |
|---|---|---|---|---|---|
| VIOTR | Obs | | 15 | 35 | 70 |
| | Exp | | — | — | 45 |
| | Δ | | | | 25 |
| CIRAR | Obs | | 10 | 50 | 75 |
| | Exp | | — | — | 55 |
| | Δ | | | | 20 |
| BRSNN | Obs | | 10 | 60 | 80 |
| | Exp | | — | — | 64 |
| | Δ | | | | 16 |
| EPHHL | Obs | | 60 | 35 | 83 |
| | Exp | | — | — | 74 |
| | Δ | | | | 9 |
| CYPES | Obs | | 0 | 0 | 40 |
| | Exp | | — | — | 0 |
| | Δ | | | | 40 |
| POLCO | Obs | | 25 | 55 | 70 |
| | Exp | | — | — | 66 |
| | Δ | | | | 4 |
| TRZAW | Obs | | 0 | 0 | 5 |
| | Exp | | — | — | 0 |
| | Δ | | | | 5 |
| ZEAMX | Obs | | 0 | 0 | 5 |
| | Exp | | — | — | 0 |
| | Δ | | | | 5 | g ae/ha = grams acid equivalent per hectare
2,4-D EHE = 2-ethylhexyl (2,4-dichlorophenoxy)acetate
VIOTR = *Viola tricolor* (wild pansy)
CIRAR = *Cirsium arvense* (Canadian thistle)
BRSNN = *Brassica napus* (spring rape)
EPHHL = *Euphorbia heterophylla* (poinsettia)
CYPES = *Cyperus esculentus* (nutsedge)
POLCO = *Polygonum convolvulus* (wild buckwheat)
TRZAW = *Triticum aestivum* (winter wheat)
ZEAMX = *Zea mays* (maize)

TABLE 17

Effect (% visual injury) of compound 10 and 2,4-D EHE on weeds.

| Application rate (g ae/ha) | compound 10 2,4-D EHE | | 5 0 | 0 140 | 5 140 |
|---|---|---|---|---|---|
| VIOTR | Obs | | 25 | 35 | 60 |
| | Exp | | — | — | 51 |
| | Δ | | | | 9 |
| CIRAR | Obs | | 15 | 50 | 84 |
| | Exp | | — | — | 58 |
| | Δ | | | | 27 |
| BRSNN | Obs | | 15 | 60 | 96 |
| | Exp | | — | — | 66 |
| | Δ | | | | 30 |
| SORVU | Obs | | 5 | 0 | 10 |
| | Exp | | — | — | 5 |
| | Δ | | | | 5 |
| EPHHL | Obs | | 75 | 35 | 93 |
| | Exp | | — | — | 84 |
| | Δ | | | | 9 |
| CYPES | Obs | | 5 | 0 | 10 |
| | Exp | | — | — | 5 |
| | Δ | | | | 5 |
| ABUTH | Obs | | 15 | 55 | 84 |
| | Exp | | — | — | 62 |
| | Δ | | | | 22 |
| POLCO | Obs | | 10 | 55 | 88 |
| | Exp | | — | — | 60 |
| | Δ | | | | 28 |
| STEME | Obs | | 70 | 63 | 88 |
| | Exp | | — | — | 89 |
| | Δ | | | | −1 |

TABLE 17-continued

Effect (% visual injury) of compound 10 and 2,4-D EHE on weeds.

| Application rate (g ae/ha) | compound 10 | 5 | 0 | 5 |
|---|---|---|---|---|
| | 2,4-D EHE | 0 | 140 | 140 |
| TRZAW | Obs | 5 | 0 | 0 |
| | Exp | — | — | 5 |
| | Δ | | | −5 | g ae/ha = grams acid equivalent per hectare
2,4-D EHE = 2-ethylhexyl (2,4-dichlorophenoxy)acetate
VIOTR = *Viola tricolor* (wild pansy)
CIRAR = *Cirsium arvense* (Canadian thistle)
BRSNN = *Brassica napus* (spring rape)
SORVU = *Sorghum vulgare* (grain sorghum)
EPHHL = *Euphorbia heterophylla* (poinsettia)
CYPES = *Cyperus esculentus* (nutsedge)
ABUTH = *Abutilon theophrasti* (velvetleaf)
POLCO = *Polygonum convolvulus* (wild buckwheat)
STEME = *Stellaria media* (common chickweed)
TRZAW = *Triticum aestivum* (winter wheat)

TABLE 18

Effect (% visual injury) of compound 11 and 2,4-D EHE on weeds.

| Application rate (g ae/ha) | compound 11 | 5 | 0 | 5 |
|---|---|---|---|---|
| | 2,4-D EHE | 0 | 140 | 140 |
| VIOTR | Obs | 10 | 35 | 70 |
| | Exp | — | — | 42 |
| | Δ | | | 29 |
| STEME | Obs | 40 | 63 | 85 |
| | Exp | — | — | 78 |
| | Δ | | | 8 |
| CIRAR | Obs | 5 | 50 | 80 |
| | Exp | — | — | 53 |
| | Δ | | | 28 |
| BRSNN | Obs | 10 | 60 | 93 |
| | Exp | — | — | 64 |
| | Δ | | | 29 |
| SORVU | Obs | 5 | 0 | 30 |
| | Exp | — | — | 5 |
| | Δ | | | 25 |
| EPHHL | Obs | 25 | 35 | 65 |
| | Exp | — | — | 51 |
| | Δ | | | 15 |
| CYPES | Obs | 0 | 0 | 15 |
| | Exp | — | — | 0 |
| | Δ | | | 15 |
| POLCO | Obs | 10 | 55 | 100 |
| | Exp | — | — | 60 |
| | Δ | | | 41 |
| TRZAW | Obs | 10 | 0 | 0 |
| | Exp | — | — | 10 |
| | Δ | | | −10 | g ae/ha = grams acid equivalent per hectare
2,4-D EHE = 2-ethylhexyl (2,4-dichlorophenoxy)acetate
VIOTR = *Viola tricolor* (wild pansy)
STEME = *Stellaria media* (common chickweed)
CIRAR = *Cirsium arvense* (Canadian thistle)
BRSNN = *Brassica napus* (spring rape)
SORVU = *Sorghum vulgaore* (grain sorghum)
EPHHL = *Euphorbia heterophylla* (poinsettia)
CYPES = *Cyperus esculentus* (nutsedge)
POLCO = *Polygonum convolvulus* (wild buckwheat)
TRZAW = *Triticum aestivum* (winter wheat)

TABLE 19

Effect (% visual injury) of compound 12 and 2,4-D EHE on weeds.

| Application rate (g ae/ha) | compound 12 | 5 | 0 | 5 |
|---|---|---|---|---|
| | 2,4-D EHE | 0 | 140 | 140 |
| VIOTR | Obs | 18 | 35 | 68 |
| | Exp | — | — | 46 |
| | Δ | | | 21 |
| CIRAR | Obs | 10 | 50 | 80 |
| | Exp | — | — | 55 |
| | Δ | | | 25 |
| BRSNN | Obs | 50 | 60 | 95 |
| | Exp | — | — | 80 |
| | Δ | | | 15 |
| EPHHL | Obs | 35 | 35 | 80 |
| | Exp | — | — | 58 |
| | Δ | | | 22 |
| CYPES | Obs | 5 | 0 | 68 |
| | Exp | — | — | 5 |
| | Δ | | | 63 |
| ABUTH | Obs | 10 | 55 | 90 |
| | Exp | — | — | 60 |
| | Δ | | | 31 |
| CHEAL | Obs | 84 | 73 | 96 |
| | Exp | — | — | 95 |
| | Δ | | | 1 |
| SORVU | Obs | 0 | 0 | 10 |
| | Exp | — | — | 0 |
| | Δ | | | 10 |
| TRZAW | Obs | 0 | 0 | 5 |
| | Exp | — | — | 0 |
| | Δ | | | 5 |
| ZEAMX | Obs | 0 | 0 | 0 |
| | Exp | — | — | 0 |
| | Δ | | | 0 | g ae/ha = grams acid equivalent per hectare
2,4-D EHE = 2-ethylhexyl (2,4-dichlorophenoxy)acetate
VIOTR = *Viola tricolor* (wild pansy)
CIRAR = *Cirsium arvense* (Canadian thistle)
BRSNN = *Brassica napus* (spring rape)
EPHHL = *Euphorbia heterophylla* (poinsettia)
CYPES = *Cyperus esculentus* (nutsedge)
ABUTH = *Abutilon theophrasti* (velvetleaf)
CHEAL = *Chenopodium album* L. (common lambsquarters)
SORVU = *Sorghum vulgare* (grain sorghum)
TRZAW = *Triticum aestivum* (winter wheat)
ZEAMX = *Zea mays* (maize)

TABLE 20

Effect (% visual injury) of compound 13 and 2,4-D EHE on weeds.

| Application rate (g ae/ha) | compound 13 | 5 | 0 | 5 |
|---|---|---|---|---|
| | 2,4-D EHE | 0 | 140 | 140 |
| VIOTR | Obs | 25 | 35 | 78 |
| | Exp | — | — | 51 |
| | Δ | | | 26 |
| CHEAL | Obs | 60 | 73 | 96 |
| | Exp | — | — | 89 |
| | Δ | | | 7 |
| STEME | Obs | 50 | 63 | 85 |
| | Exp | — | — | 81 |
| | Δ | | | 4 |
| CIRAR | Obs | 10 | 50 | 85 |
| | Exp | — | — | 55 |
| | Δ | | | 30 |
| EPHHL | Obs | 75 | 35 | 100 |
| | Exp | — | — | 84 |
| | Δ | | | 16 |
| CYPES | Obs | 0 | 0 | 40 |
| | Exp | — | — | 0 |
| | Δ | | | 40 |
| ABUTH | Obs | 0 | 55 | 85 |
| | Exp | — | — | 55 |
| | Δ | | | 30 |

TABLE 20-continued

Effect (% visual injury) of compound 13 and 2,4-D EHE on weeds.

| Application rate (g ae/ha) | compound 13<br>2,4-D EHE | 5<br>0 | 0<br>140 | 5<br>140 |
|---|---|---|---|---|
| POLCO | Obs | 25 | 55 | 73 |
|  | Exp | — | — | 66 |
|  | Δ |  |  | 6 | g ae/ha = grams acid equivalent per hectare
2,4-D EHE = 2-ethylhexyl (2,4-dichlorophenoxy)acetate
VIOTR = *Viola tricolor* (wild pansy)
CHEAL = *Chenopodium album* L. (common lambsquarters)
STEME = *Stellaria media* (common chickweed)
CIRAR = *Cirsium arvense* (Canadian thistle)
EPHHL = *Euphorbia heterophylla* (poinsettia)
CYPES = *Cyperus esculentus* (nutsedge)
ABUTH = *Abutilon theophrasti* (velvetleaf)
POLCO = *Polygonum convolvulus* (wild buckwheat)

TABLE 21

Effect (% visual injury) of compound 14 and 2,4-D EHE on weeds.

| Application rate (g ae/ha) | compound 14<br>2,4-D EHE | 5<br>0 | 0<br>140 | 5<br>140 |
|---|---|---|---|---|
| VIOTR | Obs | 10 | 35 | 80 |
|  | Exp | — | — | 42 |
|  | Δ |  |  | 39 |
| CHEAL | Obs | 15 | 73 | 83 |
|  | Exp | — | — | 77 |
|  | Δ |  |  | 6 |
| CIRAR | Obs | 5 | 50 | 87 |
|  | Exp | — | — | 53 |
|  | Δ |  |  | 34 |
| BRSNN | Obs | 10 | 60 | 88 |
|  | Exp | — | — | 64 |
|  | Δ |  |  | 24 |
| HELAN | Obs | 10 | 75 | 87 |
|  | Exp | — | — | 78 |
|  | Δ |  |  | 9 |
| EPHHL | Obs | 20 | 35 | 83 |
|  | Exp | — | — | 48 |
|  | Δ |  |  | 35 |
| ABUTH | Obs | 0 | 55 | 68 |
|  | Exp | — | — | 55 |
|  | Δ |  |  | 13 |
| SORVU | Obs | 0 | 0 | 5 |
|  | Exp | — | — | 0 |
|  | Δ |  |  | 5 |
| TRZAW | Obs | 0 | 0 | 0 |
|  | Exp | — | — | 0 |
|  | Δ |  |  | 0 |
| ZEAMX | Obs | 0 | 0 | 0 |
|  | Exp | — | — | 0 |
|  | Δ |  |  | 0 | g ae/ha = grams acid equivalent per hectare
2,4-D EHE = 2-ethylhexyl (2,4-dichlorophenoxy)acetate
VIOTR = *Viola tricolor* (wild pansy)
CHEAL = *Chenopodium album* L. (common lambsquarters)
CIRAR = *Cirsium arvense* (Canadian thistle)
BRSNN = *Brassica napus* (spring rape)
HELAN = *Helianthus annus* (sunflower)
EPHHL = *Euphorbia heterophylla* (poinsettia)
ABUTH = *Abutilon theophrasti* (velvetleaf)
SORVU = *Sorghum vulgare* (grain sorghum)
TRZAW = *Triticum aestivum* (winter wheat)
ZEAMX = *Zea mays* (maize)

TABLE 22

Effect (% visual injury) of compound 15 and 2,4-D EHE on weeds.

| Application rate (g ae/ha) | compound 15<br>2,4-D EHE | 5<br>0 | 0<br>140 | 5<br>140 |
|---|---|---|---|---|
| VIOTR | Obs | 33 | 35 | 73 |
|  | Exp | — | — | 56 |
|  | Δ |  |  | 16 |
| CIRAR | Obs | 15 | 50 | 83 |
|  | Exp | — | — | 58 |
|  | Δ |  |  | 25 |
| SORVU | Obs | 0 | 0 | 10 |
|  | Exp | — | — | 0 |
|  | Δ |  |  | 10 |
| EPHHL | Obs | 73 | 35 | 90 |
|  | Exp | — | — | 82 |
|  | Δ |  |  | 8 |
| CYPES | Obs | 25 | 0 | 30 |
|  | Exp | — | — | 25 |
|  | Δ |  |  | 5 |
| ABUTH | Obs | 30 | 55 | 85 |
|  | Exp | — | — | 69 |
|  | Δ |  |  | 17 |
| POLCO | Obs | 30 | 55 | 100 |
|  | Exp | — | — | 69 |
|  | Δ |  |  | 32 |
| HELAN | Obs | 90 | 75 | 100 |
|  | Exp | — | — | 98 |
|  | Δ |  |  | 3 |
| TRZAW | Obs | 5 | 0 | 5 |
|  | Exp | — | — | 5 |
|  | Δ |  |  | 0 |
| ZEAMX | Obs | 0 | 0 | 0 |
|  | Exp | — | — | 0 |
|  | Δ |  |  | 0 | g ae/ha = grams acid equivalent per hectare
2,4-D EHE = 2-ethylhexyl (2,4-dichlorophenoxy)acetate
VIOTR = *Viola tricolor* (wild pansy)
CIRAR = *Cirsium arvense* (Canadian thistle)
SORVU = *Sorghum vulgare* (grain sorghum)
EPHHL = *Euphorbia heterophylla* (poinsettia)
CYPES = *Cyperus esculentus* (nutsedge)
ABUTH = *Abutilon theophrasti* (velvetleaf)
POLCO = *Polygonum convolvulus* (wild buckwheat)
HELAN = *Helianthus annus* (common sunflower)
TRZAW = *Triticum aestivum* (winter wheat)
ZEAMX = *Zea mays* (maize)

TABLE 23

Effect (% visual injury) of compound 16 and 2,4-D EHE on weeds.

| Application rate (g ae/ha) | compound 16<br>2,4-D EHE | 5<br>0 | 0<br>140 | 5<br>140 |
|---|---|---|---|---|
| BRSNN | Obs | 60 | 60 | 96 |
|  | Exp | — | — | 84 |
|  | Δ |  |  | 12 |
| CIRAR | Obs | 20 | 50 | 78 |
|  | Exp | — | — | 60 |
|  | Δ |  |  | 18 |
| CYPES | Obs | 25 | 0 | 70 |
|  | Exp | — | — | 25 |
|  | Δ |  |  | 45 |
| SORVU | Obs | 13 | 0 | 35 |
|  | Exp | — | — | 13 |
|  | Δ |  |  | 23 |
| VIOTR | Obs | 25 | 35 | 70 |
|  | Exp | — | — | 51 |
|  | Δ |  |  | 19 |

TABLE 23-continued

Effect (% visual injury) of compound 16 and 2,4-D EHE on weeds.

| Application rate (g ae/ha) | compound 16 2,4-D EHE | 5 0 | 0 140 | 5 140 |
|---|---|---|---|---|
| TRZAW | Obs | 0 | 0 | 0 |
|  | Exp |  |  | 0 |
|  | Δ |  |  | 0 | g ae/ha = grams acid equivalent per hectare
2,4-D EHE = 2-ethylhexyl (2,4-dichlorophenoxy)acetate
BRSNN = *Brassica napus* (spring rape)
CIRAR = *Cirsium arvense* (Canadian thistle)
CYPES = *Cyperus esculentus* (nutsedge)
SORVU = *Sorghum vulgare* (grain sorghum)
VIOTR = *Viola tricolor* (wild pansy)
TRZAW = *Triticum aestivum* (winter wheat)

Example 6—Greenhouse Trials

Following the protocol in Example 1, compound 1 (SC) was combined with 2,4 D EHE (EC), Arylex™ (halauxifen-methyl; SC), fluroxypyr-MHE (EC), and MCPA EHE, and Compound 2 (SC) was combined with 2,4 D EHE (EC) and Arylex™ (halauxifen-methyl, SC). The mixtures were applied to spring barley (HORVS) and winter wheat (TRZAW), and the phytotoxicity of the herbicidal compositions was measured. In addition, the efficacy of the herbicidal composition on pigweed (*Amaranthus retroflexus*, AMARE), black mustard (*Brassica nigra*, BRSNI), winter rape (*Brassica napus*, BRSNW), turnip (*Brassica rapa*, BRSRR), kochia (*Kochia scoparia*, KCHSC), wild buckwheat (*Polygonum convolvulus*, POLCO), wild radish (*Raphanus raphanistrum*, RAPRA), Russian thistle (*Salsola iberica*, SASKR), wild mustard (*Sinapis arvensis*, SINAR), Indian hedge mustard (*Sisymbrium orientale*, SSYOR), and wild pansy (*Viola tricolor*, VIOTR) was evaluated. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 24-30.

TABLE 24

Effect (% visual injury) of compound 1 (SC) and 2,4-D EHE on weeds.

| Application Rate | compound 1 SC (g ae/ha) 2,4-D EHE (g ae/ha) | 5 0 | 10 0 | 0 420 | 5 420 | 10 420 |
|---|---|---|---|---|---|---|
| POLCO | Obs | 30 | 30 | 60 | 80 | 80 |
|  | Exp |  |  |  | 72 | 72 |
|  | Δ |  |  |  | 8 | 8 |
| HORVS | Obs | 0 | 0 | 0 | 0 | 0 |
|  | Exp |  |  |  | 0 | 0 |
|  | Δ |  |  |  | 0 | 0 |
| TRZAW | Obs | 0 | 0 | 0 | 5 | 5 |
|  | Exp |  |  |  | 0 | 0 |
|  | Δ |  |  |  | 5 | 5 | g ae/ha = grams acid equivalent per hectare
POLCO = *Polygonum convolvulus* (wild buckwheat)
HORVS = (*Hordeum vulgare*, barley)
TRZAW = *Triticum aestivum* (winter wheat)

TABLE 25

Effect (% visual injury) of compound 1 (SC) and 2,4-D EHE on weeds.

| Application Rate | compound 1 SC (g ae/ha) 2,4-D EHE (g ae/ha) | 5 0 | 10 0 | 0 400 | 5 400 | 10 400 |
|---|---|---|---|---|---|---|
| BRSNW | Obs | 30 | 60 | 93 | 100 | 100 |
|  | Exp |  |  |  | 95 | 93 |
|  | Δ |  |  |  | 5 | 7 |
| POLCO | Obs | 10 | 40 | 80 | 100 | 100 |
|  | Exp |  |  |  | 82 | 80 |
|  | Δ |  |  |  | 18 | 20 |
| SINAR | Obs | 100 | 80 | 97 | 100 | 100 |
|  | Exp |  |  |  | 100 | 97 |
|  | Δ |  |  |  | 0 | 3 |
| TRZAW | Obs | 20 | 15 | 10 | 20 | 25 |
|  | Exp |  |  |  | 28 | 22 |
|  | Δ |  |  |  | −8 | 3 | g ae/ha = grams acid equivalent per hectare
BRSNW = *Brassica napus* (winter rape)
POLCO = *Polygonum convolvulus* (wild buckwheat)
SINAR = *Sinapis arvensis* (wild mustard)
TRZAW = *Triticum aestivum* (winter wheat)

TABLE 26

Effect (% visual injury) of compound 2 (SC) and 2,4-D EHE on weeds.

| Application Rate | compound 2 SC (g ae/ha) 2,4-D EHE (g ae/ha) | 5 0 | 10 0 | 0 400 | 5 400 | 10 400 |
|---|---|---|---|---|---|---|
| BRSNW | Obs | 50 | 50 | 93 | 100 | 100 |
|  | Exp |  |  |  | 97 | 93 |
|  | Δ |  |  |  | 4 | 7 |
| POLCO | Obs | 30 | 50 | 80 | 100 | 100 |
|  | Exp |  |  |  | 86 | 80 |
|  | Δ |  |  |  | 14 | 20 |
| SINAR | Obs | 100 | 100 | 97 | 100 | 100 |
|  | Exp |  |  |  | 100 | 97 |
|  | Δ |  |  |  | 0 | 3 |
| TRZAW | Obs | 10 | 20 | 10 | 15 | 15 |
|  | Exp |  |  |  | 19 | 27 |
|  | Δ |  |  |  | −4 | −12 | g ae/ha = grams acid equivalent per hectare
BRSNW = *Brassica napus* (winter rape)
POLCO = *Polygonum convolvulus* (wild buckwheat)
SINAR = *Sinapis arvensis* (wild mustard)
TRZAW = *Triticum aestivum* (winter wheat)

TABLE 27

Effect (% visual injury) of compound 1 (SC) and Arylex ™ (halauxifen-methyl) on weeds.

| Application Rate | compound 1 SC (g ae/ha) Arylex ™ (g ae/ha) | 2.5 0 | 5 0 | 0 2.5 | 0 5 | 2.5 2.5 | 5 5 |
|---|---|---|---|---|---|---|---|
| BRSRR | Obs | 45 | 62 | 10 | 13 | 62 | 68 |
|  | Exp |  |  |  |  | 51 | 67 |
|  | Δ |  |  |  |  | 11 | 2 |
| RAPRA | Obs | 13 | 13 | 10 | 20 | 37 | 47 |
|  | Exp |  |  |  |  | 22 | 31 |
|  | Δ |  |  |  |  | 15 | 16 |
| SSYOR | Obs | 13 | 20 | 57 | 63 | 70 | 73 |
|  | Exp |  |  |  |  | 62 | 71 |
|  | Δ |  |  |  |  | 8 | 3 |
| VIOTR | Obs | 13 | 23 | 15 | 20 | 30 | 40 |
|  | Exp |  |  |  |  | 26 | 39 |
|  | Δ |  |  |  |  | 4 | 1 | g ae/ha = grams acid equivalent per hectare
BRSRR = *Brassica rapa* (turnip)
RAPRA = *Raphanus raphanistrum* (wild radish)
SSYOR = *Sisymbrium orientale* (Indian hedge mustard)
VIOTR = *Viola tricolor* (wild pansy)

TABLE 28

Effect (% visual injury) of compound 2 (SC) and Arylex™ (halauxifen-methyl) on weeds.

| Application Rate | compound 2 SC (g ae/ha) | 2.5 | 5 | 0 | 0 | 2.5 | 5 |
|---|---|---|---|---|---|---|---|
| | Arylex™ (g ae/ha) | 0 | 0 | 2.5 | 5 | 2.5 | 5 |
| BRSNI | Obs | 30 | 70 | 0 | 0 | 43 | 65 |
| | Exp | | | | | 30 | 70 |
| | Δ | | | | | 13 | −5 |
| BRSRR | Obs | 23 | 67 | 10 | 13 | 57 | 73 |
| | Exp | | | | | 31 | 71 |
| | Δ | | | | | 26 | 1 |
| RAPRA | Obs | 17 | 25 | 10 | 20 | 53 | 50 |
| | Exp | | | | | 25 | 40 |
| | Δ | | | | | 28 | 10 |
| SINAR | Obs | 87 | 94 | 65 | 78 | 98 | 96 |
| | Exp | | | | | 95 | 99 |
| | Δ | | | | | 2 | −3 |
| SSYOR | Obs | 20 | 40 | 57 | 63 | 70 | 85 |
| | Exp | | | | | 65 | 78 |
| | Δ | | | | | 5 | 7 |
| VIOTR | Obs | 13 | 23 | 15 | 20 | 40 | 45 |
| | Exp | | | | | 26 | 39 |
| | Δ | | | | | 14 | 6 | g ae/ha = grams acid equivalent per hectare
BRSNI = *Brassica nigra* (black mustard)
BRSRR = *Brassica rapa* (turnip)
RAPRA = *Raphanus raphanistrum* (wild radish)
SINAR = *Sinapis arvensis* (wild mustard)
SSYOR = *Sisymbrium orientale* (Indian hedge mustard)
VIOTR = *Viola tricolor* (wild pansy)

TABLE 29

Effect (% visual injury) of compound 1 (SC) and fluroxypyr-MHE on weeds.

| Application Rate | compound 1 SC (g ae/ha) | 5 | 10 | 0 | 5 | 10 |
|---|---|---|---|---|---|---|
| | fluroxypyr-MHE (g ae/ha) | 0 | 0 | 70 | 70 | 70 |
| AMARE | Obs | 70 | 85 | 50 | 100 | 100 |
| | Exp | | | | 85 | 93 |
| | Δ | | | | 15 | 8 |
| KCHSC | Obs | 75 | 100 | 93 | 100 | 100 |
| | Exp | | | | 98 | 100 |
| | Δ | | | | 2 | 0 |
| POLCO | Obs | 30 | 30 | 75 | 100 | 100 |
| | Exp | | | | 83 | 83 |
| | Δ | | | | 18 | 18 |
| SASKR | Obs | 65 | 80 | 95 | 100 | 100 |
| | Exp | | | | 98 | 99 |
| | Δ | | | | 2 | 1 |
| HORVS | Obs | 0 | 0 | 0 | 0 | 0 |
| | Exp | | | | 0 | 0 |
| | Δ | | | | 0 | 0 |
| TRZAW | Obs | 0 | 0 | 0 | 0 | 0 |
| | Exp | | | | 0 | 0 |
| | Δ | | | | 0 | 0 | g ae/ha = grams acid equivalent per hectare
AMARE = *Amaranthus retroflexus* (pigweed)
KCHSC = *Kochia scoparia* (kochia)
POLCO = *Polygonum convolvulus* (wild buckwheat)
SASKR = *Salsola iberica* (Russian thistle)
HORVS = *Hordeum vulgare* (barley)
TRZAW = *Triticum aestivum* (winter wheat)

TABLE 30

Effect (% visual injury) of compound 1 (SC) and MCPA EHE on weeds.

| Application Rate | compound 1 SC (g ae/ha) | 5 | 10 | 0 | 5 | 10 |
|---|---|---|---|---|---|---|
| | MCPA EHE (g ae/ha) | 0 | 0 | 420 | 420 | 420 |
| POLCO | Obs | 30 | 30 | 65 | 80 | 100 |
| | Exp | | | | 76 | 76 |
| | Δ | | | | 5 | 25 |
| HORVS | Obs | 0 | 0 | 0 | 0 | 10 |
| | Exp | | | | 0 | 0 |
| | Δ | | | | 0 | 10 |
| TRZAW | Obs | 0 | 0 | 0 | 0 | 0 |
| | Exp | | | | 0 | 0 |
| | Δ | | | | 0 | 0 | g ae/ha = grams acid equivalent per hectare
POLCO = *Polygonum convolvulus* (wild buckwheat)
HORVS = *Hordeum vulgare* (barley)
TRZAW = *Triticum aestivum* (winter wheat)

Example 7—Greenhouse Trials

Following the protocol in Example 1, compound 1 (EC) was combined with 2,4-D EHE (EC), 2,4-D DMA (as Weedar™ 64), 2,4-D choline, 2,4-DB DMA (as Butyrac® 200), aminocyclopyrachlor (SL), aminopyralid-triisopropanolammonium (TIPA, as Milestone™, SL), Arylex™ (halauxifen-methyl, SC), clopyralid (as Lontrel™ 35A Herbicidal Concentrate), dicamba-dimethylammonium salt (as Banvel® 4S), dichlorprop-P (as the potassium salt), fluroxypyr-MHE (EC), MCPA EHE, MCPA DMA, mecoprop-P (as the potassium salt), picloram-potassium (as Tordon™ 22K), Rinskor™ (as the benzyl ester, SC), quinclorac (as Facet® 75 DF), and triclopyr-butotyl (as Garlon® 4 Ultra), and Compound 2 (EC) was combined with 2,4 D EHE (EC), aminopyralid-triisopropanolammonium (TIPA, as Milestone™, SL), clopyralid (as Lontrel™ 35A Herbicidal Concentrate), dicamba-dimethylammonium salt (as Banvel® 4S), fluroxypyr-MHE (EC) and MCPA EHE. The mixtures were applied to spring barley (HORVS), maize (ZEAMX), common rice (ORYSA) and winter wheat (TRZAW), and the phytotoxicity of the herbicidal compositions was measured. In addition, the efficacy of the herbicidal composition on velvetleaf (*Abutilon theophrasti*, ABUTH), blackgrass (*Alopecurus myosuroides*, ALOMY), pigweed (*Amaranthus retroflexus*, AMARE), wild oat (*Avena fatua*, AVEFA), Chinese kale (*Brassica alboglabra*, BRSAG), brown mustard (*Brassica juncea*, BRSJU), rutabaga (*Brassica napus* var. *napobrassica*, BRSNA), spring rape (*Brassica napus*, BRSNN), winter rape (*Brassica napus*, BRSNW), common lambsquarters (*Chenopodium album* L., CHEAL), Canadian thistle (*Cirsium arvense*, CIRAR), nutsedge (*Cyperus esculentus*, CYPES), large crabgrass (*Digitaria sanguinalis*, DIGSA), barnvardgrass (*Echinochloa crus-galli*, ECHCG), poinsettia (*Euphorbia heterophylla*, EPHHL), soybean (*Glycine max*, GLXMA), common sunflower (*Helianthus annuus*, HELAN), ivyleaf morningglory (*Ipomoea hederacea*, IPOHE), kochia (*Kochia scoparia*, KCHSC), wild buckwheat (*Polygonum convolvulus*, POLCO), Russian thistle (*Salsola iberica*, SASKR), wild mustard (*Sinapis arvensis*, SINAR), grain sorghum (*Sorghum vulgare*, SORVU), common chickweed (*Stellaria media*, STEME), ivyleaved speedwell (*Veronica hederifolia*, VERHE), wild pansy (*Viola tricolor*, VIOTR) was evaluated. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 31-59.

TABLE 31

Effect (% visual injury) of compound 1 (EC) and 2,4-D EHE on weeds.

| Application Rate | compound 1 (g ae/ha) 2,4-D EHE (g ae/ha) | | 5 0 | 10 0 | 0 420 | 5 420 | 10 420 |
|---|---|---|---|---|---|---|---|
| POLCO | Obs | | 30 | 30 | 60 | 70 | 100 |
|  | Exp | |  |  |  | 72 | 72 |
|  | Δ | |  |  |  | −2 | 28 |
| HORVS | Obs | | 0 | 0 | 0 | 0 | 0 |
|  | Exp | |  |  |  | 0 | 0 |
|  | Δ | |  |  |  | 0 | 0 |
| TRZAW | Obs | | 0 | 0 | 0 | 0 | 5 |
|  | Exp | |  |  |  | 0 | 0 |
|  | Δ | |  |  |  | 0 | 5 | g ae/ha = grams acid equivalent per hectare
HORVS = *Hordeum vulgare* (barley)
POLCO = *Polygonum convolvulus* (wild buckwheat)
TRZAW = *Triticum aestivum* (winter wheat)

TABLE 32

Effect (% visual injury) of compound 1 (EC) and 2,4-D EHE on weeds.

| Application Rate | compound 1 (g ae/ha) 2,4-D EHE (g ae/ha) | 5 0 | 10 0 | 0 400 | 5 400 | 10 400 |
|---|---|---|---|---|---|---|
| BRSNW | Obs | 40 | 100 | 93 | 100 | 100 |
|  | Exp |  |  |  | 96 | 93 |
|  | Δ |  |  |  | 4 | 7 |
| POLCO | Obs | 100 | 80 | 80 | 100 | 100 |
|  | Exp |  |  |  | 100 | 80 |
|  | Δ |  |  |  | 0 | 20 |
| SASKR | Obs | 10 | 65 | 70 | 90 | 93 |
|  | Exp |  |  |  | 73 | 77 |
|  | Δ |  |  |  | 17 | 17 |
| SINAR | Obs | 100 | 100 | 97 | 100 | 100 |
|  | Exp |  |  |  | 100 | 97 |
|  | Δ |  |  |  | 0 | 3 |
| HORVS | Obs | 0 | 0 | 10 | 0 | 0 |
|  | Exp |  |  |  | 10 | 10 |
|  | Δ |  |  |  | −10 | −10 |
| TRZAW | Obs | 0 | 0 | 10 | 0 | 10 |
|  | Exp |  |  |  | 10 | 10 |
|  | Δ |  |  |  | −10 | 0 | g ae/ha = grams acid equivalent per hectare
BRSNW = *Brassica napus* (winter rape)
HORVS = *Hordeum vulgare* (barley)
POLCO = *Polygonum convolvulus* (wild buckwheat)
SASKR = *Salsola iberica* (Russian thistle)
SINAR = *Sinapis arvensis* (wild mustard)
TRZAW = *Triticum aestivum* (winter wheat)

TABLE 33

Effect (% visual injury) of compound 1 (EC) and 2,4-D EHE on weeds.

| Application Rate | compound 1 (g ae/ha) 2,4-D EHE (g ae/ha) | 5 0 | 0 400 | 5 400 |
|---|---|---|---|---|
| BRSNN | Obs | 50 | 75 | 100 |
|  | Exp |  |  | 88 |
|  | Δ |  |  | 13 |
| CIRAR | Obs | 10 | 70 | 75 |
|  | Exp |  |  | 73 |
|  | Δ |  |  | 2 |

TABLE 33-continued

Effect (% visual injury) of compound 1 (EC) and 2,4-D EHE on weeds.

| Application Rate | compound 1 (g ae/ha) 2,4-D EHE (g ae/ha) | 5 0 | 0 400 | 5 400 |
|---|---|---|---|---|
| EPHHL | Obs | 95 | 60 | 100 |
|  | Exp |  |  | 98 |
|  | Δ |  |  | 2 |
| KCHSC | Obs | 65 | 10 | 75 |
|  | Exp |  |  | 69 |
|  | Δ |  |  | 7 |
| STEME | Obs | 60 | 10 | 65 |
|  | Exp |  |  | 64 |
|  | Δ |  |  | 1 |
| VIOTR | Obs | 10 | 65 | 70 |
|  | Exp |  |  | 69 |
|  | Δ |  |  | 2 |
| ORYSA | Obs | 0 | 0 | 0 |
|  | Exp |  |  | 0 |
|  | Δ |  |  | 0 |
| TRZAW | Obs | 10 | 0 | 5 |
|  | Exp |  |  | 10 |
|  | Δ |  |  | −5 |
| ZEAMX | Obs | 5 | 0 | 0 |
|  | Exp |  |  | 5 |
|  | Δ |  |  | −5 | g ae/ha = grams acid equivalent per hectare
BRSNN = *Brassica napus* (spring rape)
CIRAR = *Cirsium arvense* (Canadian thistle)
EPHHL = *Euphorbia heterophylla* (poinsettia)
KCHSC = *Kochia scoparia* (kochia)
VIOTR = *Viola tricolor* (wild pansy)
ORYSA = *Oryza sativa* (common rice)
STEME = *Stellaria media* (common chickweed)
TRZAW = *Triticum aestivum* (winter wheat)
ZEAMX = *Zea mays* (maize)

TABLE 34

Effect (% visual injury) of compound 1 (EC) and 2,4-D choline on weeds.

| Application Rate | compound 1 (g ae/ha) 2,4-D choline (g ae/ha) | 5 0 | 0 400 | 5 400 |
|---|---|---|---|---|
| BRSAG | Obs | 15 | 85 | 93 |
|  | Exp |  |  | 87 |
|  | Δ |  |  | 6 |
| BRSJU | Obs | 60 | 90 | 97 |
|  | Exp |  |  | 96 |
|  | Δ |  |  | 1 |
| BRSNA | Obs | 65 | 93 | 99 |
|  | Exp |  |  | 98 |
|  | Δ |  |  | 1 | g ae/ha = grams acid equivalent per hectare
BRSAG = *Brassica alboglabra* (Chinese kale)
BRSJU = *Brassica juncea* (brown mustard)
BRSNA = *Brassica napus* var. *napobrassica* (rutabaga)

TABLE 35

Effect (% visual injury) of compound 1 (EC) and 2,4-DMA on weeds.

| Application Rate | compound 1 (g ae/ha) 2,4-DMA (g ae/ha) | 5 0 | 0 400 | 5 400 |
|---|---|---|---|---|
| ABUTH | Obs | 70 | 75 | 97 |
|  | Exp |  |  | 93 |
|  | Δ |  |  | 5 |
| BRSNN | Obs | 50 | 85 | 100 |
|  | Exp |  |  | 93 |
|  | Δ |  |  | 8 |

TABLE 35-continued

Effect (% visual injury) of compound 1 (EC) and 2,4-D DMA on weeds.

| Application Rate | compound 1 (g ae/ha)<br>2,4-DMA (g ae/ha) | 5<br>0 | 0<br>400 | 5<br>400 |
|---|---|---|---|---|
| CIRAR | Obs | 10 | 70 | 85 |
|  | Exp |  |  | 73 |
|  | Δ |  |  | 12 |
| CYPES | Obs | 30 | 30 | 60 |
|  | Exp |  |  | 51 |
|  | Δ |  |  | 9 |
| HELAN | Obs | 80 | 80 | 100 |
|  | Exp |  |  | 96 |
|  | Δ |  |  | 4 |
| IPOHE | Obs | 20 | 80 | 100 |
|  | Exp |  |  | 84 |
|  | Δ |  |  | 16 |
| KCHSC | Obs | 65 | 10 | 75 |
|  | Exp |  |  | 69 |
|  | Δ |  |  | 7 |
| VIOTR | Obs | 10 | 65 | 80 |
|  | Exp |  |  | 69 |
|  | Δ |  |  | 12 |
| ORYSA | Obs | 0 | 0 | 0 |
|  | Exp |  |  | 0 |
|  | Δ |  |  | 0 |
| TRZAW | Obs | 10 | 0 | 0 |
|  | Exp |  |  | 10 |
|  | Δ |  |  | −10 |
| ZEAMX | Obs | 5 | 0 | 0 |
|  | Exp |  |  | 5 |
|  | Δ |  |  | −5 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
CYPES = *Cyperus esculentus* (nutsedge)
HELAN = *Helianthus annus* (sunflower)
IPOHE = *Ipomoea hederacea* (ivyleaf morningglory)
KCHSC = *Kochia scopario* (kochia)
ORYSA = *Oryza sativa* (common rice)
TRZAW = *Triticum aestivum* (winter wheat)
VIOTR = *Viola tricolor* (wild pansy)
ZEAMX = *Zea mays* (maize)

TABLE 36

Effect (% visual injury) of compound 1 (EC) and 2,4-DB DMA on weeds.

| Application Rate | compound 1 (g ae/ha)<br>2,4-DB DMA (g ae/ha) | 5<br>0 | 0<br>400 | 5<br>400 |
|---|---|---|---|---|
| BRSNN | Obs | 50 | 70 | 100 |
|  | Exp |  |  | 85 |
|  | Δ |  |  | 15 |
| CIRAR | Obs | 10 | 40 | 70 |
|  | Exp |  |  | 46 |
|  | Δ |  |  | 24 |
| CYPES | Obs | 30 | 0 | 50 |
|  | Exp |  |  | 30 |
|  | Δ |  |  | 20 |
| EPHHL | Obs | 95 | 10 | 100 |
|  | Exp |  |  | 96 |
|  | Δ |  |  | 5 |
| IPOHE | Obs | 20 | 70 | 85 |
|  | Exp |  |  | 76 |
|  | Δ |  |  | 9 |
| KCHSC | Obs | 65 | 10 | 80 |
|  | Exp |  |  | 69 |
|  | Δ |  |  | 12 |
| POLCO | Obs | 95 | 60 | 100 |
|  | Exp |  |  | 98 |
|  | Δ |  |  | 2 |

TABLE 36-continued

Effect (% visual injury) of compound 1 (EC) and 2,4-DB DMA on weeds.

| Application Rate | compound 1 (g ae/ha)<br>2,4-DB DMA (g ae/ha) | 5<br>0 | 0<br>400 | 5<br>400 |
|---|---|---|---|---|
| ORYSA | Obs | 0 | 0 | 0 |
|  | Exp |  |  | 0 |
|  | Δ |  |  | 0 |
| TRZAW | Obs | 10 | 10 | 15 |
|  | Exp |  |  | 19 |
|  | Δ |  |  | −4 |
| ZEAMX | Obs | 5 | 0 | 0 |
|  | Exp |  |  | 5 |
|  | Δ |  |  | −5 | g ae/ha = grams acid equivalent per hectare
BRSNN = *Brassica napus* (spring rape)
CIRAR = *Cirsium arvense* (Canadian thistle)
CYPES = *Cyperus esculentus* (nutsedge)
EPHHL = *Euphorbia heterophylla* (poinsettia)
IPOHE = *Ipomoea hederacea* (ivyleaf morningglory)
KCHSC = *Kochia scoparia* (kochia)
ORYSA = *Oryza sativa* (common rice)
POLCO = *Polygonum convolvulus* (wild buckwheat)
TRZAW = *Triticum aestivum* (winter wheat)
ZEAMX = *Zea mays* (maize)

TABLE 37

Effect (% injury) of compound 1 (EC) and aminocyclopyrachlor on weeds.

| Application Rate | compound 1 (g ae/ha)<br>aminocyclopyrachlor (g ae/ha) | 5<br>0 | 0<br>100 | 5<br>100 |
|---|---|---|---|---|
| VERHE | Obs | 40 | 75 | 99 |
|  | Exp |  |  | 85 |
|  | Δ |  |  | 14 | g ae/ha = grams acid equivalent per hectare
VERHE = *Veronica hederifolia* (ivyleaved speedwell)

TABLE 38

Effect (% visual injury) of compound 1 (EC) and aminopyralid-TIPA on weeds.

| Application Rate | compound 1 (g ae/ha)<br>aminopyralid-TIPA (g ae/ha) | 5<br>0 | 0<br>5 | 5<br>5 |
|---|---|---|---|---|
| BRSNN | Obs | 50 | 10 | 80 |
|  | Exp |  |  | 55 |
|  | Δ |  |  | 25 |
| CIRAR | Obs | 10 | 60 | 75 |
|  | Exp |  |  | 64 |
|  | Δ |  |  | 11 |
| HELAN | Obs | 80 | 60 | 97 |
|  | Exp |  |  | 92 |
|  | Δ |  |  | 5 |
| IPOHE | Obs | 20 | 60 | 70 |
|  | Exp |  |  | 68 |
|  | Δ |  |  | 2 |
| KCHSC | Obs | 65 | 10 | 75 |
|  | Exp |  |  | 69 |
|  | Δ |  |  | 7 |
| POLCO | Obs | 95 | 65 | 100 |
|  | Exp |  |  | 98 |
|  | Δ |  |  | 2 |
| SORVU | Obs | 30 | 0 | 70 |
|  | Exp |  |  | 30 |
|  | Δ |  |  | 40 |
| STEME | Obs | 60 | 60 | 93 |
|  | Exp |  |  | 84 |
|  | Δ |  |  | 9 |

TABLE 38-continued

Effect (% visual injury) of compound 1 (EC) and aminopyralid-TIPA on weeds.

| Application Rate | compound 1 (g ae/ha) aminopyralid-TIPA (g ae/ha) | 5 0 | 0 5 | 5 5 |
|---|---|---|---|---|
| VIOTR | Obs | 10 | 10 | 30 |
|  | Exp |  |  | 19 |
|  | Δ |  |  | 11 |
| ORYSA | Obs | 0 | 0 | 0 |
|  | Exp |  |  | 0 |
|  | Δ |  |  | 0 |
| TRZAW | Obs | 10 | 0 | 10 |
|  | Exp |  |  | 10 |
|  | Δ |  |  | 0 |
| ZEAMX | Obs | 5 | 0 | 0 |
|  | Exp |  |  | 5 |
|  | Δ |  |  | −5 | g ae/ha = grams acid equivalent per hectare
BRSNN = *Brassica napes* (spring rape)
CIRAR = *Cirsium arvense* (Canadian thistle)
HELAN = *Helianthus annuus* (sunflower)
IPOHE = *Ipomoea hederacea* (ivyleaf morningglory)
KCHSC = *Kochia scoparia* (kochia)
ORYSA = *Oryza sativa* (common rice)
POLCO = *Polygonum convolvulus* (wild buckwheat)
SORVU = *Sorghum vulgare* (grain sorghum)
STEME = *Stellaria media* (common chickweed)
TRZAW = *Triticum aestivum* (winter wheat)
VIOTR = *Viola tricolor* (wild pansy)
ZEAMX = *Zea mays* (maize)

TABLE 39

Effect (% visual injury) of compound 1 (EC) and Arylex ™ on weeds.

| Application Rate | compound 1 (g ae/ha) Arylex ™ (g ae/ha) | 5 0 | 0 2.5 | 5 2.5 |
|---|---|---|---|---|
| BRSNN | Obs | 50 | 20 | 85 |
|  | Exp |  |  | 60 |
|  | Δ |  |  | 25 |
| CIRAR | Obs | 10 | 50 | 75 |
|  | Exp |  |  | 55 |
|  | Δ |  |  | 20 |
| IPOHE | Obs | 20 | 10 | 50 |
|  | Exp |  |  | 28 |
|  | Δ |  |  | 22 |
| SORVU | Obs | 30 | 0 | 70 |
|  | Exp |  |  | 30 |
|  | Δ |  |  | 40 |
| ORYSA | Obs | 0 | 0 | 0 |
|  | Exp |  |  | 0 |
|  | Δ |  |  | 0 |
| TRZAW | Obs | 10 | 0 | 0 |
|  | Exp |  |  | 10 |
|  | Δ |  |  | −10 |
| ZEAMX | Obs | 5 | 0 | 10 |
|  | Exp |  |  | 5 |
|  | Δ |  |  | 5 | g ae/ha = grams acid equivalent per hectare
BRSNN = *Brassica napus* (spring rape)
CIRAR = *Cirsium arvense* (Canadian thistle)
IPOHE = *Ipomoea hederacea* (ivyleaf morningglory)
ORYSA = *Oryza sativa* (common rice)
SORVU = *Sorghum vulgare* (grain sorghum)
TRZAW = *Triticum aestivum* (winter wheat)
ZEAMX = *Zea mays* (maize)

TABLE 40

Effect (% visual injury) of compound 1 (EC) and clopyralid on weeds.

| Application Rate | compound 1 (g ae/ha) clopyralid (g ae/ha) | 5 0 | 5 120 | 0 120 |
|---|---|---|---|---|
| CHEAL | Obs | 80 | 10 | 85 |
|  | Exp |  |  | 87 |
|  | Δ |  |  | 3 |
| IPOHE | Obs | 20 | 30 | 65 |
|  | Exp |  |  | 44 |
|  | Δ |  |  | 21 |
| KCHSC | Obs | 65 | 10 | 75 |
|  | Exp |  |  | 69 |
|  | Δ |  |  | 7 |
| STEME | Obs | 60 | 0 | 70 |
|  | Exp |  |  | 60 |
|  | Δ |  |  | 10 |
| ORYSA | Obs | 0 | 0 | 0 |
|  | Exp |  |  | 0 |
|  | Δ |  |  | 0 |
| TRZAW | Obs | 10 | 0 | 0 |
|  | Exp |  |  | 10 |
|  | Δ |  |  | −10 |
| ZEAMX | Obs | 5 | 0 | 0 |
|  | Exp |  |  | 5 |
|  | Δ |  |  | −5 | g ae/ha = grams acid equivalent per hectare
CHEAL = *Chenopodium album* L. (common lambsquarters)
IPOHE = *Ipomoea hederacea* (ivyleaf morningglory)
KCHSC = *Kochia scoparia* (kochia)
ORYSA = *Oryza sativa* (common rice)
STEME = *Stellaria media* (common chickweed)
TRZAW = *Triticum aestivum* (winter wheat)
ZEAMX = *Zea mays* (maize)

TABLE 41

Effect (% visual injury) of compound 1 (EC) and dicamba-DMA on weeds.

| Application Rate | compound 1 (g ae/ha) dicamba-DMA (g ae/ha) | 5 0 | 0 150 | 5 150 |
|---|---|---|---|---|
| BRSNN | Obs | 50 | 40 | 85 |
|  | Exp |  |  | 70 |
|  | Δ |  |  | 15 |
| CIRAR | Obs | 10 | 70 | 75 |
|  | Exp |  |  | 73 |
|  | Δ |  |  | 2 |
| EPHHL | Obs | 95 | 50 | 100 |
|  | Exp |  |  | 98 |
|  | Δ |  |  | 3 |
| IPOHE | Obs | 20 | 70 | 80 |
|  | Exp |  |  | 76 |
|  | Δ |  |  | 4 |
| VIOTR | Obs | 10 | 20 | 40 |
|  | Exp |  |  | 28 |
|  | Δ |  |  | 12 |
| ORYSA | Obs | 0 | 0 | 0 |
|  | Exp |  |  | 0 |
|  | Δ |  |  | 0 |
| TRZAW | Obs | 10 | 0 | 0 |
|  | Exp |  |  | 10 |
|  | Δ |  |  | −10 |
| ZEAMX | Obs | 5 | 0 | 5 |
|  | Exp |  |  | 5 |
|  | Δ |  |  | 0 | g ae/ha = grams acid equivalent per hectare
BRSNN = *Brassica napus* (spring rape)
CIRAR = *Cirsium arvense* (Canadian thistle)
EPHHL = *Euphorbia heteraphylla* (poinsettia)
IPOHE = *Ipomoea hederacea* (ivyleaf morningglory)
ORYSA = *Oryza sativa* (common rice)
TRZAW = *Triticum aestivum* (winter wheat)
VIOTR = *Viola tricolor* (wild pansy)
ZEAMX = *Zea mays* (maize)

TABLE 42

Effect (% visual injury) of compound 1 (EC) and dichlorprop-P on weeds.

| Application Rate | compound 1 (g ae/ha)<br>dichlorprop-P (g ae/ha) | 5<br>0 | 0<br>400 | 5<br>400 |
|---|---|---|---|---|
| ABUTH | Obs<br>Exp<br>Δ | 70 | 60 | 100<br>88<br>12 |
| BRSNN | Obs<br>Exp<br>Δ | 50 | 80 | 95<br>90<br>5 |
| CIRAR | Obs<br>Exp<br>Δ | 10 | 70 | 80<br>73<br>7 |
| CYPES | Obs<br>Exp<br>Δ | 30 | 0 | 65<br>30<br>35 |
| EPHHL | Obs<br>Exp<br>Δ | 95 | 60 | 100<br>98<br>2 |
| HELAN | Obs<br>Exp<br>Δ | 80 | 85 | 100<br>97<br>3 |
| STEME | Obs<br>Exp<br>Δ | 60 | 20 | 90<br>68<br>22 |
| ORYSA | Obs<br>Exp<br>Δ | 0 | 0 | 0<br>0<br>0 |
| TRZAW | Obs<br>Exp<br>Δ | 10 | 0 | 0<br>10<br>−10 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
CYPES = *Cyperus esculentus* (nutsedge)
EPHHL = *Euphorbia heterophylla* (poinsettia)
HELAN = *Helianthus annuus* (sunflower)
ORYSA = *Oryza sativa* (common rice)
STEME = *Stellaria media* (common chickweed)
TRZAW = *Triticum aestivum* (winter wheat)

TABLE 43

Effect (% visual injury) of compound 1 (EC) and fluroxypyr-MHE on weeds.

| Application Rate | compound 1 (g ae/ha)<br>fluroxypyr-MHE (g ae/ha) | 5<br>0 | 0<br>100 | 5<br>100 |
|---|---|---|---|---|
| ABUTH | Obs<br>Exp<br>Δ | 70 | 70 | 100<br>91<br>9 |
| BRSNN | Obs<br>Exp<br>Δ | 50 | 85 | 97<br>93<br>5 |
| CIRAR | Obs<br>Exp<br>Δ | 10 | 60 | 70<br>64<br>6 |
| ECHCG | Obs<br>Exp<br>Δ | 65 | 0 | 70<br>65<br>5 |
| HELAN | Obs<br>Exp<br>Δ | 80 | 80 | 100<br>96<br>4 |
| KCHSC | Obs<br>Exp<br>Δ | 65 | 65 | 90<br>88<br>2 |
| VIOTR | Obs<br>Exp<br>Δ | 10 | 80 | 93<br>82<br>11 |
| ORYSA | Obs<br>Exp<br>Δ | 0 | 0 | 0<br>0<br>0 |
| TRZAW | Obs<br>Exp<br>Δ | 10 | 0 | 0<br>10<br>−10 |
| ZEAMX | Obs<br>Exp<br>Δ | 5 | 0 | 10<br>5<br>5 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
ECHCG = *Echinochloa crus-galli* (barnyardgrass)
HELAN = *Helianthus annuus* (sunflower)
KCHSC = *Kochia scoparia* (kocina)
ORYSA = *Oryza sativa* (common rice)
TRZAW = *Triticum aestivum* (winter wheat)
VIOTR = *Viola tricolor* (wild pansy)
ZEAMX = *Zea mays* (maize)

TABLE 44

Effect (% visual injury) of compound 1 (EC) and fluroxypyr-MHE on weeds.

| Application Rate | compound 1 (g ae/ha)<br>fluroxypyr-MHE (g ae/ha) | 5<br>0 | 10<br>0 | 0<br>70 | 5<br>70 | 10<br>70 |
|---|---|---|---|---|---|---|
| AMARE | Obs<br>Exp<br>Δ | 70 | 85 | 50 | 100<br>85<br>15 | 97<br>93<br>5 |
| BRSNW | Obs<br>Exp<br>Δ | 70 | 80 | 95 | 100<br>99<br>2 | 100<br>99<br>1 |
| POLCO | Obs<br>Exp<br>Δ | 30 | 30 | 75 | 100<br>83<br>18 | 100<br>83<br>18 |
| SASKR | Obs<br>Exp<br>Δ | 40 | 60 | 95 | 100<br>97<br>3 | 95<br>98<br>−3 |
| SINAR | Obs<br>Exp<br>Δ | 95 | 100 | 85 | 100<br>99<br>1 | 100<br>100<br>0 |
| HORVS | Obs<br>Exp<br>Δ | 0 | 0 | 0 | 5<br>0<br>5 | 0<br>0<br>0 |
| TRZAW | Obs<br>Exp<br>Δ | 0 | 0 | 0 | 10<br>0<br>10 | 0<br>0<br>0 | g ae/ha = grams acid equivalent per hectare
AMARE = *Amaranthus retroflexus* (pigweed)
BRSNW = *Brassica napus* (winter rape)
HORVS = *Hordeum vulgare* (barley)
POLCO = *Polygonum convolvulus* (wild buckwheat)
SASKR = *Salsola iberica*, (Russian thistle)
SINAR = *Sinapis arvensis*, (wild mustard)
TRZAW = *Triticum aestivum* (winter wheat)

TABLE 45

Effect (% visual injury) of compound 1 (EC) and MCPA EHE on weeds.

| Application Rate | compound 1 (g ae/ha)<br>MCPA EHE (g ae/ha) | 5<br>0 | 0<br>280 | 5<br>280 |
|---|---|---|---|---|
| ABUTH | Obs<br>Exp<br>Δ | 70 | 65 | 95<br>90<br>6 |

TABLE 45-continued

Effect (% visual injury) of compound 1 (EC) and MCPA EHE on weeds.

| Application Rate | compound 1 (g ae/ha) | 5 | 0 | 5 |
|---|---|---|---|---|
| | MCPA EHE (g ae/ha) | 0 | 280 | 280 |
| BRSNN | Obs | 50 | 95 | 100 |
| | Exp | | | 98 |
| | Δ | | | 3 |
| CIRAR | Obs | 10 | 75 | 83 |
| | Exp | | | 78 |
| | Δ | | | 6 |
| CYPES | Obs | 30 | 50 | 87 |
| | Exp | | | 65 |
| | Δ | | | 22 |
| KCHSC | Obs | | 65 | 0 | 85 |
| | Exp | | | 65 |
| | Δ | | | 20 |
| POLCO | Obs | 95 | 70 | 100 |
| | Exp | | | 99 |
| | Δ | | | 2 |
| STEME | Obs | 60 | 10 | 70 |
| | Exp | | | 64 |
| | Δ | | | 6 |
| VIOTR | Obs | 10 | 75 | 93 |
| | Exp | | | 78 |
| | Δ | | | 16 |
| ORYSA | Obs | 0 | 0 | 0 |
| | Exp | | | 0 |
| | Δ | | | 0 |
| TRZAW | Obs | 10 | 0 | 0 |
| | Exp | | | 10 |
| | Δ | | | −10 |
| ZEAMX | Obs | 5 | 0 | 0 |
| | Exp | | | 5 |
| | Δ | | | −5 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
CYPES = *Cyperus esculentus* (nutsedge)
KCHSC = *Kochia scoparia* (kochia)
ORYSA = *Oryza sativa* (common rice)
POLCO = *Polygonum convolvulus* (wild buckwheat)
STEME = *Stellaria media* (common chickweed)
TRZAW = *Triticum aestivum* (winter wheat)
VIOTR = *Viola tricolor* (wild pansy)
ZEAMX = *Zea mays* (maize)

TABLE 46

Effect (% visual injury) of compound 1 (EC) and MCPA EHE on weeds.

| Application Rate | compound 1 (g ae/ha) | 5 | 10 | 0 | 5 | 10 |
|---|---|---|---|---|---|---|
| | MCPA EHE (g ae/ha) | 0 | 0 | 420 | 420 | 420 |
| POLCO | Obs | 30 | 30 | 65 | 70 | 95 |
| | Exp | | | | 76 | 76 |
| | Δ | | | | −6 | 20 |
| HORVS | Obs | 0 | 0 | 0 | 0 | 0 |
| | Exp | | | | 0 | 0 |
| | Δ | | | | 0 | 0 |
| TRZAW | Obs | 0 | 0 | 0 | 0 | 0 |
| | Exp | | | | 0 | 0 |
| | Δ | | | | 0 | 0 | g ae/ha = grams acid equivalent per hectare
HORVS = *Hordeum vulgare* (barley)
POLCO = *Polygonum convolvulus* (wild buckwheat)
TRZAW = *Triticum aestivum* (winter wheat)

TABLE 47

Effect (% visual injury) of compound 1 (EC) and MCPA DMA on weeds.

| Application Rate | compound 1 (g ae/ha) | 5 | 0 | 5 |
|---|---|---|---|---|
| | MCPA DMA (g ae/ha) | 0 | 400 | 400 |
| BRSNN | Obs | 50 | 95 | 100 |
| | Exp | | | 98 |
| | Δ | | | 3 |
| CIRAR | Obs | 10 | 65 | 70 |
| | Exp | | | 69 |
| | Δ | | | 2 |
| STEME | Obs | 60 | 20 | 95 |
| | Exp | | | 68 |
| | Δ | | | 27 |
| VIOTR | Obs | 10 | 30 | 50 |
| | Exp | | | 37 |
| | Δ | | | 13 |
| ORYSA | Obs | 0 | 0 | 0 |
| | Exp | | | 0 |
| | Δ | | | 0 |
| TRZAW | Obs | 10 | 0 | 0 |
| | Exp | | | 10 |
| | Δ | | | −10 | g ae/ha = grams acid equivalent per hectare
BRSNN = *Brassica napus* (spring rape)
CIRAR = *Cirsium arvense* (Canadian thistle)
STEME = *Stellaria media* (common chickweed)
TRZAW = *Triticum aestivum* (winter wheat)
VIOTR = *Viola tricolor* (wild pansy)
ZEAMX = *Zea mays* (maize)

TABLE 48

Effect (% visual injury) of compound 1 (EC) and mecoprop-P on weeds.

| Application Rate | compound 1 (g ae/ha) | 5 | 0 | 5 |
|---|---|---|---|---|
| | mecoprop-P (g ae/ha) | 0 | 400 | 400 |
| ABUTH | Obs | 70 | 30 | 100 |
| | Exp | | | 79 |
| | Δ | | | 21 |
| BRSNN | Obs | 50 | 30 | 80 |
| | Exp | | | 65 |
| | Δ | | | 15 |
| CIRAR | Obs | 10 | 10 | 80 |
| | Exp | | | 19 |
| | Δ | | | 61 |
| EPHHL | Obs | 95 | 30 | 100 |
| | Exp | | | 97 |
| | Δ | | | 4 |
| IPOHE | Obs | 20 | 30 | 70 |
| | Exp | | | 44 |
| | Δ | | | 26 |
| KCHSC | Obs | 65 | 10 | 10 |
| | Exp | | | 69 |
| | Δ | | | 12 |
| SORVU | Obs | 30 | 0 | 60 |
| | Exp | | | 30 |
| | Δ | | | 30 |
| STEME | Obs | 60 | 0 | 80 |
| | Exp | | | 60 |
| | Δ | | | 20 |
| ORYSA | Obs | 0 | 0 | 0 |
| | Exp | | | 0 |
| | Δ | | | 0 |
| TRZAW | Obs | 10 | 0 | 10 |
| | Exp | | | 10 |
| | Δ | | | 0 |

TABLE 48-continued

Effect (% visual injury) of compound 1 (EC) and mecoprop-P on weeds.

| Application Rate | compound 1 (g ae/ha) | 5 | 0 | 5 |
|---|---|---|---|---|
|  | mecoprop-P (g ae/ha) | 0 | 400 | 400 |
| ZEAMX | Obs | 5 | 0 | 0 |
|  | Exp |  |  | 5 |
|  | Δ |  |  | −5 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
EPHHL = *Euphorbia heterophylla* (poinsettia)
IPOHE = *Ipomoea hederacea* (ivyleaf morningglory)
KCHSC = *Kocher scoparia* (kochia)
ORYSA = *Oryza sativa* (common rice)
SORVU = *Sorghum vulgare* (grain sorghum)
STEME = *Stellaria media* (common chickweed)
TRZAW = *Triticum aestivum* (winter wheat)
ZEAMX = *Zea mays* (maize)

TABLE 49

Effect (% visual injury) of compound 1 (EC) and picloram-potassium on weeds.

| Application Rate | compound 1 (g ae/ha) | 5 | 0 | 5 |
|---|---|---|---|---|
|  | picloram-potassium (g ae/ha) | 0 | 10 | 10 |
| ABUTH | Obs | 70 | 35 | 100 |
|  | Exp |  |  | 81 |
|  | Δ |  |  | 20 |
| BRSNN | Obs | 50 | 20 | 80 |
|  | Exp |  |  | 60 |
|  | Δ |  |  | 20 |
| CIRAR | Obs | 10 | 60 | 80 |
|  | Exp |  |  | 64 |
|  | Δ |  |  | 16 |
| CYPES | Obs | 30 | 0 | 60 |
|  | Exp |  |  | 30 |
|  | Δ |  |  | 30 |
| EPHHL | Obs | 95 | 20 | 100 |
|  | Exp |  |  | 96 |
|  | Δ |  |  | 4 |
| IPOHE | Obs | 20 | 40 | 60 |
|  | Exp |  |  | 52 |
|  | Δ |  |  | 8 |
| KCHSC | Obs | 65 | 0 | 85 |
|  | Exp |  |  | 65 |
|  | Δ |  |  | 20 |
| SORVU | Obs | 30 | 0 | 60 |
|  | Exp |  |  | 30 |
|  | Δ |  |  | 30 |
| VIOTR | Obs | 10 | 0 | 20 |
|  | Exp |  |  | 10 |
|  | Δ |  |  | 10 |
| ORYSA | Obs | 0 | 0 | 0 |
|  | Exp |  |  | 0 |
|  | Δ |  |  | 0 |
| TRZAW | Obs | 10 | 10 | 0 |
|  | Exp |  |  | 10 |
|  | Δ |  |  | −10 |

TABLE 49-continued

Effect (% visual injury) of compound 1 (EC) and picloram-potassium on weeds.

| Application Rate | compound 1 (g ae/ha) | 5 | 0 | 5 |
|---|---|---|---|---|
|  | picloram-potassium (g ae/ha) | 0 | 10 | 10 |
| ZEAMX | Obs | 5 | 0 | 0 |
|  | Exp |  |  | 5 |
|  | Δ |  |  | −5 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
CYPES = *Cyperus esculentus* (nutsedge)
EPHHL = *Euphorbia heterophylla* (poinsettia)
IPOHE = *Ipomoea hederacea* (ivyleaf morningglory)
KCHSC = *Kochia scoparia* (kochia)
ORYSA = *Oryza sativa* (common rice)
SORVU = *Sorghum vulgare* (pain sorghum)
TRZAW = *Triticum aestivum* (winter wheat)
VIOTR = *Viola tricolor* (wild pansy)
ZEAMX = *Zen mays* (maize)

TABLE 50

Effect (% visual injury) of compound 1 (EC) and Rinskor ™ on weeds.

| Application Rate | compound 1 (g ae/ha) | 5 | 0 | 5 |
|---|---|---|---|---|
|  | Rinskor ™ (g ae/ha) | 0 | 5 | 5 |
| ABUTH | Obs | 70 | 80 | 97 |
|  | Exp |  |  | 94 |
|  | Δ |  |  | 3 |
| BRSNN | Obs | 50 | 20 | 85 |
|  | Exp |  |  | 60 |
|  | Δ |  |  | 25 |
| CIRAR | Obs | 10 | 70 | 75 |
|  | Exp |  |  | 73 |
|  | Δ |  |  | 2 |
| CYPES | Obs | 30 | 70 | 80 |
|  | Exp |  |  | 79 |
|  | Δ |  |  | 1 |
| DIGSA | Obs | 0 | 0 | 20 |
|  | Exp |  |  | 0 |
|  | Δ |  |  | 20 |
| HELAN | Obs | 80 | 85 | 100 |
|  | Exp |  |  | 97 |
|  | Δ |  |  | 3 |
| KCHSC | Obs | 65 | 50 | 85 |
|  | Exp |  |  | 83 |
|  | Δ |  |  | 3 |
| POLCO | Obs | 95 | 60 | 100 |
|  | Exp |  |  | 98 |
|  | Δ |  |  | 2 |
| VIOTR | Obs | 10 | 10 | 20 |
|  | Exp |  |  | 19 |
|  | Δ |  |  | 1 |
| ORYSA | Obs | 0 | 0 | 0 |
|  | Exp |  |  | 0 |
|  | Δ |  |  | 0 |
| TRZAW | Obs | 10 | 0 | 0 |
|  | Exp |  |  | 10 |
|  | Δ |  |  | −10 |

TABLE 50-continued

Effect (% visual injury) of compound 1 (EC) and Rinskor™ on weeds.

| Application Rate | compound 1 (g ae/ha) | 5 | 0 | 5 |
|---|---|---|---|---|
| | Rinskor™ (g ae/ha) | 0 | 5 | 5 |
| ZEAMX | Obs | 5 | 0 | 10 |
| | Exp | | | 5 |
| | Δ | | | 5 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
CYPES = *Cyperus esculentus* (nutsedge)
DIGSA = *Digitaria sanguinalis* (large crabgrass)
HELSN = *Helianthus sanguinalis* (sunflower)
KCHSC = *Kochia scoparia* (kochia)
ORYSA = *Oryza sativa* (common rice)
POLCO = *Polygonum convolvulus* (wild buckwheat)
TRZAW = *Triticum aestivum* (winter wheat)
VIOTR = *Viola tricolor* (wild pansy)
ZEAMN = *Zea mays* (maize)

TABLE 51

Effect (% visual injury) of compound 1 (EC) and quinclorac on weeds.

| Application Rate | compound 1 (g ae/ha) | 5 | 10 | 0 | 5 | 10 |
|---|---|---|---|---|---|---|
| | quinclorac (g ae/ha) | 0 | 0 | 140 | 140 | 140 |
| ABUTH | Obs | 50 | 60 | 0 | 60 | 70 |
| | Exp | | | | 50 | 60 |
| | Δ | | | | 10 | 10 |
| AMARE | Obs | 75 | 97 | 10 | 100 | 100 |
| | Exp | | | | 78 | 97 |
| | Δ | | | | 23 | 3 |
| BRSNW | Obs | 40 | 45 | 0 | 60 | 50 |
| | Exp | | | | 40 | 45 |
| | Δ | | | | 20 | 5 |
| CHEAL | Obs | 90 | 100 | 5 | 97 | 100 |
| | Exp | | | | 91 | 100 |
| | Δ | | | | 7 | 0 |
| EPHHL | Obs | 97 | 97 | 20 | 100 | 100 |
| | Exp | | | | 98 | 98 |
| | Δ | | | | 2 | 2 |
| GLXMA | Obs | 95 | 100 | 30 | 100 | 100 |
| | Exp | | | | 97 | 100 |
| | Δ | | | | 4 | 0 |
| IPOHE | Obs | 10 | 10 | 65 | 70 | 70 |
| | Exp | | | | 69 | 69 |
| | Δ | | | | 2 | 2 |
| KCHSC | Obs | 60 | 60 | 0 | 70 | 70 |
| | Exp | | | | 60 | 60 |
| | Δ | | | | 10 | 10 |
| SORVU | Obs | 0 | 50 | 0 | 20 | 10 |
| | Exp | | | | 0 | 50 |
| | Δ | | | | 20 | −40 |
| STEME | Obs | 70 | 70 | 10 | 100 | 100 |
| | Exp | | | | 73 | 73 |
| | Δ | | | | 27 | 27 |
| VIOTR | Obs | 5 | 10 | 10 | 40 | 30 |
| | Exp | | | | 15 | 19 |
| | Δ | | | | 26 | 11 |
| ORYSA | Obs | 0 | 10 | 0 | 0 | 10 |
| | Exp | | | | 0 | 10 |
| | Δ | | | | 0 | 0 |
| TRZAW | Obs | 0 | 0 | 0 | 0 | 0 |
| | Exp | | | | 0 | 0 |
| | Δ | | | | 0 | 0 |
| ZEAMX | Obs | 0 | 0 | 0 | 0 | 0 |
| | Exp | | | | 0 | 0 |
| | Δ | | | | 0 | 0 | g ae/ha = grams acid equivalent per hectare;
ABUTH = *Abutilon theophrasti* (velvetleaf);
AMARE = *Amaranthus retroflexus* (pigweed);
BRSNW = *Brassica napus* (winter rape);
CHEAL = *Chenopodium album* L. (common lambsquarters);
EPHHL = *Euphorbia heterophylla* (poinsettia);
GLXMA = *Glycine max* (soybean);
IPOHE = *Ipomoea hederacea* (ivyleaf morningglory);
KCHSC = *Kochia scoparia* (kochia);
ORYSA = *Oryza sativa* (common rice);
SORVU = *Sorghum vulgare* (grain sorghum);
STEME = *Stellaria media* (common chickweed);
TRZAW = *Triticum aestivum* (winter wheat);
VIOTR = *Viola tricolor* (wild pansy);
ZEAMX = *Zea mays* (maize)

TABLE 52

Effect (% visual injury) of compound 1 (EC) and triclopyr-butotyl on weeds.

| Application Rate | compound 1 (g ae/ha) | 5 | 0 | 5 |
|---|---|---|---|---|
| | triclopyr-butotyl (g ae/ha) | 0 | 280 | 280 |
| ABUTH | Obs | 70 | 20 | 100 |
| | Exp | | | 76 |
| | Δ | | | 24 |
| BRSNN | Obs | 50 | 80 | 100 |
| | Exp | | | 90 |
| | Δ | | | 10 |
| CIRAR | Obs | 10 | 85 | 93 |
| | Exp | | | 87 |
| | Δ | | | 7 |
| CYPES | Obs | 30 | 10 | 70 |
| | Exp | | | 37 |
| | Δ | | | 33 |
| DIGSA | Obs | 0 | 0 | 30 |
| | Exp | | | 0 |
| | Δ | | | 30 |
| ECHCG | Obs | 65 | 0 | 70 |
| | Exp | | | 65 |
| | Δ | | | 5 |
| KCHSC | Obs | 65 | 50 | 90 |
| | Exp | | | 83 |
| | Δ | | | 8 |
| STEME | Obs | 60 | 20 | 85 |
| | Exp | | | 68 |
| | Δ | | | 17 |
| VIOTR | Obs | 10 | 65 | 95 |
| | Exp | | | 69 |
| | Δ | | | 27 |
| ORYSA | Obs | 0 | 0 | 0 |
| | Exp | | | 0 |
| | Δ | | | 0 |
| TRZAW | Obs | 10 | 15 | 10 |
| | Exp | | | 24 |
| | Δ | | | −14 |

TABLE 52-continued

Effect (% visual injury) of compound 1 (EC) and triclopyr-butotyl on weeds.

| Application Rate | compound 1 (g ae/ha)<br>triclopyr-butotyl(g ae/ha) | 5<br>0 | 0<br>280 | 5<br>280 |
|---|---|---|---|---|
| ZEAMX | Obs | 5 | 10 | 30 |
|  | Exp |  |  | 15 |
|  | Δ |  |  | 16 | g ae/ha = grams acid equivalent per hectare
ABUTH = *Abutilon theophrasti* (velvetleaf)
BRSNN = *Brassica napus* (spring rape)
CIRAR = *Cirsium arvense* (Canadian thistle)
CYPES = *Cyperus esculentus* (nutsedge)
DIGSA = *Digitaria sanguinalis* (large crabgrass)
ECHCG = *Echinochloa crus-galli* (barnyardgrass)
KCHSC = *Kochia scoparia* (kochia)
ORYSA = *Oryza sativa* (common rice)
STEME = *Stellaria media* (common chickweed)
TRZAW = *Triticum aestivum* (winter wheat)
VIOTR = *Viola tricolor* (wild pansy)
ZEAMN = *Zen mays* (maize)

TABLE 53

Effect (% visual injury) of compound 2 (EC) and 2,4-D EHE on weeds.

| Application Rate | compound 2 (g ae/ha)<br>2,4-D EHE (g ae/ha) | 5<br>0 | 10<br>0 | 0<br>140 | 5<br>140 | 10<br>140 |
|---|---|---|---|---|---|---|
| ALOMY | Obs | 0 | 0 | 0 | 10 | 15 |
|  | Exp |  |  |  | 0 | 0 |
|  | Δ |  |  |  | 10 | 15 |
| AMARE | Obs | 88 | 100 | 75 | 100 | 95 |
|  | Exp |  |  |  | 97 | 100 |
|  | Δ |  |  |  | 3 | -5 |
| BRSNN | Obs | 30 | 55 | 65 | 87 | 83 |
|  | Exp |  |  |  | 76 | 84 |
|  | Δ |  |  |  | 11 | -2 |
| CYPES | Obs | 5 | 10 | 10 | 13 | 25 |
|  | Exp |  |  |  | 15 | 19 |
|  | Δ |  |  |  | -2 | 6 |
| EPHHL | Obs | 35 | 75 | 5 | 55 | 100 |
|  | Exp |  |  |  | 38 | 76 |
|  | Δ |  |  |  | 17 | 24 |
| IPOHE | Obs | 10 | 20 | 93 | 95 | 98 |
|  | Exp |  |  |  | 93 | 94 |
|  | Δ |  |  |  | 2 | 4 |
| ORYSA | Obs | 10 | 18 | 10 | 15 | 23 |
|  | Exp |  |  |  | 19 | 26 |
|  | Δ |  |  |  | -4 | -3 |
| TRZAW | Obs | 3 | 3 | 0 | 5 | 8 |
|  | Exp |  |  |  | 3 | 3 |
|  | Δ |  |  |  | 3 | 5 |
| ZEAMX | Obs | 3 | 3 | 0 | 0 | 5 |
|  | Exp |  |  |  | 3 | 3 |
|  | Δ |  |  |  | -3 | 3 | g ae/ha = grams acid equivalent per hectare
ALOMY = *Alopecurus myosuroides* (blackgrass)
AMARE = *Amaranthus retroflexus* (pigweed)
BRSNN = *Brassica napus* (spring rape)
CYPES = *Cyperus esculentus* (nutsedge)
EPHHL = *Euphorbia heterophylla* (poinsettia)
IPOHE = *Ipomoea hederacea* (ivyleaf morningglory)
ORYSA = *Oryza sativa* (common rice)
TRZAW = *Triticum aestivum* (winter wheat)
ZEAMX = *Zea mays* (maize)

TABLE 54

Effect (% visual injury) of compound 2 (EC) and 2,4-D EHE on weeds.

| Application Rate | compound 2 (g ae/ha)<br>2,4-D EHE (g ae/ha) | 5<br>0 | 10<br>0 | 0<br>400 | 5<br>400 | 10<br>400 |
|---|---|---|---|---|---|---|
| AMARE | Obs | 65 | 60 | 80 | 95 | 97 |
|  | Exp |  |  |  | 93 | 83 |
|  | Δ |  |  |  | 2 | 14 |
| BRSNW | Obs | 30 | 50 | 93 | 100 | 100 |
|  | Exp |  |  |  | 95 | 93 |
|  | Δ |  |  |  | 5 | 7 |
| KCHSC | Obs | 30 | 75 | 50 | 70 | 70 |
|  | Exp |  |  |  | 65 | 73 |
|  | Δ |  |  |  | 5 | -3 |
| SASKR | Obs | 10 | 10 | 70 | 90 | 75 |
|  | Exp |  |  |  | 73 | 71 |
|  | Δ |  |  |  | 17 | 4 |
| SINAR | Obs | 95 | 100 | 97 | 100 | 100 |
|  | Exp |  |  |  | 100 | 97 |
|  | Δ |  |  |  | 0 | 3 | g ae/ha = grams acid equivalent per hectare
AMARE = *Amaranthus retroflexus* (pigweed)
BRSNW = *Brassica napus* (winter rape)
KCHSC = *Kochia scoparia* (kochia)
SASKR = *Salsola iberica* (Russian thistle)
SINAR = *Sinapis arvensis* (wild mustard)

TABLE 55

Effect (% visual injury) of compound 2 (EC) and aminopyralid-TIPA on weeds.

| Application Rate | compound 2 (g ae/ha)<br>aminopyralid-TIPA (g ae/ha) | 5<br>0 | 10<br>0 | 0<br>5 | 5<br>5 | 10<br>5 |
|---|---|---|---|---|---|---|
| AVEFA | Obs | 0 | 0 | 0 | 10 | 13 |
|  | Exp |  |  |  | 0 | 0 |
|  | Δ |  |  |  | 10 | 13 |
| DIGSA | Obs | 28 | 53 | 5 | 58 | 70 |
|  | Exp |  |  |  | 31 | 55 |
|  | Δ |  |  |  | 26 | 15 |
| EPHHL | Obs | 35 | 75 | 18 | 90 | 75 |
|  | Exp |  |  |  | 46 | 79 |
|  | Δ |  |  |  | 44 | -4 |
| SORVU | Obs | 38 | 63 | 5 | 50 | 70 |
|  | Exp |  |  |  | 41 | 64 |
|  | Δ |  |  |  | 9 | 6 |
| VIOTR | Obs | 15 | 40 | 48 | 65 | 60 |
|  | Exp |  |  |  | 55 | 69 |
|  | Δ |  |  |  | 10 | -9 |
| TRZAW | Obs | 3 | 3 | 0 | 3 | 0 |
|  | Exp |  |  |  | 3 | 3 |
|  | Δ |  |  |  | 0 | -3 |
| ZEAMX | Obs | 3 | 3 | 3 | 3 | 13 |
|  | Exp |  |  |  | 5 | 5 |
|  | Δ |  |  |  | -2 | 8 | g ae/ha = grams acid equivalent per hectare
AVEFA = *Avena fatua* (wild oat)
DIGSA = *Digitaria sanguinalis* (large crabgrass)
EPHHL = *Euphorbia heterophylla* (poinsettia)
SORVU = *Sorghum vulgare* (grain sorghum)
TRZAW = *Triticum aestivum* (winter wheat)
VIOTR = *Viola tricolor* (wild pansy)
ZEAMX = *Zea mays* (maize)

TABLE 56

Effect (% visual injury) of compound 2 (EC) and clopyralid on weeds.

| Application Rate | compound 2 (g ae/ha) clopyralid (g ae/ha) | | 5 0 | 10 0 | 0 100 | 5 100 | 10 100 |
|---|---|---|---|---|---|---|---|
| AMARE | Obs | | 88 | 100 | 28 | 100 | 100 |
|  | Exp | |  |  |  | 91 | 100 |
|  | Δ | |  |  |  | 9 | 0 |
| BRSNN | Obs | | 30 | 55 | 43 | 75 | 80 |
|  | Exp | |  |  |  | 60 | 74 |
|  | Δ | |  |  |  | 15 | 6 |
| DIGSA | Obs | | 28 | 53 | 0 | 40 | 45 |
|  | Exp | |  |  |  | 28 | 53 |
|  | Δ | |  |  |  | 13 | −8 |
| EPHHL | Obs | | 35 | 75 | 5 | 65 | 65 |
|  | Exp | |  |  |  | 38 | 76 |
|  | Δ | |  |  |  | 27 | −11 |
| IPOHE | Obs | | 10 | 20 | 35 | 60 | 68 |
|  | Exp | |  |  |  | 42 | 48 |
|  | Δ | |  |  |  | 19 | 20 |
| ORYSA | Obs | | 10 | 18 | 0 | 10 | 18 |
|  | Exp | |  |  |  | 10 | 18 |
|  | Δ | |  |  |  | 0 | 0 |
| TRZAW | Obs | | 3 | 3 | 0 | 5 | 3 |
|  | Exp | |  |  |  | 3 | 3 |
|  | Δ | |  |  |  | 3 | 0 |
| ZEAMX | Obs | | 3 | 3 | 0 | 0 | 0 |
|  | Exp | |  |  |  | 3 | 3 |
|  | Δ | |  |  |  | −3 | −3 | g ae/ha = grams acid equivalent per hectare
AMARE = *Amaranthus retroflexus* (pigweed)
BRSNN = *Brassica napus* (spring rape)
DIGSA = *Digitaria sanguinalis* (large crabgrass)
EPHHL = *Euphorbia heterophylla* (poinsettia)
IPOHE = *Ipomoea hederacea* (ivyleaf morningglory)
ORYSA = *Oryza sativa* (common rice)
TRZAW = *Triticum aestivum* (winter wheat)
ZEAMX = *Zea mays* (maize)

TABLE 57

Effect (% visual injury) of compound 2 (EC) and dicamba-DMA on weeds.

| Application Rate | compound 2 (g ae/ha) dicamba-DMA (g ae/ha) | 5 0 | 10 0 | 0 140 | 5 140 | 10 140 |
|---|---|---|---|---|---|---|
| BRSNN | Obs | 30 | 55 | 50 | 65 | 88 |
|  | Exp |  |  |  | 65 | 78 |
|  | Δ |  |  |  | 0 | 10 |
| CHEAL | Obs | 88 | 99 | 85 | 100 | 100 |
|  | Exp |  |  |  | 98 | 100 |
|  | Δ |  |  |  | 2 | 0 |
| DIGSA | Obs | 28 | 53 | 0 | 40 | 65 |
|  | Exp |  |  |  | 28 | 53 |
|  | Δ |  |  |  | 13 | 13 |
| EPHHL | Obs | 35 | 75 | 20 | 90 | 100 |
|  | Exp |  |  |  | 48 | 80 |
|  | Δ |  |  |  | 42 | 20 |
| ORYSA | Obs | 10 | 18 | 5 | 13 | 20 |
|  | Exp |  |  |  | 15 | 22 |
|  | Δ |  |  |  | −2 | −2 |
| TRZAW | Obs | 3 | 3 | 0 | 0 | 0 |
|  | Exp |  |  |  | 3 | 3 |
|  | Δ |  |  |  | −3 | −3 |
| ZEAMX | Obs | 3 | 3 | 0 | 0 | 0 |
|  | Exp |  |  |  | 3 | 3 |
|  | Δ |  |  |  | −3 | −3 | g ae/ha = grams acid equivalent per hectare
BRSNN = *Brassica napus* (spring rape)
CHEAL = *Chenopodium album* L. (common lambsquarters)
DIGSA = *Digitaria sanguinalis* (large crabgrass)
EPHHL = *Euphorbia heterophylla* (poinsettia)
ORYSA = *Oryza sativa* (common rice)
TRZAW = *Triticum aestivum* (winter wheat)
ZEAMX = *Zea mays* (maize)

TABLE 58

Effect (% visual injury) of compound 2 (EC) and fluroxypyr-MHE on weeds.

| Application Rate | compound 2 (g ae/ha) fluroxypyr-MHE (g ae/ha) | 5 0 | 10 0 | 0 70 | 5 70 | 10 70 |
|---|---|---|---|---|---|---|
| ABUTH | Obs | 78 | 95 | 40 | 95 | 100 |
|  | Exp |  |  |  | 87 | 97 |
|  | Δ |  |  |  | 9 | 3 |
| ALOMY | Obs | 0 | 0 | 0 | 3 | 8 |
|  | Exp |  |  |  | 0 | 0 |
|  | Δ |  |  |  | 3 | 8 |
| AMARE | Obs | 88 | 100 | 70 | 100 | 100 |
|  | Exp |  |  |  | 96 | 100 |
|  | Δ |  |  |  | 4 | 0 |
| AVEFA | Obs | 0 | 0 | 0 | 8 | 3 |
|  | Exp |  |  |  | 0 | 0 |
|  | Δ |  |  |  | 8 | 3 |
| BRSNN | Obs | 30 | 55 | 15 | 63 | 75 |
|  | Exp |  |  |  | 41 | 62 |
|  | Δ |  |  |  | 22 | 13 |
| CYPES | Obs | 5 | 10 | 0 | 5 | 18 |
|  | Exp |  |  |  | 5 | 10 |
|  | Δ |  |  |  | 0 | 8 |
| DIGSA | Obs | 28 | 53 | 33 | 73 | 70 |
|  | Exp |  |  |  | 51 | 68 |
|  | Δ |  |  |  | 21 | 2 |
| EPHHL | Obs | 35 | 75 | 18 | 50 | 85 |
|  | Exp |  |  |  | 46 | 79 |
|  | Δ |  |  |  | 4 | 6 |
| IPOHE | Obs | 10 | 20 | 80 | 93 | 93 |
|  | Exp |  |  |  | 82 | 84 |
|  | Δ |  |  |  | 11 | 9 |
| VIOTR | Obs | 15 | 40 | 80 | 87 | 88 |
|  | Exp |  |  |  | 83 | 88 |
|  | Δ |  |  |  | 4 | −1 |
| TRZAW | Obs | 3 | 3 | 0 | 5 | 0 |
|  | Exp |  |  |  | 3 | 3 |
|  | Δ |  |  |  | 3 | −3 |
| ZEAMX | Obs | 3 | 3 | 0 | 3 | 8 |
|  | Exp |  |  |  | 3 | 3 |
|  | Δ |  |  |  | 0 | 5 | g ae/ha = grams acid equivalent per hectare
ABUTH = *Abutilon theophrasti* (velvetleaf)
ALOMY = *Alopecurus myosuroides* (blackgrass)
AMARE = *Amaranthus retroflexus* (pigweed)
AVEFA = *Avena fatua* (wild oat)
BRSNN = *Brassica napus* (spring rape)
CYPES = *Cyperus esculentus* (nutsedge)
DIGSA = *Digitaria sanguinalis* (large crabgrass)
EPHHL = *Euphorbia heterophylla* (poinsettia)
IPOHE = *Ipomoea hederacea* (ivyleaf morningglory)
TRZAW = *Triticum aestivum* (winter wheat)
VIOTR = *Viola tricolor* (wild pansy)
ZEAMX = *Zea mays* (maize)

TABLE 59

Effect (% visual injury) of compound 2 (EC) and MCPA EHE on weeds.

| Application Rate | compound 2 (g ae/ha)<br>MCPA EHE (g ae/ha) | 5<br>0 | 10<br>0 | 0<br>140 | 5<br>140 | 10<br>140 |
|---|---|---|---|---|---|---|
| ABUTH | Obs | 78 | 95 | 0 | 85 | 93 |
|  | Exp |  |  |  | 78 | 95 |
|  | Δ |  |  |  | 8 | −3 |
| AMARE | Obs | 88 | 100 | 70 | 100 | 100 |
|  | Exp |  |  |  | 96 | 100 |
|  | Δ |  |  |  | 4 | 0 |
| BRSNN | Obs | 30 | 55 | 35 | 85 | 93 |
|  | Exp |  |  |  | 55 | 71 |
|  | Δ |  |  |  | 31 | 22 |
| CYPES | Obs | 5 | 10 | 0 | 28 | 35 |
|  | Exp |  |  |  | 5 | 10 |
|  | Δ |  |  |  | 23 | 25 |
| DIGSA | Obs | 28 | 53 | 10 | 40 | 60 |
|  | Exp |  |  |  | 35 | 57 |
|  | Δ |  |  |  | 5 | 3 |
| EPHHL | Obs | 35 | 75 | 0 | 85 | 100 |
|  | Exp |  |  |  | 35 | 75 |
|  | Δ |  |  |  | 50 | 25 |
| IPOHE | Obs | 10 | 20 | 80 | 88 | 83 |
|  | Exp |  |  |  | 82 | 84 |
|  | Δ |  |  |  | 6 | −2 |
| VIOTR | Obs | 15 | 40 | 60 | 70 | 78 |
|  | Exp |  |  |  | 66 | 76 |
|  | Δ |  |  |  | 4 | 2 |
| ORYSA | Obs | 10 | 18 | 3 | 13 | 18 |
|  | Exp |  |  |  | 12 | 20 |
|  | Δ |  |  |  | 0 | −2 |
| TRZAW | Obs | 3 | 3 | 3 | 3 | 0 |
|  | Exp |  |  |  | 5 | 5 |
|  | Δ |  |  |  | −2 | −5 |
| ZEAMX | Obs | 3 | 3 | 0 | 0 | 5 |
|  | Exp |  |  |  | 3 | 3 |
|  | Δ |  |  |  | −3 | 3 | g ae/ha = grams acid equivalent per hectare
ABUTH = *Abutilon theophrasti* (velvetleaf)
AMARE = *Amaranthus retroflexus* (pigweed)
BRSNN = *Brassica napus* (spring rape)
CYPES = *Cyperus esculentus* (nutsedge)
DIGSA = *Digitaria sanguinalis* (large crabgrass)
EPHHL = *Euphorbia heterophylla* (poinsettia)
IPOHE = *Ipomoea hederacea* (ivyleaf morningglory)
ORYSA = *Oryza sativa* (common rice)
TRZAW = *Triticum aestivum* (winter wheat)
VIOTR = *Viola tricolor* (wild pansy)
ZEAMX = *Zea mays* (maize)

Example 8—Greenhouse Trials

Following the protocol in Example 1, compound 1 (EC) and Compound 2 (SC) were combined with diflufenzopyr and applied to kochia (*Kochia scoparia*, KCHSC) and the phytotoxicity of the herbicidal composition was measured. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 60-61.

TABLE 60

Effect (% visual injury) of compound 1 (EC) and diflufenzopyr on *kochia*.

| Application Rate (g ae/ha) | compound 1<br>diflufenzopyr | 8.75<br>0 | 17.5<br>0 | 0<br>3.5 | 0<br>7 | 8.75<br>3.5 | 17.5<br>7 |
|---|---|---|---|---|---|---|---|
| KCHSC | Obs. | 78 | 80 | 0 | 0 | 82 | 87 |
|  | Exp. | — | — | — | — | 78 | 80 |
|  | Δ |  |  |  |  | 4 | 7 | g ae/ha = grams acid equivalents per hectare
KCHSC = *Kochia scoparia* (kochia)

TABLE 61

Effect (% visual injury) of compound 2 (SC) and diflufenzopyr on *kochia*.

| Application Rate (g ae/ha) | compound 2<br>diflufenzopyr | 8.75<br>0 | 17.5<br>0 | 0<br>3.5 | 0<br>7 | 8.75<br>3.5 | 17.5<br>7 |
|---|---|---|---|---|---|---|---|
| KCHSC | Obs. | 84 | 86 | 0 | 0 | 93 | 92 |
|  | Exp. | — | — | — | — | 84 | 86 |
|  | Δ |  |  |  |  | 10 | 6 | g ae/ha = grams acid equivalents per hectare
KCHSC = *Kochia scoparia* (kochia)

Example 9—Greenhouse Trials

Following the protocol in Example 1, compound 1 (EC) was combined with 2,3,5-TIBA or naptalam and applied to common rice (ORYSA), maize (ZEAMX) and winter wheat (TRZAW), and the phytotoxicity of the herbicidal compositions was measured. In addition, the efficacy of the herbicidal compositions on velvetleaf (*Abutilon theophrasti*, ABUTH), Chinese kale (*Brassica alboglabra*, BRSAG), brown mustard (*Brassica juncea*, BRSJU), rutabaga (*Brassica napus* var. *napobrassica*, BRSNA), spring rape (*Brassica napus*, BRSNN), Roundup Ready rape (*Brassica napus*, BRSNN-RR) winter rape (*Brassica napus*, BRSNW), turnip (*Brassica rapa*, BRSRR), Canadian thistle (*Cirsium arvense* CIRAR), common sunflower (*Helianthus annuus*, HELAN), wild buckwheat (*Polygonum convolvulus*, POLCO), wild pansy (*Viola tricolor*, VIOTR) was evaluated. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 62-63.

TABLE 62

Effect (% visual injury) of compound 1 (EC) and 2,3,5-TIBA on weeds.

| Application Rate | compound 1 (g ae/ha)<br>2,3,5-TIBA (g ai/ha) | 5<br>0 | 0<br>140 | 5<br>140 |
|---|---|---|---|---|
| ABUTH | Obs | 60 | 0 | 70 |
|  | Exp |  |  | 60 |
|  | Δ |  |  | 10 |
| BRSAG | Obs | 15 | 0 | 30 |
|  | Exp |  |  | 15 |
|  | Δ |  |  | 15 |
| BRSJU | Obs | 60 | 10 | 85 |
|  | Exp |  |  | 64 |
|  | Δ |  |  | 21 |

TABLE 62-continued

Effect (% visual injury) of compound 1 (EC) and 2,3,5-TIBA on weeds.

| Application Rate | compound 1 (g ae/ha)<br>2,3,5-TIBA (g ai/ha) | | 5<br>0 | 0<br>140 | 5<br>140 |
|---|---|---|---|---|---|
| BRSNN | Obs | | 50 | 5 | 60 |
| | Exp | | | | 53 |
| | Δ | | | | 8 |
| BRSNN-RR | Obs | | 35 | 0 | 65 |
| | Exp | | | | 35 |
| | Δ | | | | 30 |
| BRSNW | Obs | | 30 | 0 | 85 |
| | Exp | | | | 30 |
| | Δ | | | | 55 |
| BRSRR | Obs | | 50 | 20 | 65 |
| | Exp | | | | 60 |
| | Δ | | | | 5 |
| HELAN | Obs | | 70 | 0 | 97 |
| | Exp | | | | 70 |
| | Δ | | | | 27 |
| POLCO | Obs | | 65 | 0 | 80 |
| | Exp | | | | 65 |
| | Δ | | | | 15 |
| VIOTR | Obs | | 5 | 0 | 30 |
| | Exp | | | | 5 |
| | Δ | | | | 25 |
| ORYSA | Obs | | 5 | 0 | 10 |
| | Exp | | | | 5 |
| | Δ | | | | 5 |
| TRZAW | Obs | | 5 | 0 | 10 |
| | Exp | | | | 5 |
| | Δ | | | | 5 |
| ZEAMX | Obs | | 0 | 0 | 0 |
| | Exp | | | | 0 |
| | Δ | | | | 0 | g ae/ha = grams acid equivalent per hectare; g ai/ha = grams active ingredient per hectare; ABUTH = *Abutilon theophrasti* (velvetleaf); BRSAG = *Brassica alboglabra* (Chinese kale); BRSNA = *Brassica juncea* (brown mustard); BRSNN = *Brassica napus* (spring rape); BRSNN-RR = *Brassica napus* (spring rape, Roundup Ready); BRSNW = *Brassica lupus* (winter rape); BRSRR = *Brassica rapa* (turnip); HELAN = *Helianthus annuus* (common sunflower); ORYSA = *Oryza sativa* (common rice); POLCO = *Polygonum convolvulus* (wild buckwheat); TRZAW = *Triticum aestivum* (winter wheat); VIOTR = *Viola tricolor* (wild pansy); ZEAMX = *Zea mays* (maize)

TABLE 63

Effect (% visual injury) of compound 1 (EC) and naptalam on weeds.

| Application Rate | compound 1 (g ae/ha)<br>naptalam (g ai/ha) | | 5<br>0 | 0<br>140 | 5<br>140 |
|---|---|---|---|---|---|
| ABUTH | Obs | | 60 | 0 | 65 |
| | Exp | | | | 60 |
| | Δ | | | | 5 |
| BRSAG | Obs | | 15 | 0 | 50 |
| | Exp | | | | 15 |
| | Δ | | | | 35 |
| BRSNA | Obs | | 65 | 0 | 100 |
| | Exp | | | | 65 |
| | Δ | | | | 35 |
| BRSNN-RR | Obs | | 35 | 0 | 63 |
| | Exp | | | | 35 |
| | Δ | | | | 28 |
| BRSNW | Obs | | 50 | 0 | 60 |
| | Exp | | | | 50 |
| | Δ | | | | 10 |
| BRSRR | Obs | | 50 | 0 | 70 |
| | Exp | | | | 50 |
| | Δ | | | | 20 |
| CIRAR | Obs | | 10 | 0 | 70 |
| | Exp | | | | 10 |
| | Δ | | | | 60 |
| HELAN | Obs | | 70 | 0 | 85 |
| | Exp | | | | 70 |
| | Δ | | | | 15 |
| POLCO | Obs | | 65 | 0 | 80 |
| | Exp | | | | 65 |
| | Δ | | | | 15 |
| VIOTR | Obs | | 5 | 0 | 30 |
| | Exp | | | | 5 |
| | Δ | | | | 25 |
| ORYSA | Obs | | 5 | 0 | 10 |
| | Exp | | | | 5 |
| | Δ | | | | 5 |
| TRZAW | Obs | | 5 | 0 | 5 |
| | Exp | | | | 5 |
| | Δ | | | | 0 |
| ZEAMX | Obs | | 0 | 0 | 0 |
| | Exp | | | | 0 |
| | Δ | | | | 0 | g ae/ha = grams acid equivalent per hectare; g ai/ha = grams active ingredient per hectare; ABUTH = *Abutilon theophrasti* (velvetleaf); BRSAG = *Brassica alboglabra* (Chinese kale); BRSNA = *Brassica juncea* (brown mustard); BRSNN = *Brassica napus* (spring rape); BRSNN-RR = *Brassica napus* (spring rape, Roundup Ready); BRSNW = *Brassica lupus* (winter rape); BRSRR = *Brassica rapa* (turnip); HELAN = *Helianthus annuus* (common sunflower); ORYSA = *Oryza sativa* (common rice); POLCO = *Polygonum convolvulus* (wild buckwheat); TRZAW = *Triticum aestivum* (winter wheat); VIOTR = *Viola tricolor* (wild pansy); ZEAMX = *Zea mays* (maize)

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a herbicidally effective amount of (a) a pyridine carboxylic acid herbicide or an agriculturally acceptable N-oxide, salt, or ester thereof, and (b) a synthetic auxin herbicide, or an agriculturally acceptable salt or ester thereof,
   wherein the pyridine carboxylic acid herbicide comprises a compound defined by Formula (I)

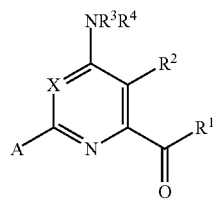

(I)

wherein
- X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;
- $R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;
- $R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;
- $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;
- A is one of groups A21 to A36

A21

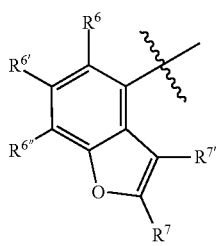

A22

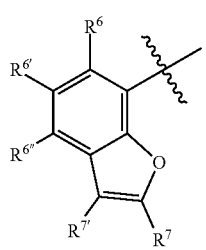

A23

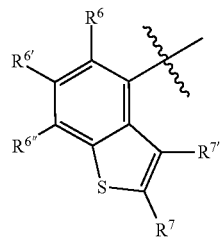

A24

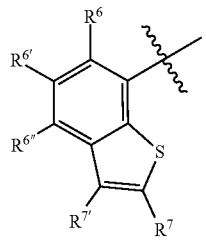

A25

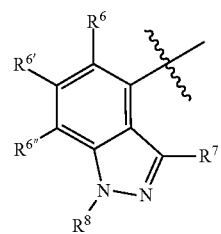

A26

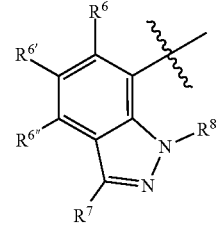

A27

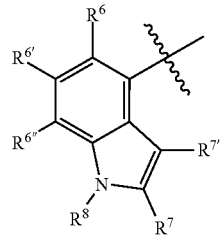

A28

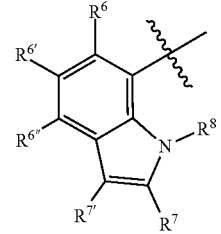

A29 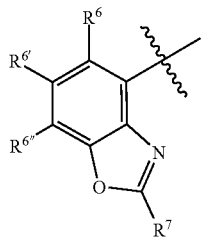

A30 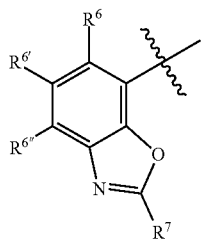

A31 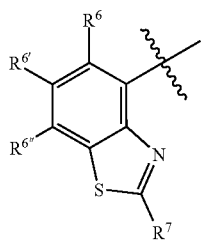

A32 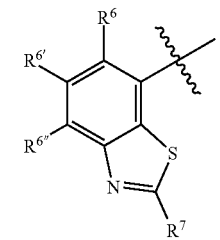

A33 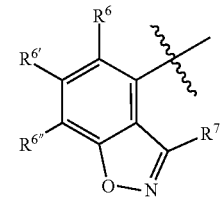

A34 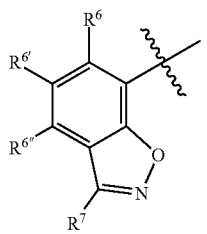

A35 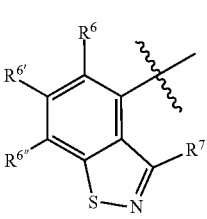

A36 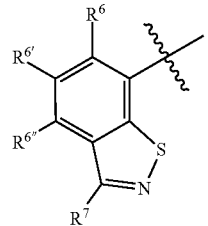

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

2. The composition of claim 1, wherein the pyridine carboxylic acid herbicide comprises a compound defined by Formula (II)

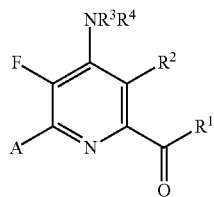

(II)

wherein $R^1$ is $OR^{1'}$ or $NR^{1''}R^{1'''}$, wherein $R^{1'}$ is hydrogen, $C_1$-$C_8$ alkyl, $C_1$-$C_6$ haloalkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, C$_1$-C$_6$ dialkylphosphonyl, or R$^3$ and R$^4$ taken together with N is a 5- or 6-membered saturated ring, or R$^3$ and R$^4$ taken together represent =CR$^{3'}$(R$^{4'}$), wherein R$^{3'}$ and R$^{4'}$ are independently hydrogen, C$_1$-C$_6$ alkyl, C$_3$-C$_6$ alkenyl, C$_3$-C$_6$ alkynyl, C$_1$-C$_6$ alkoxy or C$_1$-C$_6$ alkylamino, or, R$^{3'}$ and R$^{4'}$ taken together with =C represent a 5- or 6-membered saturated ring;

A is A21, A22, A23, A24, A25, A26, A27, A28, A29, A30, A31, A32, A33, A34, A35, or A36;

R$^6$, R$^{6'}$, and R$^{6''}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino or C$_2$-C$_4$ haloalkylamino, OH, CN, or NO$_2$;

R$^7$ and R$^{7'}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, C$_2$-C$_4$ haloalkylamino, or phenyl; and R$^8$ is hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, C$_1$-C$_6$ alkoxycarbonyl, C$_1$-C$_6$ alkylcarbamyl, C$_1$-C$_6$ alkylsulfonyl, C$_1$-C$_6$ trialkylsilyl, or phenyl;

or an agriculturally acceptable N-oxide or salt thereof.

3. The composition of claim 2, wherein
R$^1$ is OR$^{1'}$, wherein R$^{1'}$ is hydrogen, C$_1$-C$_8$ alkyl, or C$_7$-C$_{10}$ arylalkyl;
R$^2$ is halogen, C$_1$-C$_4$ alkyl, C$_1$-C$_4$ haloalkyl, C$_2$-C$_4$-alkenyl, C$_2$-C$_4$ haloalkenyl, C$_2$-C$_4$ alkynyl, C$_1$-C$_4$-alkoxy, C$_1$-C$_4$ haloalkoxy, C$_1$-C$_4$ alkylthio, or C$_1$-C$_4$ haloalkylthio;
R$^3$ and R$^4$ are hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, or R$^3$ and R$^4$ taken together represent =CR$^{3'}$(R$^{4'}$), wherein R$^{3'}$ and R$^{4'}$ are independently hydrogen, C$_1$-C$_6$ alkyl, C$_3$-C$_6$ alkenyl, C$_3$-C$_6$ alkynyl, C$_1$-C$_6$ alkoxy or C$_1$-C$_6$ alkylamino;
A is A21, A22, A23, A24, A27, A28, A29, A30, A31, or A32;
R$^6$, R$^{6'}$, and R$^{6''}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, CN, or NO$_2$;
R$^7$ and R$^{7'}$ are independently hydrogen, halogen, C$_1$-C$_4$ alkyl, C$_1$-C$_4$ haloalkyl, C$_1$-C$_3$ alkoxy, C$_1$-C$_3$ haloalkoxy, C$_1$-C$_3$ alkylthio, cyclopropyl, amino or C$_1$-C$_4$ alkylamino; and
R$^8$ is hydrogen, C$_1$-C$_6$ alkyl, C$_1$-C$_4$ haloalkyl, C$_3$-C$_6$ alkenyl, C$_3$-C$_6$ haloalkenyl, formyl, C$_1$-C$_3$ alkylcarbonyl, C$_1$-C$_3$ haloalkylcarbonyl, C$_1$-C$_6$ alkoxycarbonyl, or C$_1$-C$_6$ alkylcarbamyl.

4. The composition of claim 1, wherein (b) comprises picloram; agriculturally acceptable salts and esters of picloram; a triclopyr choline salt a triclopyr ester; a triclopyr amine; or a combination thereof.

5. The composition of claim 1, wherein the weight ratio of (a) to (b) is from 1:3000 to 60:1.

6. The composition of claim 1, wherein the weight ratio of (a) to (b) is from 1:200 to 8:1.

7. The composition of claim 1, wherein the weight ratio of (a) to (b) is from 1:70 to 1:1.

8. The composition of claim 1, wherein (b) is a triclopyr choline salt; a triclopyr ester; a triclopyr amine; or a combination thereof.

9. The composition of claim 1, wherein (b) is picloram and the weight ratio of (a) to (b) is 1:2.

10. The composition of claim 1, further comprising a herbicidal safener.

11. The composition of claim 1, further comprising an agriculturally acceptable adjuvant or carrier.

12. The composition of claim 1, further comprising an additional pesticide.

13. The composition of claim 1, wherein the active ingredients in the composition consist of (a) and (b).

14. The composition of claim 1, which wherein the composition is provided as a herbicidal concentrate.

15. The composition of claim 1, wherein A is A21, A22, A23, A24, A29, or A30.

16. The composition of claim 2, wherein A is A21, A22, A23, A24, A29, or A30.

17. The composition of claim 3, wherein A is A21, A22, A23, A24, A29, or A30.

18. A method of controlling undesirable vegetation comprising applying to vegetation or an area adjacent the vegetation or applying to soil or water to control the emergence or growth of vegetation the composition of claim 1.

19. The method of claim 18, wherein (a) and (b) are applied post-emergence to the undesirable vegetation.

20. The method of claim 18, wherein (a) is applied in an amount of from 0.1 g ae/ha to 300 g ae/ha.

21. The method of claim 18, wherein (a) is applied in an amount of from 5 g ae/ha to 40 g ae/ha.

22. The method of claim 18, wherein (b) is applied in an amount of from 5 g ae/ha to 3000 g ae/ha.

23. The method of claim 18, wherein (b) is applied in an amount of from 10 g ae/ha to 2300 g ae/ha.

24. The method of claim 18, wherein (b) is applied in an amount of from 10 g ae/ha to 280 g ae/ha.

25. The method of claim 18, further comprising applying a herbicidal safener.

26. The method of claim 18, further comprising applying an additional pesticide.

27. The method of claim 18, wherein the undesirable vegetation is controlled in spring barley (*Hordeum vulgare*, HORVS), winter wheat (*Triticum aestivum*, TRZAW), spring wheat (*Triticum aestivum*, TRZAS), rice, maize, or combinations thereof.

28. The method of claim 18, wherein the undesirable vegetation includes a broadleaf weed.

29. The method of claim 18, wherein the undesirable vegetation comprises a herbicide resistant or tolerant weed.

30. The method of claim 18, wherein the undesirable vegetation includes velvetleaf (*Abutilon theophrasti*, ABUTH), pigweed (*Amaranthus retroflexus*, AMARE), rape (*Brassica napus*, BRSNN), winter rape (*Brassica napus*, BRSNW), common lambsquarters (*Chenopodium album* L., CHEAL), thistle (*Cirsium arvense*, CIRAR), *Cyperus* species, poinsettia (*Euphorbia heterophylla*, EPHHL), sunflower (*Helianthus annus*, HELAN), ivyleaf morningglory (*Ipomoea hederacea*, IPOHE), kochia (*Kochia scoparia*, KCHSC), mallow (*Malva pusilla*, MALPU), wild buckwheat (*Polygonum convolvulus*, POLCO), *Persicaria* species, wild radish (*Raphanus* raphanistrum, RAPRA), Russian thistle (*Salsola iberica*, SASKR), wild mustard (*Sinapsis arvensis*, SINAR), *Sorghum* species, *Sisymbrium* species, common chickweed (*Stellaria media*, STEME), speedwell, *Veronica* species, wild pansy (*Viola tricolor*, VIOTR), or a combination thereof.

31. The method of claim 18, wherein the active ingredients applied to the vegetation or an area adjacent the vegetation or applied to soil or water to control the emergence or growth of vegetation consist of (a) and (b).

* * * * *